(12) United States Patent
Loumaye et al.

(10) Patent No.: US 11,759,464 B2
(45) Date of Patent: Sep. 19, 2023

(54) GONADOTROPIN-RELEASING HORMONE ANTAGONIST DOSING REGIMENS FOR TREATING UTERINE FIBROIDS AND REDUCING MENSTRUAL BLOOD LOSS

(71) Applicant: ObsEva S.A., Plan-les-Ouates (CH)

(72) Inventors: Ernest Loumaye, Cologny (CH); Jean-Pierre Gotteland, Geneva (CH); Oliver Pohl, Plan-les-Ouates (CH)

(73) Assignee: Kissei Pharmaceutical Co., Ltd., Matsumoto (JP)

( * ) Notice: Subject to any disclaimer, the term of this patent is extended or adjusted under 35 U.S.C. 154(b) by 157 days.

(21) Appl. No.: 16/619,702

(22) PCT Filed: Jun. 5, 2018

(86) PCT No.: PCT/EP2018/064767
§ 371 (c)(1),
(2) Date: Dec. 5, 2019

(87) PCT Pub. No.: WO2018/224497
PCT Pub. Date: Dec. 13, 2018

(65) Prior Publication Data
US 2020/0179390 A1 Jun. 11, 2020

Related U.S. Application Data

(60) Provisional application No. 62/515,232, filed on Jun. 5, 2017.

(51) Int. Cl.
*A61K 31/519* (2006.01)
*A61K 31/565* (2006.01)
(Continued)

(52) U.S. Cl.
CPC .......... *A61K 31/519* (2013.01); *A61K 31/565* (2013.01); *A61K 31/57* (2013.01); *A61P 5/00* (2018.01)

(58) Field of Classification Search
CPC .......................... A61K 31/519; A61K 31/565
(Continued)

(56) References Cited

U.S. PATENT DOCUMENTS 9,040,693 B2  5/2015  Ohno et al.
9,169,266 B2  10/2015  Jo et al.
(Continued)

FOREIGN PATENT DOCUMENTS

CA  3025760 A1  2/2018
EP  2535342 A1 * 12/2012 ........... A61K 9/0053
(Continued)

OTHER PUBLICATIONS

Medical Dictionary.com. Metrofibroma | definition of metrofibroma, accessed Nov. 3, 2021, 1 page. (Year: 2021).*
(Continued)

*Primary Examiner* — Craig D Ricci
*Assistant Examiner* — Janet L Coppins
(74) *Attorney, Agent, or Firm* — Clark & Elbing LLP

(57) ABSTRACT

The invention provides compositions and methods for reducing the volume of menstrual blood loss in a patient, such as a human patient, for instance, that has uterine fibroids, by administration of a gonadotropin-releasing hormone (GnRH) antagonist. Suitable GnRH antagonists useful in conjunction with the compositions and methods described herein include thieno[3,4d]pyrimidine derivatives, such as 3-[2-fluoro-5-(2,3-difluoro-6-methoxybenzyloxy)-4-methoxypheny I]-2,4-dioxo-1,2,3,4-tetrahydrothieno[3,4d]pyrimidine-5-carboxylic acid and the choline salt thereof.

15 Claims, 34 Drawing Sheets

(51) Int. Cl.
    *A61P 5/00*         (2006.01)
    *A61K 31/57*      (2006.01)

(58) Field of Classification Search
    USPC ...................................................... 514/262.1
    See application file for complete search history.

(56) References Cited

U.S. PATENT DOCUMENTS

| | | |
|---|---|---|
| 9,737,539 B2 | 8/2017 | Jo et al. |
| 10,016,433 B2 | 7/2018 | Jo et al. |
| 2019/0134038 A1 | 5/2019 | Jo et al. |
| 2019/0175600 A1 | 6/2019 | Dan et al. |
| 2020/0138819 A1 | 5/2020 | Loumaye et al. |
| 2020/0179390 A1 | 6/2020 | Loumaye et al. |

FOREIGN PATENT DOCUMENTS

| | | |
|---|---|---|
| EP | 3498280 A1 | 6/2019 |
| JP | 2003-525249 A | 8/2003 |
| JP | 2016-513708 A | 5/2016 |
| WO | WO-2007/046392 A1 | 4/2007 |
| WO | WO-2011/099507 A1 | 8/2011 |
| WO | WO-2014/042176 A1 | 3/2014 |
| WO | WO-2014/143669 A1 | 9/2014 |
| WO | WO-2018/030317 A1 | 2/2018 |
| WO | WO-2018/060501 A2 | 4/2018 |
| WO | WO-2018/224497 A1 | 12/2018 |
| WO | WO-2018/224498 A1 | 12/2018 |
| WO | WO-2020/094698 A2 | 5/2020 |

OTHER PUBLICATIONS

PubChem.com, Estradiol compound summary, accessed Nov. 3, 2021, pp. 1-61. (Year: 2021).*
Medical Dictionary.com. Fibroma | definition of fibroma, accessed Nov. 3, 2021, pp. 1-2. (Year: 2021).*
Archer et al, Gynecology vol. 108 No. 1 / Jul. 2017, pp. 152-160.e4. first published online Jun. 1, 2017. (Year: 2017).*
Abbvie, "AbbVie Announces Positive Topline Results from Phase 3 Extension Study Evaluating Investigational Elagolix in Women with Uterine Fibroids," dated Aug. 22, 2018, retrieved on Oct. 1, 2020 (6 pages).
Donnez et al., "Partial suppression of estradiol: a new strategy in endometriosis management?" Fertil Steril. 107(3):568-570 (2017).
Lewis et al., "A Comprehensive Review of the Pharmacologic Management of Uterine Leiomyoma," Biomed Res Int. 2018:2414609 (2018) (11 pages).
International Search Report and Written Opinion for International Application No. PCT/EP2019/080362, dated Jul. 7, 2020 (20 pages).
Invitation to Pay Additional Fees for International Application No. PCT/EP2019/079448, dated Feb. 12, 2020 (14 pages).
International Search Report and Written Opinion for International Application No. PCT/EP2019/079448, dated May 19, 2020 (20 pages).
U.S. Appl. No. 17/291,192, filed May 4, 2021 (270 pages).
Communication pursuant to Article 94(3) for European Patent Application No. 18731976.9, dated May 17, 2021 (6 pages).
ObsEva, "Annual Report 2016," dated Apr. 21, 2017, retrieved on Jul. 28, 2021 (114 pages).
ObsEva, "ObsEva SA Announces the Completion of a Phase 1 PK/PD Clinical Trial Evaluating Different Doses of OBE2109 and Add-Back Therapy," dated Jun. 7, 2017, retrieved on Jul. 28, 2021 (5 pages).
ObsEva, "Building a Leader by Innovating Women's Reproductive Health and Pregnancy Therapeutics," dated Nov. 1, 2017, retrieved on Jul. 28, 2021 (35 pages).
U.S. Appl. No. 16/619,702, Loumaye et al.
"Building a Leader by Innovating Women's Reproductive Health and Pregnancy Therapeutics," ObsEva, Nov. 2017, <http://www.jefferies.com/CMSFiles/Jefferies.com/files/ObsEva.pdf> (35 pages).
"ObsEva SA Announces the Completion of a Phase 1 PK/PD Clinical Trial Evaluating Different Doses of OBE2109 and Add-Back Therapy," ObsEva, retrieved from, <http://www.obseva.com/news/obseva-sa-announces-the-completion-of-a-phase-1-pk-pd-clinical-trial-evaluating-different-doses-of-obe2109-and-add-back-therapy> on Mar. 8, 2018 (2017) (7 pages).
Archer et al., "Elagolix for the management of heavy menstrual bleeding associated with uterine fibroids: results from a phase 2a proof-of-concept study," Fertil Steril. 108(1):152-160.e4 (includes supplemental content) (2017) (13 pages).
International Search Report and Written Opinion for International Application No. PCT/EP2018/064767, dated Aug. 24, 2018 (16 pages).
ObsEva S.A., "Annual Report 2016," <http://investors.obseva.com/phoenix.zhtml?c=254482&p=irol-reportsannual>, (114 pages).
Donnez et al., "Partial suppression of estradiol: a new strategy in endometriosis management?," Fertil Steril. 107(3):568-70 (2017).
Hamdine et al., "Ovarian response prediction in GnRH antagonist treatment for IVF using anti-Müllerian hormone," Hum Reprod. 30(1):170-8 (2015).
International Search Report and Written Opinion for International Application No. PCT/EP2018/064768, dated Oct. 17, 2018 (20 pages).
Signorile et al., "A tissue specific magnetic resonance contrast agent, Gd-AMH, for diagnosis of stromal endometriosis lesions: a phase I study," J Cell Physiol. 230(6):1270-5 (2015).
Pohl et al., "Gonadotropin-Releasing Hormone Receptor Antagonist Mono- and Combination Therapy With Estradiol/Norethindrone Acetate Add-Back: Pharmacodynamics and Safety of OBE2109," J Clin Endocrinol Metab. 103(2):497-504 (2018).
U.S. Appl. No. 17/291,192, Loumaye et al.
U.S. Appl. No. 17/289,418, Gotteland et al.
MacKay, "ObsEva SA: Late-Stage Women's Health Co. w/ Potentially Best-in-Class Lead Asset; Outperform, $27 TP," accessible at <https://research-doc.credit-suisse.com/docView?language=ENG&format=PDF&sourceid=csplusresearchcp&document_id=1071589801&serialid=w5tUz5ckZojLgop%2BFQZCZvq2JSqlpv%2FqYEO7ASCs3sO%3D>, dated Feb. 21, 2017, (44 pages).
WHO Drug Information, "International Nonproprietary Names for Pharmaceutical Substances (INN)," vol. 31, No. 4, published Jan. 19, 2018 (36 pages).
"United States Securities Exchange Commission—Annual Report Persuant to Section 13 or 15(d) of the Securities Exchange Act of 1934—Myovant Sciences Ltd.," Published Jun. 7, 2018, (40 pages).
ObsEva S.A., Informed Consent and Authorization Form, 15-OBE2109-001, accessible at <https://proslc.com/wp-content/uploads/2013/06/EDEWEISS-ENDO-ICF.pdf>, dated Aug. 11, 2016, (21 pages).
Struthers et al., "Suppression of gonadotropins and estradiol in premenopausal women by oral administration of the nonpeptide gonadotropin-releasing hormone antagonist elagolix," J Clin Endocrinol Metab. 94(2):545-51 (2009) (14 pages).
Franke et al., "Gonadotropin-releasing hormone agonist plus "add-back" hormone replacement therapy for treatment of endometriosis: a prospective, randomized, placebo-controlled, double-blind trial," Fertil Steril. 74(3):534-9 (2000).
Chen et al., "Discovery of sodium R-(+)-4-{2-[5-(2-fluoro-3-methoxyphenyl)-3-(2-fluoro-6-[trifluoromethyl]-benzyl)-4-methyl-2,6-dioxo-3,6-dihydro-2H-pyrimidin-1-yl]-1-phenylethylamino}butyrate (elagolix), a potent and orally available nonpeptide antagonist of the human gonadotropin-releasing hormone receptor," J Med Chem. 51(23):7478-7485 (Dec. 2008).
Donnez et al., "Linzagolix with and without hormonal add-back therapy for the treatment of symptomatic uterine fibroids: two randomised, placebo-controlled, phase 3 trials," Lancet. 400(10356):896-907 (Sep. 17, 2022).

* cited by examiner

GONADOTROPIN-RELEASING HORMONE ANTAGONIST DOSING REGIMENS FOR TREATING UTERINE FIBROIDS AND REDUCING MENSTRUAL BLOOD LOSS

FIELD OF THE INVENTION

The invention relates to methods of reducing menstrual blood loss in a patient, such as a patient presenting with or diagnosed as having uterine fibroids, by administration of a gonadotropin-releasing hormone antagonist.

BACKGROUND OF THE INVENTION

Uterine fibroids, also referred to as leiomyomata, are among the most common benign tumors in women. Uterine fibroids are highly prevalent in women of reproductive age and are identified in more than 50% of women between 35 and 50 years of age. The incidence of this pathology positively correlates with age and is commonly addressed by way of surgical interventions, such as hysterectomy (Buttram et al., Fertil Steril. 36:433-445 (1981); and Day Baird et al., Am. J. Obstet. Gynecol. 188:100-107 (2003)). Symptoms associated with uterine fibroids commonly include heavy or prolonged menstrual bleeding, pelvic pressure and pelvic organ compression, back pain, and adverse reproductive outcomes. Heavy menstrual bleeding, which can manifest as a loss of 80 ml of menstrual blood or more per menstrual cycle, may lead to iron deficiency anemia, a key symptom of uterine fibroids and the leading cause of surgical interventions that may include hysterectomy.

Currently approved therapeutics for treating uterine fibroids symptoms provide only short-term benefits, and are generally only indicated prior to surgical intervention or are incompatible with chronic administration due to deleterious side effects. There remains a need for improved therapeutic methods for the reduction of menstrual blood loss, such as in patients suffering from uterine fibroids and patients that have developed an accompanying anemia.

SUMMARY OF THE INVENTION

The invention provides compositions and methods for dosing a patient, such as a mammalian patient (e.g., a human) with a GnRH antagonist for reducing menstrual blood loss. The patient may be suffering from uterine fibroids, and may further present with anemia due, for example, to heavy menstrual bleeding associated with uterine fibroids. For instance, the patient may have iron deficiency anemia. GnRH antagonists that may be used in conjunction with the compositions and methods of the invention include thieno[3,4d]pyrimidine derivatives, such as 3-[2-fluoro-5-(2,3-difluoro-6-methoxybenzyloxy)-4-methoxyphenyl]-2,4-dioxo-1,2,3,4-tetrahydrothieno [3,4d] pyrimidine-5-carboxylic acid or a pharmaceutically acceptable salt thereof, such as the choline salt thereof. Treatment of a patient with a GnRH antagonist as described herein can lead to suppression of endogenous β17-estradiol levels, such as to levels less than 50 pg/ml, less than 20 pg/ml, and less than 10 pg/ml. This reduction in β17-estradiol provides the important therapeutic benefit of attenuated menstrual blood loss. To combat side effects that may arise from hypoestrogenemia, such as a reduction of bone mineral density, in some embodiments the invention features compositions and methods for the administration of add-back therapy, such as the combination of an estrogen and progestin, to the patient undergoing GnRH antagonist treatment. In some embodiments, the dose of GnRH antagonist alone that is administered to the patient does not induce a reduction in bone mineral density and/or other side effects, and in these embodiments add-back therapy is not required. The compositions and methods described herein thus provide advantageous GnRH antagonist dose regimes that suppress heavy menstrual bleeding while simultaneously preventing, minimizing, or reducing the occurrence of side effects associated with a reduction in β17-estradiol.

In a first aspect, the invention features a method of reducing the volume of menstrual blood loss in a patient (e.g., a human patient, such as a premenopausal female human patient), the method including administering to the patient the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I)

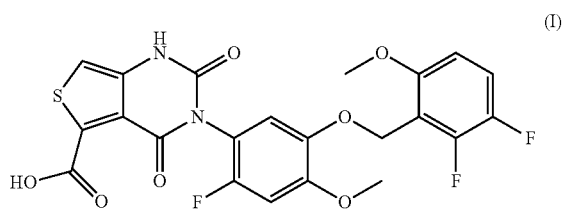 [SMILES: COc1cc(F)c(-n2c(=O)[nH]c3csc(C(=O)O)c3c2=O)cc1OCc1c(OC)ccc(F)c1F]

or a pharmaceutically acceptable salt thereof, in an amount of about 100 mg per dose.

In another aspect, the invention features a method of treating uterine fibroids in a patient (e.g., a human patient, such as a premenopausal female human patient), the method including administering to the patient the GnRH antagonist 3-[2-fluoro-5-(2,3-difluoro-6-methoxybenzyloxy)-4-methoxyphenyl]-2,4-dioxo-1,2,3,4-tetrahydrothieno [3,4d] pyrimidine-5-carboxylic acid, which is the compound represented by formula (I)

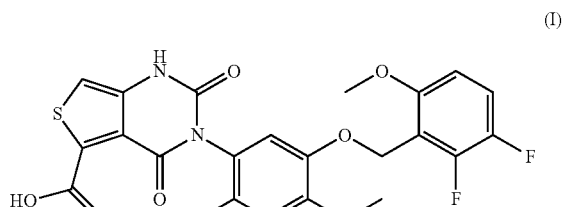

or a pharmaceutically acceptable salt thereof, in an amount of about 100 mg per dose.

In another aspect, the invention features a method of inducing amenorrhea in a patient (e.g., a human patient, such as a premenopausal female human patient, such as one that has uterine fibroids), the method including administering to the patient the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I)

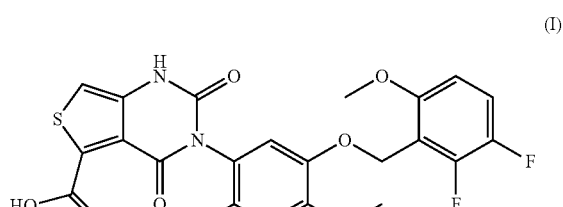

or a pharmaceutically acceptable salt thereof, in an amount of about 100 mg per dose.

In another aspect, the invention features a method of increasing the quantity and/or concentration of hemoglobin in the blood of a patient (e.g., a human patient, such as a premenopausal female human patient, such as one that has uterine fibroids), the method including administering to the patient the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I)

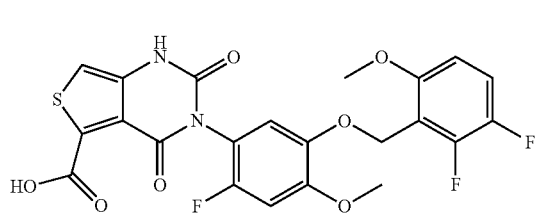

(I)

or a pharmaceutically acceptable salt thereof, in an amount of about 100 mg per dose.

In another aspect, the invention features a method of reducing the concentration of β17-estradiol, follicle-stimulating hormone (FSH), and/or luteinizing hormone (LH) in the blood of a patient (e.g., a human patient, such as a premenopausal female human patient, such as one that has uterine fibroids), the method including administering to the patient the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I)

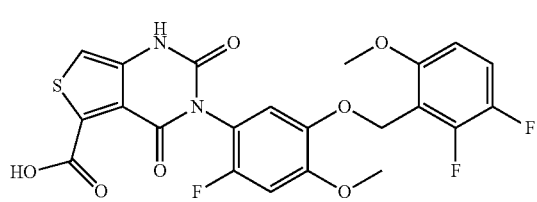

(I)

or a pharmaceutically acceptable salt thereof, in an amount of about 100 mg per dose.

In some embodiments of any of the above aspects, the compound may be administered orally, for example, in the form of a tablet, capsule, gel cap, powder, liquid solution, or liquid suspension. The compound may be administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), or from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others.

In some embodiments, the compound is administered to the patient in an amount of about 100 mg/day (e.g., 100 mg/day). In some embodiments, the compound is administered to the patient in an amount of about 200 mg every 48 hours (e.g., 200 mg every 48 hours). In some embodiments, the compound is administered to the patient in an amount of about 300 mg every 72 hours (e.g., 300 mg every 72 hours). In some embodiments, the compound is administered to the patient in an amount of about 700 mg/week (e.g., 700 mg/week).

In some embodiments, the compound is administered to the patient in an amount of about 50 mg every 12 hours (e.g., 50 mg every 12 hours), in an amount of about 25 mg every 6 hours (e.g., 25 mg every 6 hours), in an amount of about 16.67 mg every 4 hours (e.g., 16.67 mg every 4 hours), in an amount of about 12.5 mg every 3 hours (e.g., 12.5 mg every 3 hours), or the like, e.g., so as to achieve an amount of 100 mg/day.

In some embodiments, the compound is the choline salt of the compound represented by formula (I), shown in formula (II), below.

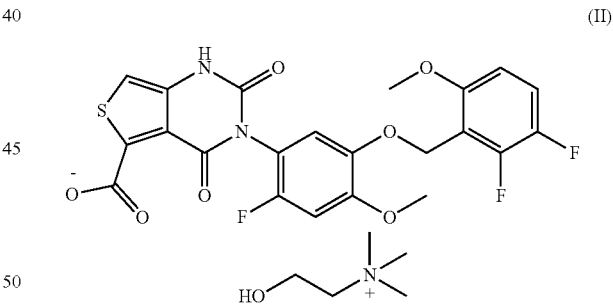

(II)

In some embodiments, the patient has uterine fibroids and the menstrual blood loss is associated with (e.g., caused by) the uterine fibroids. The patient may have anemia, such as an anemia associated with uterine fibroids. For instance, in some embodiments, the patient has iron deficiency anemia, for example, due to the heavy menstrual bleeding associated with uterine fibroids.

In some embodiments, the compound is in a crystalline state. The compound may exhibit characteristic X-ray powder diffraction peaks at about 7.1° 2θ, about 11.5° 2θ, about 19.4° 2θ, about 21.5° 2θ, about 22.0° 2θ, about 22.6° 2θ, about 23.5° 2θ, and about 26.2° 2θ. In some embodiments, the compound exhibits $^{13}$C solid-state nuclear magnetic resonance (NMR) peaks centered at about 55.5 ppm, about 57.1 ppm, about 58.7 ppm, about 69.8 ppm, about 98.1 ppm, about 110.3 ppm, about 111.6 ppm, about 113.7 ppm, about 118.0 ppm, about 145.3 ppm, about 149.8 ppm, and about 155.8 ppm. The compound may exhibit $^{19}$F solid-state NMR peaks centered at about −151.8 ppm, −145.2 ppm, and −131.6 ppm.

In some embodiments, the compound is orally administered to the patient. Other routes of administration that may be used in conjunction with the compositions and methods of the invention are described herein.

In some embodiments, the method includes administering add-back therapy to the patient. The add-back therapy may be administered to the patient concurrently with the GnRH antagonist, prior to administration of the GnRH antagonist, or following administration of the GnRH antagonist. In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of β17-estradiol, ethinyl estradiol, or a conjugated estrogen, such as a conjugated equine estrogen) and/or a progestin (e.g., norethindrone or a compound that is metabolized in vivo to produce norethindrone, such as an ester of norethindrone that is de-esterified in vivo to produce norethindrone, for instance, norethindrone acetate (also referred to herein as "NETA"), among other agents, such as progesterone, norgestimate, medroxyprogesterone, and drospirenone) in the form of a single pharmaceutical composition, such as a single tablet, capsule, gel cap, powder, liquid solution, or liquid suspension. In some embodiments, the add-back therapy is administered orally, transdermally, or intravaginally.

In some embodiments, the add-back therapy is administered to the patient in one or more doses per day, week, month, or year, such as daily, for example, from 1 to 10 times daily, or more (e.g., 1, 2, 3, 4, 5, 6, 7, 8, 9, 10, or more, times daily). In some embodiments, the add-back therapy is administered to the patient once daily, for example, concurrently with the GnRH antagonist. For example, the GnRH antagonist may be administered to the patient orally, and concurrently with oral administration of the GnRH antagonist, the add-back therapy may be administered to the patient orally, transdermally, or intravaginally. In some embodiments, the add-back therapy is administered to the patient in the form of a pharmaceutical composition that further includes the GnRH antagonist, such as a single tablet, capsule, gel cap, powder, liquid solution, or liquid suspension, for instance, as described above and herein. In some embodiments, the add-back therapy is administered to the patient once daily, following administration of the compound. For example, the GnRH antagonist may be administered to the patient orally, and following oral administration of the GnRH antagonist, the add-back therapy may be administered to the patient orally, transdermally, or intravaginally.

In some embodiments, the add-back therapy is administered to the patient once daily, prior to administration of the compound. For example, the GnRH antagonist may be administered to the patient orally, and prior to oral administration of the GnRH antagonist, the add-back therapy may be administered to the patient orally, transdermally, or intravaginally.

In some embodiments, the add-back therapy includes an estrogen. In some embodiments, the estrogen is selected from the group consisting of β17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The β17-estradiol may be administered to the patient one or more times per day, week, or month. The β17-estradiol may be administered to the patient, for example, at a dose of from about 0.1 mg/day to about 2.5 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient at a dose of 1.0 mg/day, for instance, by oral administration. In some embodiments, the β17-estradiol is administered to the patient at a dose of 0.5 mg/day, for instance, by oral administration.

In some embodiments, the estrogen is ethinyl estradiol. The ethinyl estradiol may be administered to the patient, for example, at a dose of from about 1.0 μg to about 6.0 μg, such as at a dose of about 1.0 μg, 1.1 μg, 1.2 μg, 1.3 μg, 1.4 μg, 1.5 μg, 1.6 μg, 1.7 μg, 1.8 μg, 1.9 μg, 2.0 μg, 2.1 μg, 2.2 μg, 2.3 μg, 2.4 μg, 2.5 μg, 2.6 μg, 2.7 μg, 2.8 μg, 2.9 μg, 3.0 μg, 3.1 μg, 3.2 μg, 3.3 μg, 3.4 μg, 3.5 μg, 3.6 μg, 3.7 μg, 3.8 μg, 3.9 μg, 4.0 μg, 4.1 μg, 4.2 μg, 4.2 μg, 4.3 μg, 4.4 μg, 4.5 μg, 4.6 μg, 4.7 μg, 4.8 μg, 4.9 μg, 5.0 μg, 5.1 μg, 5.2 μg, 5.3 μg, 5.4 μg, 5.5 μg, 5.6 μg, 5.7 μg, 5.8 μg, 5.9 μg, or 6.0 μg, for instance, by oral administration. In some embodiments, the ethinyl estradiol is administered to the patient at a dose of 5.0 μg, for instance, by oral administration. In some embodiments, the ethinyl estradiol is administered to the patient at a dose of 2.5 μg, for instance, by oral administration.

The ethinyl estradiol may be administered to the patient one or more times per day, week, or month. The ethinyl estradiol may be administered to the patient, for example, at a dose of from about 1.0 μg/day to about 6.0 μg/day, such as at a dose of about 1.0 μg/day, 1.1 μg/day, 1.2 μg/day, 1.3 μg/day, 1.4 μg/day, 1.5 μg/day, 1.6 μg/day, 1.7 μg/day, 1.8 μg/day, 1.9 μg/day, 2.0 μg/day, 2.1 μg/day, 2.2 μg/day, 2.3 μg/day, 2.4 μg/day, 2.5 μg/day, 2.6 μg/day, 2.7 μg/day, 2.8 μg/day, 2.9 μg/day, 3.0 μg/day, 3.1 μg/day, 3.2 μg/day, 3.3 μg/day, 3.4 μg/day, 3.5 μg/day, 3.6 μg/day, 3.7 μg/day, 3.8 μg/day, 3.9 μg/day, 4.0 μg/day, 4.1 μg/day, 4.2 μg/day, 4.2 μg/day, 4.3 μg/day, 4.4 μg/day, 4.5 μg/day, 4.6 μg/day, 4.7 μg/day, 4.8 μg/day, 4.9 μg/day, 5.0 μg/day, 5.1 μg/day, 5.2 μg/day, 5.3 μg/day, 5.4 μg/day, 5.5 μg/day, 5.6 μg/day, 5.7 μg/day, 5.8 μg/day, 5.9 μg/day, or 6.0 μg/day, for instance, by oral administration. In some embodiments, the ethinyl estradiol is administered to the patient at a dose of 5.0 μg/day, for instance, by oral administration. In some embodiments, the ethinyl estradiol is administered to the patient at a dose of 2.5 μg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, at a dose of from about 0.1 mg/day to about 2.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient at a dose of 0.625 mg/day, for instance, by oral administration. In some embodiments, the conjugated estrogen is administered to the patient at a dose of 0.45 mg/day, for instance, by oral administration. In some embodiments, the conjugated estrogen is administered to the patient at a dose of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient at a dose of 1.0 mg/day, for instance, by oral administration. In some embodiments, the norethindrone is administered to the patient at a dose of 0.5 mg/day, for instance, by oral administration. In some embodiments, the norethindrone is administered to the patient at a dose of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg/day, for instance, by oral administration. In some embodiments, the norethindrone acetate is administered to the patient at a dose of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, at a dose of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient at a dose of 200 mg/day, for instance, by oral administration. In some embodiments, the progesterone is administered to the patient at a dose of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, at a dose of from about 0.01 mg/day to about 2.0 mg/day, such as at a dose of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient at a dose of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, at a dose of from about 0.5 mg/day to about 10.0 mg/day, such as at a dose of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient at a dose of 5.0 mg/day, for instance, by oral administration. In some embodiments, the medroxyprogesterone is administered to the patient at a dose of 2.5 mg/day, for instance, by oral administration. In some embodiments, the medroxyprogesterone is administered to the patient at a dose of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, at a dose of from about 0.1 mg/day to about 1.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient at a dose of 0.5 mg/day, for instance, by oral administration. In some embodiments, the drospirenone is administered to the patient at a dose of 0.25 mg/day, for instance, by oral administration.

In some embodiments, the add-back therapy includes an estrogen and a progestin. In some embodiments, the add-back therapy includes β17-estradiol and norethindrone or a compound that is metabolized in vivo to produce norethindrone, such as an ester of norethindrone that is de-esterified in vivo to produce norethindrone, for instance, norethindrone acetate.

In some embodiments, the add-back therapy includes from about 0.75 mg to about 1.25 mg of β17-estradiol, e.g., administered orally, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and, in the same pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and, in a separate pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the compound is administered to the patient in a fixed-dose composition that contains about 100 mg of the compound (e.g., 100 mg of the compound), from about 0.75 mg to about 1.25 mg of β17-estradiol, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate. In some embodiments, the compound is administered to the patient in a fixed-dose composition that contains about 100 mg of the compound (e.g., 100 mg of the compound), about 1.0 mg of β17-estradiol (e.g., 1.0 mg of β17-estradiol), and about 0.5 mg of norethindrone or a compound that is metabolized in vivo to produce norethindrone, such as an ester of norethindrone that is de-esterified in vivo to produce norethindrone, for instance, norethindrone acetate (e.g., 0.5 mg of norethindrone or a compound that is metabolized in vivo to produce norethindrone, such as an ester of norethindrone that is de-esterified in vivo to produce norethindrone, for instance, norethindrone acetate). In some embodiments, the compound is administered to the patient in a fixed-dose composition that contains 100 mg of the compound, 1.0 mg of β17-estradiol, and 0.5 mg of norethindrone acetate.

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), or from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the above fixed-dose composition is administered to the patient once daily.

In some embodiments, the add-back therapy includes from about 0.25 mg to about 0.75 mg of β17-estradiol, e.g., administered orally, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in the same pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in a separate pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the compound is administered to the patient in a fixed-dose composition that contains about 100 mg of the compound (e.g., 100 mg of the compound), from about 0.25 mg to about 0.75 mg of β17-estradiol, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate. In some embodiments, the compound is administered to the patient in a fixed-dose composition that contains about 100 mg of the compound (e.g., 100 mg of the compound), about 0.5 mg of β17-estradiol (e.g., 0.5 mg of β17-estradiol), and about 0.1 mg of norethindrone or a compound that is metabolized in vivo to produce norethindrone, such as an ester of norethindrone that is de-esterified in vivo to produce norethindrone, for instance, norethindrone acetate (e.g., 0.1 mg of norethindrone or a compound that is metabolized in vivo to produce norethindrone, such as an ester of norethindrone that is de-esterified in vivo to produce norethindrone, for instance, norethindrone acetate). In some embodiments, the compound is administered to the patient in a fixed-dose composition that contains 100 mg of the compound, 0.5 mg of β17-estradiol, and 0.1 mg of norethindrone acetate.

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the fixed-dose composition is administered to the patient once daily.

In some embodiments, the patient exhibits a serum concentration of β17-estradiol that is greater than 20 pg/ml, greater than 30 pg/ml, greater than 40 pg/ml, or greater than 50 pg/ml prior to the administration of the compound to the patient. The serum concentration of β17-estradiol may be reduced to less than 50 pg/ml following administration of the compound to the patient. For instance, in some embodiments, the patient exhibits a serum concentration of β17-estradiol that is reduced to less than 50 pg/ml, less than 45 pg/ml, less than 40 pg/ml, less than 35 pg/ml, less than 30 pg/ml, less than 25 pg/ml, less than 20 pg/ml, less than 15 pg/ml, or less than 10 pg/ml following administration of the compound to the patient. In some embodiments, the patient exhibits a serum concentration of β17-estradiol that is reduced to less than 10 pg/ml to about 40 pg/ml, such as a serum concentration of β17-estradiol of 5 pg/ml, 10 pg/ml, 15 pg/ml, 20 pg/ml, 25 pg/ml, 30 pg/ml, 35 pg/ml, or 40 pg/ml. In some embodiments, the patient exhibits a serum concentration of β17-estradiol of from 5 pg/ml to 50 pg/ml following administration of the compound to the patient (e.g., a serum concentration of β17-estradiol of 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, 20 pg/ml, 21 pg/ml, 22 pg/ml, 23 pg/ml, 24 pg/ml, 25 pg/ml, 26 pg/ml, 27 pg/ml, 28 pg/ml, 29 pg/ml, 30 pg/ml, 31 pg/ml, 32 pg/ml, 33 pg/ml, 34 pg/ml, 35 pg/ml, 36 pg/ml, 37 pg/ml, 38 pg/ml, 39 pg/ml, 40 pg/ml, 41 pg/ml, 42 pg/ml, 43 pg/ml, 44 pg/ml, 45 pg/ml, 46 pg/ml, 47 pg/ml, 48 pg/ml, 49 pg/ml, or 50 pg/ml). In some embodiments, the patient exhibits a serum concentration of β17-estradiol of from 5 pg/ml to 20 pg/ml following administration of the compound to the patient (e.g., a serum concentration of β17-estradiol of 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, or 20 pg/ml). In some embodiments, the patient exhibits a serum concentration of β17-estradiol of from 5 pg/ml to 10 pg/ml following administration of the compound to the patient (e.g., a serum concentration of β17-estradiol of 5 pg/ml, 6 pg/ml, 7 pg/ml, 8 pg/ml, 9 pg/ml, or 10 pg/ml).

In some embodiments, the patient exhibits a serum concentration of β17-estradiol of less than 50 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example within about 8 days to about 15 days, of the first administration of the compound to the patient.

In some embodiments, the patient exhibits a serum concentration of β17-estradiol of less than 20 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example, within about 8 days to about 15 days, of the first administration of the compound to the patient.

In some embodiments, the patient exhibits a serum concentration of β17-estradiol of less than 10 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example, within about 8 days to about 15 days, of the first administration of the compound to the patient.

In some embodiments, the patient exhibits amenorrhea following administration of the compound to the patient. In some embodiments, the patient exhibits amenorrhea within about 2 weeks of the first administration of the compound to the patient, such as within about 3 days, 4 days, 5 days, 6 days, 7 days, 8 days, 9 days, 10 days, 11 days, 12 days, 13 days, or 14 days of the first administration of the compound to the patient. In some embodiments, the patient exhibits amenorrhea within about 1 week of the first administration of the compound to the patient, such as within about 3 days, 4 days, 5 days, 6 days, or 7 days of the first administration of the compound to the patient. In some embodiments, the amenorrhea is sustained for at least about 7 days, at least about 14 days, at least about 28 days, or more, such as for a period of from about 7 days to about 6 weeks, or longer (e.g., about 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, or more).

In some embodiments, the patient exhibits heavy menstrual bleeding prior to the initiation of treatment with the compound, such as daily treatment according to any of the aspects or embodiments of the invention described above or herein. The patient may exhibit, for example, menstrual blood loss of 80 ml or more (e.g., menstrual blood loss of 80 ml, 85 ml, 90 ml, 95 ml, 100 ml, 105 ml, 110 ml, 115 ml, 120 ml, 125 ml, or greater) per menstrual cycle prior to the initiation of treatment with the compound.

In some embodiments, the patient exhibits a reduced menstrual blood loss of less than 80 ml per menstrual cycle (e.g., 60 ml/menstrual cycle, 55 ml/menstrual cycle, 50 ml/menstrual cycle, 45 ml/menstrual cycle, 40 ml/menstrual cycle, 35 ml/menstrual cycle, or 30 ml/menstrual cycle) following administration of the compound to the patient. In some embodiments, the patient exhibits a reduced menstrual blood loss of less than 80 ml per menstrual cycle within about 2 weeks of the first administration of the compound to the patient, such as within about 3 days, 4 days, 5 days, 6 days, 7 days, 8 days, 9 days, 10 days, 11 days, 12 days, 13 days, or 14 days of the first administration of the compound to the patient. In some embodiments, the patient exhibits a reduced menstrual blood loss of less than 80 ml per menstrual cycle within about 1 week of the first administration of the compound to the patient, such as within about 3 days, 4 days, 5 days, 6 days, or 7 days of the first administration of the compound to the patient.

In some embodiments, the patient exhibits menstrual blood loss that is reduced by about 25% or more by volume per menstrual cycle, such as by about 25% to about 50% by volume per cycle, or more (e.g., menstrual blood loss that is reduced by 25%, 30%, 35%, 40%, 45%, or 50% by volume per menstrual cycle, or more) following administration of the compound to the patient relative to a measurement of the volume of menstrual blood loss exhibited by the patient prior to the initiation of treatment with the compound. In some embodiments, the patient exhibits menstrual blood loss that is reduced by about 25% or more by volume per menstrual cycle relative to a measurement of the volume of menstrual blood loss exhibited by the patient prior to the initiation of treatment with the compound, such as by about 25% to about 50% by volume per cycle, within about 2 weeks of the first administration of the compound to the patient, such as within about 3 days, 4 days, 5 days, 6 days, 7 days, 8 days, 9 days, 10 days, 11 days, 12 days, 13 days, or 14 days of the first administration of the compound to the patient. In some embodiments, the patient exhibits menstrual blood loss that is reduced by about 25% or more by volume per menstrual cycle relative to a measurement of the volume of menstrual blood loss exhibited by the patient prior to the initiation of treatment with the compound, such as by about 25% to about 50% by volume per cycle, within about 1 week of the first administration of the compound to the patient, such as within about 3 days, 4 days, 5 days, 6 days, or 7 days of the first administration of the compound to the patient.

In some embodiments, the patient exhibits a sustained low concentration of serum progesterone following administration of the compound to the patient. For instance, the patient may exhibit a sustained low concentration of serum progesterone for up to 12 days, 24, days, 36 days, 42 days, 48 days, 4 weeks, 8 weeks, 12 weeks, 24 weeks, 36 weeks, 48 weeks, 52 weeks, 64 weeks, or 76 weeks, or more (e.g., for from about 8 days to about 42 days, or more) following the first administration of the compound to the patient, such as for about 1 day, 2 consecutive days, 3 consecutive days, 4 consecutive days, 5 consecutive days, 6 consecutive days, 7 consecutive days, 8 consecutive days, 9 consecutive days, 10 consecutive days, 11 consecutive days, 12 consecutive days, 13 consecutive days, 14 consecutive days, 15 consecutive days, 16 consecutive days, 17 consecutive days, 18 consecutive days, 19 consecutive days, 20 consecutive days, 21 consecutive days, 22 consecutive days, 23 consecutive days, 24 consecutive days, 25 consecutive days, 26 consecutive days, 27 consecutive days, 28 consecutive days, 29 consecutive days, 30 consecutive days, 31 consecutive days, 32 consecutive days, 33 consecutive days, 34 consecutive days, 35 consecutive days, 36 consecutive days, 37 consecutive days, 38 consecutive days, 39 consecutive days, 40 consecutive days, 41 consecutive days, 42 consecutive days, or more, following the first administration of the compound to the patient. In some embodiments, the patient exhibits a serum progesterone concentration of from about 0.5 nM to about 0.7 nM following administration of the compound to the patient. For instance, the patient may exhibit a serum concentration of progesterone of 0.50 nM, 0.55 nM, 0.60 nM, 0.65 nM, or 0.70 nM following administration of the compound to the patient. As serum progesterone levels are positively correlated with ovulation, the GnRH antagonists described herein may therefore suppress ovulation in the patient, for instance, throughout the duration of a treatment cycle.

In some embodiments, the patient exhibits reduced pelvic pain following administration of the compound to the patient, for instance, as assessed using a Numerical Rating Score and/or a Verbal Rating Score as described herein.

In some embodiments, the patient exhibits reduced back pain following administration of the compound to the patient, for instance, as assessed using a Numerical Rating Score and/or a Verbal Rating Score as described herein.

In some embodiments, the patient does not exhibit a reduction in bone mineral density of greeter than 5% following administration of the compound to the patient. In some embodiments, the patient does not exhibit a reduction in bone mineral density of greeter than 1% following administration of the compound to the patient.

In some embodiments, the bone mineral density is assessed by dual energy X-ray absorptiometry, for instance, in the spine or femur of the patient.

In some embodiments, the bone mineral density is assessed by comparing the concentration of bone specific alkaline phosphatase (BAP) in a sample (e.g., a urine sample) isolated from the patient following the administration to the concentration of BAP in a sample (e.g., a urine sample) isolated from the patient prior to the administration.

In some embodiments, the bone mineral density is assessed by comparing the concentration of deoxypyridinoline (DPD) in a sample (e.g., a urine sample) isolated from the patient following the administration to the concentration of DPD in a sample (e.g., a urine sample) isolated from the patient prior to the administration.

In some embodiments, the bone mineral density is assessed by comparing the concentration of type I collagen C-terminal telopeptide (CTX) in a sample (e.g., a urine sample) isolated from the patient following the administration to the concentration of CTX in a sample (e.g., a urine sample) isolated from the patient prior to the administration.

In some embodiments, the bone mineral density is assessed by comparing the concentration of procollagen 1 N-terminal peptide (P1NP) in a sample (e.g., a urine sample) isolated from the patient following the administration to the concentration of P1NP in a sample (e.g., a urine sample) isolated from the patient prior to the administration.

In some embodiments, the compound (e.g., and add-back therapy) is administered to the patient daily (e.g., once daily and/or in any of the above-specified doses per day) for one or more treatment cycles. In some embodiments, the compound (e.g., and add-back therapy) is administered to the patient daily (e.g., once daily and/or in any of the above-specified doses per day) for one or more treatment cycles, each lasting for a period of about 4-72 weeks, or longer. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, or more.

In some embodiments, the compound (e.g., and add-back therapy) is administered to the patient for one or more treatment cycles, each lasting for a period of about 4-64 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, or 64 weeks.

In some embodiments, the compound (e.g., and add-back therapy) is administered to the patient for one or more treatment cycles, each lasting for a period of about 4-52 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks.

In some embodiments, the compound (e.g., and add-back therapy) is administered to the patient for one or more treatment cycles, each lasting for a period of about 4-48 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, or 48 weeks.

In some embodiments, the compound (e.g., and add-back therapy) is administered to the patient for one or more treatment cycles, each lasting for a period of about 4-24 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks.

In some embodiments, the compound (e.g., and add-back therapy) is administered to the patient for one or more treatment cycles, each lasting for a period of about 4-12 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, or 12 weeks.

In some embodiments, the compound (e.g., and add-back therapy) is administered to the patient for one or more treatment cycles (e.g., daily, such as once daily and/or in any of the above-specified doses per day), each treatment cycle lasting for a period of about 4 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 6 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 8 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 12 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 24 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 36 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 48 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 52 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 64 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 72 weeks.

In another aspect, the invention features a method of reducing the volume of menstrual blood loss in a patient (e.g., a human patient, such as a premenopausal female human patient), the method including administering to the patient the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I)

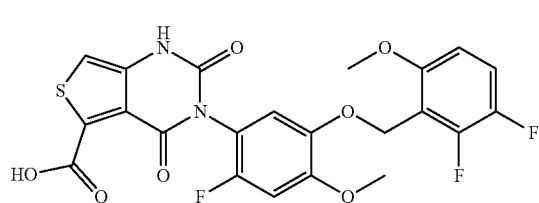

(I)

or a pharmaceutically acceptable salt thereof, in an amount of about 200 mg per dose.

In another aspect, the invention features a method of treating uterine fibroids in a patient (e.g., a human patient, such as a premenopausal female human patient), the method including administering to the patient the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I)

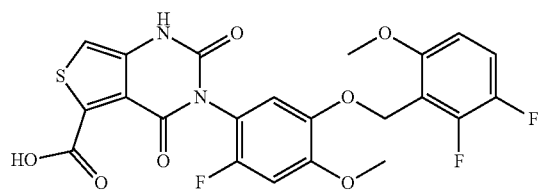

(I)

or a pharmaceutically acceptable salt thereof, in an amount of about 200 mg per dose.

In another aspect, the invention features a method of inducing amenorrhea in a patient (e.g., a human patient, such as a premenopausal female human patient, such as one that has uterine fibroids), the method including administering to the patient the GnRH antagonist 3-[2-fluoro-5-(2,3-difluoro-6-methoxybenzyloxy)-4-methoxyphenyl]-2,4-dioxo-1,2,3, 4-tetrahydrothieno [3,4d]pyrimidine-5-carboxylic acid, which is the compound represented by formula (I)

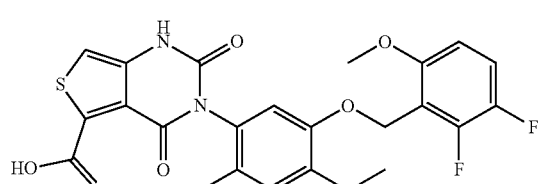

(I)

or a pharmaceutically acceptable salt thereof, in an amount of about 200 mg per dose.

In another aspect, the invention features a method of increasing the quantity and/or concentration of hemoglobin in the blood of a patient (e.g., a human patient, such as a premenopausal female human patient, such as one that has uterine fibroids), the method including administering to the patient the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I)

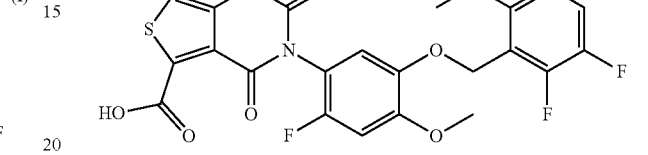

(I)

or a pharmaceutically acceptable salt thereof, in an amount of about 200 mg per dose.

In another aspect, the invention features a method of reducing the concentration of β17-estradiol, follicle-stimulating hormone (FSH), and/or luteinizing hormone (LH) in the blood of a patient (e.g., a human patient, such as a premenopausal female human patient, such as one that has uterine fibroids), the method including administering to the patient the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I)

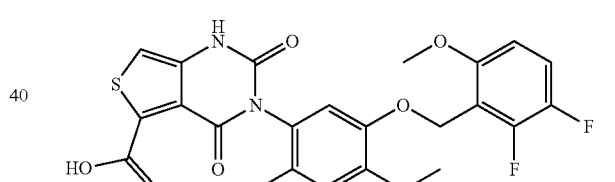

(I)

or a pharmaceutically acceptable salt thereof, in an amount of about 200 mg per dose.

In some embodiments of either of the previous aspects, the compound may be administered orally, for example, in the form of a tablet, capsule, gel cap, powder, liquid solution, or liquid suspension. The compound may be administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), or from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others.

In some embodiments, the compound is administered to the patient in an amount of about 200 mg/day (e.g., 200 mg/day). In some embodiments, the compound is administered to the patient in an amount of about 400 mg every 48 hours (e.g., 400 mg every 48 hours). In some embodiments, the compound is administered to the patient in an amount of about 600 mg every 72 hours (e.g., 600 mg every 72 hours). In some embodiments, the compound is administered to the patient in an amount of about 1,400 mg/week (e.g., 1,400 mg/week).

In some embodiments, the compound is administered to the patient in an amount of about 100 mg every 12 hours (e.g., 100 mg every 12 hours), in an amount of about 50 mg every 6 hours (e.g., 50 mg every 6 hours), in an amount of about 33.33 mg every 4 hours (e.g., 33.33 mg every 4 hours), in an amount of about 25 mg every 3 hours (e.g., 25 mg every 3 hours), or the like, e.g., so as to achieve an amount of 200 mg/day.

In some embodiments, the compound is the choline salt of the compound represented by formula (I), shown in formula (II), below.

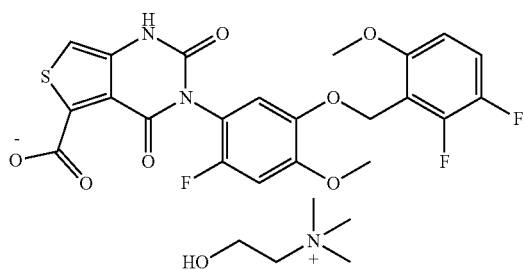

(II)

In some embodiments, the patient has uterine fibroids and the menstrual blood loss is associated with (e.g., caused by) the uterine fibroids. The patient may have anemia, such as an anemia associated with uterine fibroids. For instance, in some embodiments, the patient has iron deficiency anemia, for example, due to the heavy menstrual bleeding associated with uterine fibroids.

In some embodiments, the compound is in a crystalline state. The compound may exhibit characteristic X-ray powder diffraction peaks at about 7.1° 2θ, about 11.5° 2θ, about 19.4° 2θ, about 21.5° 2θ, about 22.0° 2θ, about 22.6° 2θ, about 23.5° 2θ, and about 26.2° 2θ. In some embodiments, the compound exhibits $^{13}C$ solid-state nuclear magnetic resonance (NMR) peaks centered at about 55.5 ppm, about 57.1 ppm, about 58.7 ppm, about 69.8 ppm, about 98.1 ppm, about 110.3 ppm, about 111.6 ppm, about 113.7 ppm, about 118.0 ppm, about 145.3 ppm, about 149.8 ppm, and about 155.8 ppm. The compound may exhibit $^{19}F$ solid-state NMR peaks centered at about −151.8 ppm, −145.2 ppm, and −131.6 ppm.

In some embodiments, the compound is orally administered to the patient. Other routes of administration that may be used in conjunction with the compositions and methods of the invention are described herein.

In some embodiments, the method includes administering add-back therapy to the patient. The add-back therapy may be administered to the patient concurrently with the GnRH antagonist, prior to administration of the GnRH antagonist, or following administration of the GnRH antagonist. In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of β17-estradiol, ethinyl estradiol, or a conjugated estrogen, such as a conjugated equine estrogen) and/or a progestin (e.g., norethindrone or a compound that is metabolized in vivo to produce norethindrone, such as an ester of norethindrone that is de-esterified in vivo to produce norethindrone, for instance, norethindrone acetate (also referred to herein as "NETA"), among other agents, such as progesterone, norgestimate, medroxyprogesterone, and drospirenone) in the form of a single pharmaceutical composition, such as a single tablet, capsule, gel cap, powder, liquid solution, or liquid suspension. In some embodiments, the add-back therapy is administered orally, transdermally, or intravaginally.

In some embodiments, the add-back therapy is administered to the patient in one or more doses per day, week, month, or year, such as daily, for example, from 1 to 10 times daily, or more (e.g., 1, 2, 3, 4, 5, 6, 7, 8, 9, 10, or more, times daily). In some embodiments, the add-back therapy is administered to the patient once daily, for example, concurrently with the GnRH antagonist. For example, the GnRH antagonist may be administered to the patient orally, and concurrently with oral administration of the GnRH antagonist, the add-back therapy may be administered to the patient orally, transdermally, or intravaginally. In some embodiments, the add-back therapy is administered to the patient in the form of a pharmaceutical composition that further includes the GnRH antagonist, such as a single tablet, capsule, gel cap, powder, liquid solution, or liquid suspension, for instance, as described above and herein.

In some embodiments, the add-back therapy is administered to the patient once daily, following administration of the compound. For example, the GnRH antagonist may be administered to the patient orally, and following oral administration of the GnRH antagonist, the add-back therapy may be administered to the patient orally, transdermally, or intravaginally.

In some embodiments, the add-back therapy is administered to the patient once daily, prior to administration of the compound. For example, the GnRH antagonist may be administered to the patient orally, and prior to oral administration of the GnRH antagonist, the add-back therapy may be administered to the patient orally, transdermally, or intravaginally.

In some embodiments, the add-back therapy includes an estrogen. In some embodiments, the estrogen is selected from the group consisting of β17-estradiol, ethinyl estradiol, and conjugated estrogens, such as conjugated equine estrogens.

In some embodiments, the estrogen is β17-estradiol. The β17-estradiol may be administered to the patient, for example, at a dose of from about 0.1 mg to about 2.5 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg, for instance, by oral administration. In some embodiments, the β17-estradiol is administered to the patient at a dose of 1.0 mg, for instance, by oral administration. In some embodiments, the β17-estradiol is administered to the patient at a dose of 0.5 mg, for instance, by oral administration.

The β17-estradiol may be administered to the patient one or more times per day, week, or month. The β17-estradiol may be administered to the patient, for example, at a dose of from about 0.1 mg/day to about 2.5 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, or 2.5 mg/day, for instance, by oral administration. In some embodiments, the β17-estradiol is administered to the patient at a dose of 1.0 mg/day, for instance, by oral administration. In some embodiments, the β17-estradiol is administered to the patient at a dose of 0.5 mg/day, for instance, by oral administration.

In some embodiments, the estrogen is ethinyl estradiol. The ethinyl estradiol may be administered to the patient, for example, at a dose of from about 1.0 µg to about 6.0 µg, such as at a dose of about 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, 3.0 µg, 3.1 µg, 3.2 µg, 3.3 µg, 3.4 µg, 3.5 µg, 3.6 µg, 3.7 µg, 3.8 µg, 3.9 µg, 4.0 µg, 4.1 µg, 4.2 µg, 4.2 µg, 4.3 µg, 4.4 µg, 4.5 µg, 4.6 µg, 4.7 µg, 4.8 µg, 4.9 µg, 5.0 µg, 5.1 µg, 5.2 µg, 5.3 µg, 5.4 µg, 5.5 µg, 5.6 µg, 5.7 µg, 5.8 µg, 5.9 µg, or 6.0 µg, for instance, by oral administration. In some embodiments, the ethinyl estradiol is administered to the patient at a dose of 5.0 µg, for instance, by oral administration. In some embodiments, the ethinyl estradiol is administered to the patient at a dose of 2.5 µg, for instance, by oral administration.

The ethinyl estradiol may be administered to the patient one or more times per day, week, or month. The ethinyl estradiol may be administered to the patient, for example, at a dose of from about 1.0 µg/day to about 6.0 µg/day, such as at a dose of about 1.0 µg/day, 1.1 µg/day, 1.2 µg/day, 1.3 µg/day, 1.4 µg/day, 1.5 µg/day, 1.6 µg/day, 1.7 µg/day, 1.8 µg/day, 1.9 µg/day, 2.0 µg/day, 2.1 µg/day, 2.2 µg/day, 2.3 µg/day, 2.4 µg/day, 2.5 µg/day, 2.6 µg/day, 2.7 µg/day, 2.8 µg/day, 2.9 µg/day, 3.0 µg/day, 3.1 µg/day, 3.2 µg/day, 3.3 µg/day, 3.4 µg/day, 3.5 µg/day, 3.6 µg/day, 3.7 µg/day, 3.8 µg/day, 3.9 µg/day, 4.0 µg/day, 4.1 µg/day, 4.2 µg/day, 4.2 µg/day, 4.3 µg/day, 4.4 µg/day, 4.5 µg/day, 4.6 µg/day, 4.7 µg/day, 4.8 µg/day, 4.9 µg/day, 5.0 µg/day, 5.1 µg/day, 5.2 µg/day, 5.3 µg/day, 5.4 µg/day, 5.5 µg/day, 5.6 µg/day, 5.7 µg/day, 5.8 µg/day, 5.9 µg/day, or 6.0 µg/day, for instance, by oral administration. In some embodiments, the ethinyl estradiol is administered to the patient at a dose of 5.0 µg/day, for instance, by oral administration. In some embodiments, the ethinyl estradiol is administered to the patient at a dose of 2.5 µg/day, for instance, by oral administration.

In some embodiments, the estrogen is a conjugated estrogen, such as a conjugated equine estrogen. The conjugated estrogen may be administered to the patient, for example, at a dose of from about 0.1 mg to about 2.0 mg, such as at a dose of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the conjugated estrogen is administered to the patient at a dose of 0.625 mg, for instance, by oral administration. In some embodiments, the conjugated estrogen is administered to the patient at a dose of 0.45 mg, for instance, by oral administration. In some embodiments, the conjugated estrogen is administered to the patient at a dose of 0.3 mg, for instance, by oral administration.

The conjugated estrogen may be administered to the patient one or more times per day, week, or month. The conjugated estrogen may be administered to the patient, for example, at a dose of from about 0.1 mg/day to about 2.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the conjugated estrogen is administered to the patient at a dose of 0.625 mg/day, for instance, by oral administration. In some embodiments, the conjugated estrogen is administered to the patient at a dose of 0.45 mg/day, for instance, by oral administration. In some embodiments, the conjugated estrogen is administered to the patient at a dose of 0.3 mg/day, for instance, by oral administration.

In some embodiments, the add-back therapy includes a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone is administered to the patient at a dose of 1.0 mg, for instance, by oral administration. In some embodiments, the norethindrone is administered to the patient at a dose of 0.5 mg, for instance, by oral administration. In some embodiments, the norethindrone is administered to the patient at a dose of 0.1 mg, for instance, by oral administration.

The norethindrone may be administered to the patient one or more times per day, week, or month. The norethindrone may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone is administered to the patient at a dose of 1.0 mg/day, for instance, by oral administration. In some embodiments, the norethindrone is administered to the patient at a dose of 0.5 mg/day, for instance, by oral administration. In some embodiments, the norethindrone is administered to the patient at a dose of 0.1 mg/day, for instance, by oral administration.

In some embodiments, the progestin is norethindrone acetate. The norethindrone acetate may be administered to the patient, for example, at a dose of from about 0.05 mg to about 5.0 mg, such as at a dose of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg, for instance, by oral administration. In some embodiments, the norethindrone acetate is administered to the patient at a dose of 0.1 mg, for instance, by oral administration.

The norethindrone acetate may be administered to the patient one or more times per day, week, or month. The norethindrone acetate may be administered to the patient, for example, at a dose of from about 0.05 mg/day to about 5.0 mg/day, such as at a dose of about 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, or 5.0 mg/day, for instance, by oral administration. In some embodiments, the norethindrone acetate is administered to the patient at a dose of 1.0 mg/day, for instance, by oral administration. In some embodiments, the norethindrone acetate is administered to the patient at a dose of 0.5 mg/day, for instance, by oral administration. In some embodiments, the norethindrone acetate is administered to the patient at a dose of 0.1 mg/day, for instance, by oral administration.

In some embodiments, the progestin is progesterone. The progesterone may be administered to the patient, for example, at a dose of from about 50 mg to about 250 mg, such as a dose of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg, for instance, by oral administration. In some embodiments, the progesterone is administered to the patient at a dose of 200 mg, for instance, by oral administration. In some embodiments, the progesterone is administered to the patient at a dose of 100 mg, for instance, by oral administration.

The progesterone may be administered to the patient one or more times per day, week, or month. The progesterone may be administered to the patient, for example, at a dose of from about 50 mg/day to about 250 mg/day, such as a dose of about 50 mg/day, 55 mg/day, 60 mg/day, 65 mg/day, 70 mg/day, 75 mg/day, 80 mg/day, 85 mg/day, 90 mg/day, 95 mg/day, 100 mg/day, 105 mg/day, 110 mg/day, 115 mg/day, 120 mg/day, 125 mg/day, 130 mg/day, 135 mg/day, 140 mg/day, 145 mg/day, 150 mg/day, 155 mg/day, 160 mg/day, 165 mg/day, 170 mg/day, 175 mg/day, 180 mg/day, 185 mg/day, 190 mg/day, 195 mg/day, 200 mg/day, 205 mg/day, 210 mg/day, 215 mg/day, 220 mg/day, 225 mg/day, 230 mg/day, 235 mg/day, 240 mg/day, 245 mg/day, or 250 mg/day, for instance, by oral administration. In some embodiments, the progesterone is administered to the patient at a dose of 200 mg/day, for instance, by oral administration. In some embodiments, the progesterone is administered to the patient at a dose of 100 mg/day, for instance, by oral administration.

In some embodiments, the progestin is norgestimate. The norgestimate may be administered to the patient, for example, at a dose of from about 0.01 mg to about 2.0 mg, such as at a dose of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg, for instance, by oral administration. In some embodiments, the norgestimate is administered to the patient at a dose of 0.09 mg, for instance, by oral administration.

The norgestimate may be administered to the patient one or more times per day, week, or month. The norgestimate may be administered to the patient, for example, at a dose of from about 0.01 mg/day to about 2.0 mg/day, such as at a dose of about 0.01 mg/day, 0.02 mg/day, 0.03 mg/day, 0.04 mg/day, 0.05 mg/day, 0.06 mg/day, 0.07 mg/day, 0.08 mg/day, 0.09 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, or 2.0 mg/day, for instance, by oral administration. In some embodiments, the norgestimate is administered to the patient at a dose of 0.09 mg/day, for instance, by oral administration.

In some embodiments, the progestin is medroxyprogesterone. The medroxyprogesterone may be administered to the patient, for example, at a dose of from about 0.5 mg to about 10.0 mg, such as at a dose of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg, for instance, by oral administration. In some embodiments, the medroxyprogesterone is administered to the patient at a dose of 5.0 mg, for instance, by oral administration. In some embodiments, the medroxyprogesterone is administered to the patient at a dose of 2.5 mg, for instance, by oral administration. In some embodiments, the medroxyprogesterone is administered to the patient at a dose of 1.5 mg, for instance, by oral administration.

The medroxyprogesterone may be administered to the patient one or more times per day, week, or month. The medroxyprogesterone may be administered to the patient, for example, at a dose of from about 0.5 mg/day to about 10.0 mg/day, such as at a dose of about 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, 3.0 mg/day, 3.1 mg/day, 3.2 mg/day, 3.3 mg/day, 3.4 mg/day, 3.5 mg/day, 3.6 mg/day, 3.7 mg/day, 3.8 mg/day, 3.9 mg/day, 4.0 mg/day, 4.1 mg/day, 4.2 mg/day, 4.3 mg/day, 4.4 mg/day, 4.5 mg/day, 4.6 mg/day, 4.7 mg/day, 4.8 mg/day, 4.9 mg/day, 5.0 mg/day, 5.1 mg/day, 5.2 mg/day, 5.3 mg/day, 5.4 mg/day, 5.5 mg/day, 5.6 mg/day, 5.7 mg/day, 5.8 mg/day, 5.9 mg/day, 6.0 mg/day, 6.1 mg/day, 6.2 mg/day, 6.3 mg/day, 6.4 mg/day, 6.5 mg/day, 6.6 mg/day, 6.7 mg/day, 6.8 mg/day, 6.9 mg/day, 7.0 mg/day, 7.1 mg/day, 7.2 mg/day, 7.3 mg/day, 7.4 mg/day, 7.5 mg/day, 7.6 mg/day, 7.7 mg/day, 7.8 mg/day, 7.9 mg/day, 8.0 mg/day, 8.1 mg/day, 8.2 mg/day, 8.3 mg/day, 8.4 mg/day, 8.5 mg/day, 8.6 mg/day, 8.7 mg/day, 8.8 mg/day, 8.9 mg/day, 9.0 mg/day, 9.1 mg/day, 9.2 mg/day, 9.3 mg/day, 9.4 mg/day, 9.5 mg/day, 9.6 mg/day, 9.7 mg/day, 9.8 mg/day, 9.9 mg/day, or 10.0 mg/day, for instance, by oral administration. In some embodiments, the medroxyprogesterone is administered to the patient at a dose of 5.0 mg/day, for instance, by oral administration. In some embodiments, the medroxyprogesterone is administered to the patient at a dose of 2.5 mg/day, for instance, by oral administration. In some embodiments, the medroxyprogesterone is administered to the patient at a dose of 1.5 mg/day, for instance, by oral administration.

In some embodiments, the progestin is drospirenone. The drospirenone may be administered to the patient, for example, at a dose of from about 0.1 mg to about 1.0 mg, such as at a dose of about 0.1 mg, 0.2 mg, 0.3 mg, 0.4 mg, 0.5 mg, 0.6 mg, 0.7 mg, 0.8 mg, 0.9 mg, or 1.0 mg, for instance, by oral administration. In some embodiments, the drospirenone is administered to the patient at a dose of 0.5 mg, for instance, by oral administration. In some embodiments, the drospirenone is administered to the patient at a dose of 0.25 mg, for instance, by oral administration.

The drospirenone may be administered to the patient one or more times per day, week, or month. The drospirenone may be administered to the patient, for example, at a dose of from about 0.1 mg/day to about 1.0 mg/day, such as at a dose of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, or 1.0 mg/day, for instance, by oral administration. In some embodiments, the drospirenone is administered to the patient at a dose of 0.5 mg/day, for instance, by oral administration. In some embodiments, the drospirenone is administered to the patient at a dose of 0.25 mg/day, for instance, by oral administration.

In some embodiments, the add-back therapy includes an estrogen and a progestin. In some embodiments, the add-back therapy includes β17-estradiol and norethindrone or a compound that is metabolized in vivo to produce norethindrone, such as an ester of norethindrone that is de-esterified in vivo to produce norethindrone, for instance, norethindrone acetate.

In some embodiments, the add-back therapy includes from about 0.75 mg to about 1.25 mg of β17-estradiol, e.g., administered orally, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and, in the same pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 1.0 mg of β17-estradiol, e.g., administered orally, and, in a separate pharmaceutical composition, 0.5 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the compound is administered to the patient in a fixed-dose composition that contains about 200 mg of the compound (e.g., 200 mg of the compound), from about 0.75 mg to about 1.25 mg of β17-estradiol, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate. In some embodiments, the compound is administered to the patient in a fixed-dose composition that contains about 200 mg of the compound (e.g., 200 mg of the compound), about 1.0 mg of β17-estradiol (e.g., 1.0 mg of β17-estradiol), and about 0.5 mg of norethindrone or a compound that is metabolized in vivo to produce norethindrone, such as an ester of norethindrone that is de-esterified in vivo to produce norethindrone, for instance, norethindrone acetate (e.g., 0.5 mg of norethindrone or a compound that is metabolized in vivo to produce norethindrone, such as an ester of norethindrone that is de-esterified in vivo to produce norethindrone, for instance, norethindrone acetate). In some embodiments, the compound is administered to the patient in a fixed-dose composition that contains 200 mg of the compound, 1.0 mg of β17-estradiol, and 0.5 mg of norethindrone acetate.

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), or from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the above fixed-dose composition is administered to the patient once daily.

In some embodiments, the add-back therapy includes from about 0.25 mg to about 0.75 mg of β17-estradiol, e.g., administered orally, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in the same pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally. In some embodiments, the add-back therapy includes 0.5 mg of β17-estradiol, e.g., administered orally, and, in a separate pharmaceutical composition, 0.1 mg of norethindrone or a compound that is metabolized in vivo to produce norethindrone, such as an ester of norethindrone that is de-esterified in vivo to produce norethindrone, for instance, norethindrone acetate, e.g., administered orally.

In some embodiments, the compound is administered to the patient in a fixed-dose composition that contains about 200 mg of the compound (e.g., 200 mg of the compound), from about 0.25 mg to about 0.75 mg of β17-estradiol, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate. In some embodiments, the compound is administered to the patient in a fixed-dose composition that contains about 200 mg of the compound (e.g., 200 mg of the compound), about 0.5 mg of β17-estradiol (e.g., 0.5 mg of β17-estradiol), and about 0.1 mg of norethindrone or a compound that is metabolized in vivo to produce norethindrone, such as an ester of norethindrone that is de-esterified in vivo to produce norethindrone, for instance, norethindrone acetate (e.g., 0.1 mg of norethindrone or a compound that is metabolized in vivo to produce norethindrone, such as an ester of norethindrone that is de-esterified in vivo to produce norethindrone, for instance, norethindrone acetate). In some embodiments, the compound is administered to the patient in a fixed-dose composition that contains 200 mg of the compound, 0.5 mg of β17-estradiol, and 0.1 mg of norethindrone acetate.

In some embodiments, the above fixed-dose composition is administered to the patient in one or more doses per 12 hours, 24 hours, 48 hours, 72 hours, week, month, or year, such as in from 1 to 10 doses per 12 hours (e.g., 1 dose every 12 hours, 2 doses every 12 hours, 3 doses every 12 hours, 4 doses every 12 hours, 5 doses every 12 hours, 6 doses every 12 hours, 7 doses every 12 hours, 8 doses every 12 hours, 9 doses every 12 hours, or 10 doses every 12 hours), from 1 to 10 doses per 24 hours (e.g., 1 dose every 24 hours, 2 doses every 24 hours, 3 doses every 24 hours, 4 doses every 24 hours, 5 doses every 24 hours, 6 doses every 24 hours, 7 doses every 24 hours, 8 doses every 24 hours, 9 doses every 24 hours, or 10 doses every 24 hours), from 1 to 10 doses per 48 hours (e.g., 1 dose every 48 hours, 2 doses every 48 hours, 3 doses every 48 hours, 4 doses every 48 hours, 5 doses every 48 hours, 6 doses every 48 hours, 7 doses every 48 hours, 8 doses every 48 hours, 9 doses every 48 hours, or 10 doses every 48 hours), from 1 to 10 doses per 72 hours (e.g., 1 dose every 72 hours, 2 doses every 72 hours, 3 doses every 72 hours, 4 doses every 72 hours, 5 doses every 72 hours, 6 doses every 72 hours, 7 doses every 72 hours, 8 doses every 72 hours, 9 doses every 72 hours, or 10 doses every 72 hours), from 1 to 10 doses per week (e.g., 1 dose every week, 2 doses every week, 3 doses every week, 4 doses every week, 5 doses every week, 6 doses every week, 7 doses every week, 8 doses every week, 9 doses every week, or 10 doses every week), from 1 to 60 doses per month (e.g., from 30-60 doses per month, such as 1 time daily, 2 times daily, 3 times daily, 4 times daily, 5 times daily, 6 times daily, 7 times daily, 8 times daily, 9 times daily, 10 times daily, 7 times weekly, 8 times weekly, 9 times weekly, 10 times weekly, 11 times weekly, 12 times weekly, 13 times weekly, 14 times weekly, or more), among others. In some embodiments, the fixed-dose composition is administered to the patient once daily.

In some embodiments, the patient exhibits a serum concentration of β17-estradiol that is greater than 20 μg/ml, greater than 30 μg/ml, greater than 40 μg/ml, or greater than 50 μg/ml prior to the administration of the compound to the patient. The serum concentration of β17-estradiol may be reduced to less than 50 μg/ml following administration of the compound to the patient. For instance, in some embodiments, the patient exhibits a serum concentration of β17-estradiol that is reduced to less than 50 pg/ml, less than 45 pg/ml, less than 40 pg/ml, less than 35 pg/ml, less than 30 pg/ml, less than 25 pg/ml, less than 20 pg/ml, less than 15 pg/ml, or less than 10 pg/ml following administration of the compound to the patient. In some embodiments, the patient exhibits a serum concentration of β17-estradiol that is reduced to less than 10 pg/ml to about 40 pg/ml, such as a serum concentration of β17-estradiol of 5 pg/ml, 10 pg/ml, 15 pg/ml, 20 pg/ml, 25 pg/ml, 30 pg/ml, 35 pg/ml, or 40 pg/ml. In some embodiments, the patient exhibits a serum concentration of β17-estradiol of from 5 pg/ml to 50 pg/ml following administration of the compound to the patient (e.g., a serum concentration of β17-estradiol of 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, 20 pg/ml, 21 pg/ml, 22 pg/ml, 23 pg/ml, 24 pg/ml, 25 pg/ml, 26 pg/ml, 27 pg/ml, 28 pg/ml, 29 pg/ml, 30 pg/ml, 31 pg/ml, 32 pg/ml, 33 pg/ml, 34 pg/ml, 35 pg/ml, 36 pg/ml, 37 pg/ml, 38 pg/ml, 39 pg/ml, 40 pg/ml, 41 pg/ml, 42 pg/ml, 43 pg/ml, 44 pg/ml, 45 pg/ml, 46 pg/ml, 47 pg/ml, 48 pg/ml, 49 pg/ml, or 50 pg/ml). In some embodiments, the patient exhibits a serum concentration of β17-estradiol of from 5 pg/ml to 20 pg/ml following administration of the compound to the patient (e.g., a serum concentration of β17-estradiol of 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, or 20 pg/ml). In some embodiments, the patient exhibits a serum concentration of β17-estradiol of from 5 pg/ml to 10 pg/ml following administration of the compound to the patient (e.g., a serum concentration of β17-estradiol of 5 pg/ml, 6 pg/ml, 7 pg/ml, 8 pg/ml, 9 pg/ml, or 10 pg/ml).

In some embodiments, the patient exhibits a serum concentration of β17-estradiol of less than 50 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example within about 8 days to about 15 days, of the first administration of the compound to the patient.

In some embodiments, the patient exhibits a serum concentration of β17-estradiol of less than 20 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example, within about 8 days to about 15 days, of the first administration of the compound to the patient.

In some embodiments, the patient exhibits a serum concentration of β17-estradiol of less than 10 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example, within about 8 days to about 15 days, of the first administration of the compound to the patient.

In some embodiments, the patient exhibits amenorrhea following administration of the compound to the patient. In some embodiments, the patient exhibits amenorrhea within about 2 weeks of the first administration of the compound to the patient, such as within about 3 days, 4 days, 5 days, 6 days, 7 days, 8 days, 9 days, 10 days, 11 days, 12 days, 13 days, or 14 days of the first administration of the compound to the patient. In some embodiments, the patient exhibits amenorrhea within about 1 week of the first administration of the compound to the patient, such as within about 3 days, 4 days, 5 days, 6 days, or 7 days of the first administration of the compound to the patient. In some embodiments, the amenorrhea is sustained for at least about 7 days, at least about 14 days, at least about 28 days, or more, such as for a period of from about 7 days to about 6 weeks, or longer (e.g., about 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, or more).

In some embodiments, the patient exhibits heavy menstrual bleeding prior to the initiation of treatment with the compound, such as daily treatment according to any of the aspects or embodiments of the invention described above or herein. The patient may exhibit, for example, menstrual blood loss of 80 ml or more (e.g., menstrual blood loss of 80 ml, 85 ml, 90 ml, 95 ml, 100 ml, 105 ml, 110 ml, 115 ml, 120 ml, 125 ml, or greater) per menstrual cycle prior to the initiation of treatment with the compound.

In some embodiments, the patient exhibits a reduced menstrual blood loss of less than 80 ml per menstrual cycle (e.g., 60 ml/menstrual cycle, 55 ml/menstrual cycle, 50 ml/menstrual cycle, 45 ml/menstrual cycle, 40 ml/menstrual cycle, 35 ml/menstrual cycle, or 30 ml/menstrual cycle) following administration of the compound to the patient. In some embodiments, the patient exhibits a reduced menstrual blood loss of less than 80 ml per menstrual cycle within about 2 weeks of the first administration of the compound to the patient, such as within about 3 days, 4 days, 5 days, 6 days, 7 days, 8 days, 9 days, 10 days, 11 days, 12 days, 13 days, or 14 days of the first administration of the compound to the patient. In some embodiments, the patient exhibits a reduced menstrual blood loss of less than 80 ml per menstrual cycle within about 1 week of the first administration of the compound to the patient, such as within about 3 days, 4 days, 5 days, 6 days, or 7 days of the first administration of the compound to the patient.

In some embodiments, the patient exhibits menstrual blood loss that is reduced by about 25% or more by volume per menstrual cycle, such as by about 25% to about 50% by volume per cycle, or more (e.g., menstrual blood loss that is reduced by 25%, 30%, 35%, 40%, 45%, or 50% by volume per menstrual cycle, or more) following administration of the compound to the patient relative to a measurement of the volume of menstrual blood loss exhibited by the patient prior to the initiation of treatment with the compound. In some embodiments, the patient exhibits menstrual blood loss that is reduced by about 25% or more by volume per menstrual cycle relative to a measurement of the volume of menstrual blood loss exhibited by the patient prior to the initiation of treatment with the compound, such as by about 25% to about 50% by volume per cycle, within about 2 weeks of the first administration of the compound to the patient, such as within about 3 days, 4 days, 5 days, 6 days, 7 days, 8 days, 9 days, 10 days, 11 days, 12 days, 13 days, or 14 days of the first administration of the compound to the patient. In some embodiments, the patient exhibits menstrual blood loss that is reduced by about 25% or more by volume per menstrual cycle relative to a measurement of the volume of menstrual blood loss exhibited by the patient prior to the initiation of treatment with the compound, such as by about 25% to about 50% by volume per cycle, within about 1 week of the first administration of the compound to the patient, such as within about 3 days, 4 days, 5 days, 6 days, or 7 days of the first administration of the compound to the patient.

In some embodiments, the patient exhibits a sustained low concentration of serum progesterone following administration of the compound to the patient. For instance, the patient may exhibit a sustained low concentration of serum progesterone for up to 12 days, 24, days, 36 days, 42 days, 48 days, 4 weeks, 8 weeks, 12 weeks, 24 weeks, 36 weeks, 48 weeks, 52 weeks, 64 weeks, or 76 weeks, or more (e.g., for from about 8 days to about 42 days, or more) following the first administration of the compound to the patient, such as for about 1 day, 2 consecutive days, 3 consecutive days, 4 consecutive days, 5 consecutive days, 6 consecutive days, 7 consecutive days, 8 consecutive days, 9 consecutive days, 10 consecutive days, 11 consecutive days, 12 consecutive days, 13 consecutive days, 14 consecutive days, 15 consecutive days, 16 consecutive days, 17 consecutive days, 18 consecutive days, 19 consecutive days, 20 consecutive days, 21 consecutive days, 22 consecutive days, 23 consecutive days, 24 consecutive days, 25 consecutive days, 26 consecutive days, 27 consecutive days, 28 consecutive days, 29 consecutive days, 30 consecutive days, 31 consecutive days, 32 consecutive days, 33 consecutive days, 34 consecutive days, 35 consecutive days, 36 consecutive days, 37 consecutive days, 38 consecutive days, 39 consecutive days, 40 consecutive days, 41 consecutive days, 42 consecutive days, or more, following the first administration of the compound to the patient. In some embodiments, the patient exhibits a serum progesterone concentration of from about 0.5 nM to about 0.7 nM following administration of the compound to the patient. For instance, the patient may exhibit a serum concentration of progesterone of 0.50 nM, 0.55 nM, 0.60 nM, 0.65 nM, or 0.70 nM following administration of the compound to the patient. As serum progesterone levels are positively correlated with ovulation, the GnRH antagonists described herein may therefore suppress ovulation in the patient, for instance, throughout the duration of a treatment cycle.

In some embodiments, the patient exhibits reduced pelvic pain following administration of the compound to the patient, for instance, as assessed using a Numerical Rating Score and/or a Verbal Rating Score as described herein.

In some embodiments, the patient exhibits reduced back pain following administration of the compound to the patient, for instance, as assessed using a Numerical Rating Score and/or a Verbal Rating Score as described herein.

In some embodiments, the patient does not exhibit a reduction in bone mineral density of greeter than 5% following administration of the compound to the patient. In some embodiments, the patient does not exhibit a reduction in bone mineral density of greeter than 1% following administration of the compound to the patient.

In some embodiments, the bone mineral density is assessed by dual energy X-ray absorptiometry, for instance, in the spine or femur of the patient.

In some embodiments, the bone mineral density is assessed by comparing the concentration of BAP in a sample (e.g., a urine sample) isolated from the patient following the administration to the concentration of BAP in a sample (e.g., a urine sample) isolated from the patient prior to the administration.

In some embodiments, the bone mineral density is assessed by comparing the concentration of DPD in a sample (e.g., a urine sample) isolated from the patient following the administration to the concentration of DPD in a sample (e.g., a urine sample) isolated from the patient prior to the administration.

In some embodiments, the bone mineral density is assessed by comparing the concentration of CTX in a sample (e.g., a urine sample) isolated from the patient following the administration to the concentration of CTX in a sample (e.g., a urine sample) isolated from the patient prior to the administration.

In some embodiments, the bone mineral density is assessed by comparing the concentration of P1 NP in a sample (e.g., a urine sample) isolated from the patient following the administration to the concentration of P1 NP in a sample (e.g., a urine sample) isolated from the patient prior to the administration.

In some embodiments, the compound (e.g., and add-back therapy) is administered to the patient daily (e.g., once daily and/or in any of the above-specified doses per day) for one or more treatment cycles. In some embodiments, the compound (e.g., and add-back therapy) is administered to the patient daily (e.g., once daily and/or in any of the above-specified doses per day) for one or more treatment cycles, each lasting for a period of about 4-72 weeks, or longer. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, or more.

In some embodiments, the compound (e.g., and add-back therapy) is administered to the patient for one or more treatment cycles, each lasting for a period of about 4-64 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, or 64 weeks.

In some embodiments, the compound (e.g., and add-back therapy) is administered to the patient for one or more treatment cycles, each lasting for a period of about 4-52 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks.

In some embodiments, the compound (e.g., and add-back therapy) is administered to the patient for one or more treatment cycles, each lasting for a period of about 4-48 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, or 48 weeks.

In some embodiments, the compound (e.g., and add-back therapy) is administered to the patient for one or more treatment cycles, each lasting for a period of about 4-24 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks.

In some embodiments, the compound (e.g., and add-back therapy) is administered to the patient for one or more treatment cycles, each lasting for a period of about 4-12 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, or 12 weeks.

In some embodiments, the compound (e.g., and add-back therapy) is administered to the patient for one or more treatment cycles (e.g., daily, such as once daily and/or in any of the above-specified doses per day), each treatment cycle lasting for a period of about 4 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 6 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 8 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 12 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 24 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 36 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 48 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 52 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 64 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 72 weeks.

In yet another aspect, the invention features a method of reducing the volume of menstrual blood loss in a patient, such as a human patient (e.g., a premenopausal female human patient), such as one that has uterine fibroids, by administering to the patient a therapeutically effective amount of a compound represented by formula (I),

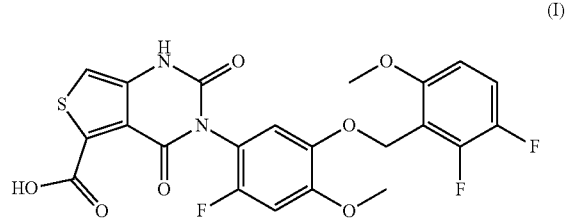 [SMILES: COc1cc(F)c(-n2c(=O)[nH]c3csc(C(=O)O)c3c2=O)cc1OCc1c(OC)ccc(F)c1F]

(I)

or a pharmaceutically acceptable salt thereof, in combination with add-back therapy. The add-back therapy may be administered in an amount sufficient to prevent bone mineral density loss, such as a loss of bone mineral density in excess of 5% (e.g., so as to prevent bone mineral density loss in excess of 1%).

In an additional aspect, the invention features a method of treating uterine fibroids in a patient, such as a human patient (e.g., a premenopausal female human patient), by administering to the patient a therapeutically effective amount of the GnRH antagonist 3-[2-fluoro-5-(2,3-difluoro-6-methoxybenzyloxy)-4-methoxyphenyl]-2,4-dioxo-1,2,3,4-tetrahydrothieno[3,4d]pyrimidine-5-carboxylic acid, which is the compound represented by formula (I),

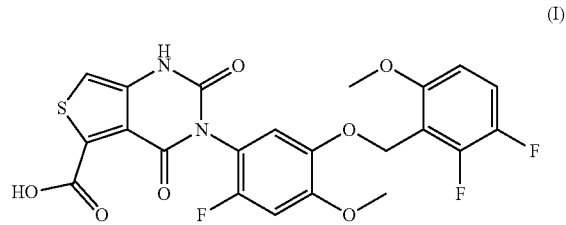 [SMILES: COc1cc(F)c(-n2c(=O)[nH]c3csc(C(=O)O)c3c2=O)cc1OCc1c(OC)ccc(F)c1F]

(I)

or a pharmaceutically acceptable salt thereof, in combination with add-back therapy. The add-back therapy may be administered in an amount sufficient to prevent bone mineral density loss, such as a loss of bone mineral density in excess of 5% (e.g., so as to prevent bone mineral density loss in excess of 1%).

In yet another aspect, the invention features a method of inducing amenorrhea in a patient, such as a human patient (e.g., a premenopausal female human patient), such as one that has uterine fibroids, by administering to the patient a therapeutically effective amount of a compound represented by formula (I),

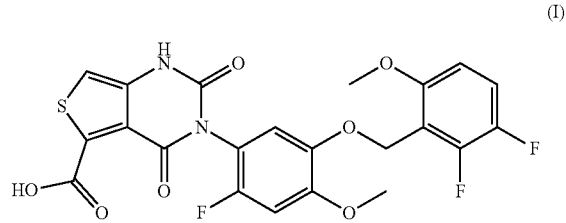 [SMILES: COc1cc(F)c(-n2c(=O)[nH]c3csc(C(=O)O)c3c2=O)cc1OCc1c(OC)ccc(F)c1F]

(I)

or a pharmaceutically acceptable salt thereof, in combination with add-back therapy. The add-back therapy may be administered in an amount sufficient to prevent bone mineral density loss, such as a loss of bone mineral density in excess of 5% (e.g., so as to prevent bone mineral density loss in excess of 1%).

In an additional aspect, the invention features a method of increasing the quantity and/or concentration of hemoglobin in the blood of a patient, such as a human patient (e.g., a premenopausal female human patient), by administering to the patient a therapeutically effective amount of the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I),

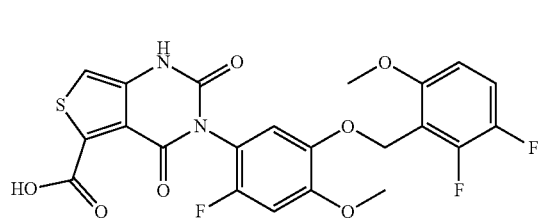

(I)

or a pharmaceutically acceptable salt thereof, in combination with add-back therapy. The add-back therapy may be administered in an amount sufficient to prevent bone mineral density loss, such as a loss of bone mineral density in excess of 5% (e.g., so as to prevent bone mineral density loss in excess of 1%).

In another aspect, the invention features a method of reducing the concentration of β17-estradiol, follicle-stimulating hormone (FSH), and/or luteinizing hormone (LH) in the blood of a patient (e.g., a human patient, such as a premenopausal female human patient, such as one that has uterine fibroids), by administering to the patient a therapeutically effective amount of the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, which is the compound represented by formula (I),

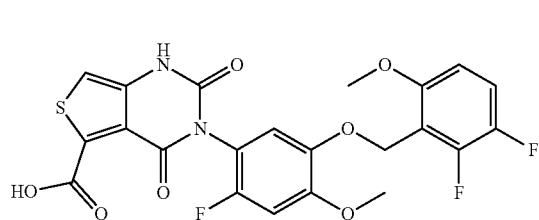

(I)

or a pharmaceutically acceptable salt thereof, in combination with add-back therapy. The add-back therapy may be administered in an amount sufficient to prevent bone mineral density loss, such as a loss of bone mineral density in excess of 5% (e.g., so as to prevent bone mineral density loss in excess of 1%).

In some embodiments of any of the foregoing aspects, the add-back therapy contains an estrogen. The estrogen may be, for example, from about 0.1 mg to about 2.5 mg of β17-estradiol, such as about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg of β17-estradiol. In some embodiments, the add-back therapy contains about 1.0 mg of β17-estradiol. In some embodiments, the add-back therapy contains about 0.5 mg of β17-estradiol.

In some embodiments, the add-back therapy contains ethinyl estradiol, such as in an amount of, for example, from about 1.0 µg to about 6.0 µg, such as about 1.0 µg, 1.1 µg, 1.2 µg, 1.3 µg, 1.4 µg, 1.5 µg, 1.6 µg, 1.7 µg, 1.8 µg, 1.9 µg, 2.0 µg, 2.1 µg, 2.2 µg, 2.3 µg, 2.4 µg, 2.5 µg, 2.6 µg, 2.7 µg, 2.8 µg, 2.9 µg, 3.0 µg, 3.1 µg, 3.2 µg, 3.3 µg, 3.4 µg, 3.5 µg, 3.6 µg, 3.7 µg, 3.8 µg, 3.9 µg, 4.0 µg, 4.1 µg, 4.2 µg, 4.2 µg, 4.3 µg, 4.4 µg, 4.5 µg, 4.6 µg, 4.7 µg, 4.8 µg, 4.9 µg, 5.0 µg, 5.1 µg, 5.2 µg, 5.3 µg, 5.4 µg, 5.5 µg, 5.6 µg, 5.7 µg, 5.8 µg, 5.9 µg, or 6.0 µg of ethinyl estradiol. In some embodiments, the add-back therapy contains about 5.0 µg of ethinyl estradiol. In some embodiments, the add-back therapy contains about 2.5 µg of ethinyl estradiol.

In some embodiments, the add-back therapy contains a conjugated equine estrogen, such as in an amount of, for example, from about 0.1 mg to about 2.0 mg, such as about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg of a conjugated equine estrogen. In some embodiments, the add-back therapy contains about 0.625 mg of a conjugated equine estrogen. In some embodiments, the add-back therapy contains about 0.45 mg of a conjugated equine estrogen. In some embodiments, the add-back therapy contains about 0.3 mg of a conjugated equine estrogen.

In some embodiments, the add-back therapy contains a progestin. For example, the add-back therapy may contain from about 0.05 mg to about 5.0 mg of norethindrone or a compound that is metabolized in vivo to produce norethindrone, such as an ester of norethindrone that is de-esterified in vivo to produce norethindrone, for instance, norethindrone acetate. For example, the add-back therapy may contain about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg of norethindrone or a compound that is metabolized in vivo to produce norethindrone, such as an ester of norethindrone that is de-esterified in vivo to produce norethindrone, for instance, norethindrone acetate. In some embodiments, the add-back therapy contains about 0.5 mg of norethindrone or a compound that is metabolized in vivo to produce norethindrone, such as an ester of norethindrone that is de-esterified in vivo to produce norethindrone, for instance, norethindrone acetate. In some embodiments, the add-back therapy contains about 0.1 mg of norethindrone or a compound that is metabolized in vivo to produce norethindrone, such as an ester of norethindrone that is de-esterified in vivo to produce norethindrone, for instance, norethindrone acetate.

In some embodiments, the add-back therapy contains progesterone, such as in an amount of, for example, from about 50 mg to about 250 mg, such as about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg of progesterone. In some embodiments, the add-back therapy contains about 200 mg of progesterone. In some embodiments, the add-back therapy contains about 100 mg of progesterone.

In some embodiments, the add-back therapy contains norgestimate, such as in an amount of, for example, from about 0.01 mg to about 2.0 mg, such as about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg of norgestimate. In some embodiments, the add-back therapy contains about 0.09 mg of norgestimate.

In some embodiments, the add-back therapy contains medroxyprogesterone, such as in an amount of, for example, from about 0.5 mg to about 10.0 mg, such as about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg of medroxyprogesterone. In some embodiments, the add-back therapy contains about 5.0 mg of medroxyprogesterone. In some embodiments, the add-back therapy contains about 2.5 mg of medroxyprogesterone. In some embodiments, the add-back therapy contains about 1.5 mg of medroxyprogesterone.

In some embodiments, the add-back therapy contains drospirenone, such as in an amount of, for example, from about 0.1 mg to about 1.0 mg, such as about 0.1 mg, 0.2 mg, 0.3 mg, 0.4 mg, 0.5 mg, 0.6 mg, 0.7 mg, 0.8 mg, 0.9 mg, or 1.0 mg of drospirenone. In some embodiments, the add-back therapy contains about 0.5 mg of drospirenone. In some embodiments, the add-back therapy contains about 0.25 mg of drospirenone.

In some embodiments, the add-back therapy contains from about 0.75 mg to about 1.25 mg of β17-estradiol, and from about 0.25 mg to about 0.75 mg of norethindrone or a compound that is metabolized in vivo to produce norethindrone, such as an ester of norethindrone that is de-esterified in vivo to produce norethindrone, for instance, norethindrone acetate. In some embodiments, the add-back therapy contains about 1.0 mg of β17-estradiol and about 0.5 mg of norethindrone or a compound that is metabolized in vivo to produce norethindrone, such as an ester of norethindrone that is de-esterified in vivo to produce norethindrone, for instance, norethindrone acetate.

In some embodiments, the add-back therapy contains from about 0.25 mg to about 0.75 mg of β17-estradiol, and from about 0.05 mg to about 0.2 mg of norethindrone or a compound that is metabolized in vivo to produce norethindrone, such as an ester of norethindrone that is de-esterified in vivo to produce norethindrone, for instance, norethindrone acetate. In some embodiments, the add-back therapy contains about 0.5 mg of β17-estradiol and about 0.1 mg of norethindrone or a compound that is metabolized in vivo to produce norethindrone, such as an ester of norethindrone that is de-esterified in vivo to produce norethindrone, for instance, norethindrone acetate.

In some embodiments, the compound is the choline salt of the compound represented by formula (I), shown in formula (II), below.

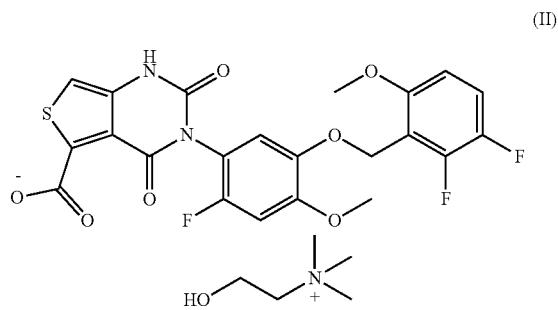

(II)

In some embodiments, the patient has anemia, such as an anemia associated with uterine fibroids. For instance, in some embodiments, the patient has iron deficiency anemia, for example, due to the heavy menstrual bleeding associated with uterine fibroids.

In some embodiments, the compound is in a crystalline state. The compound may exhibit characteristic X-ray powder diffraction peaks at about 7.1° 2θ, about 11.5° 2θ, about 19.4° 2θ, about 21.5° 2θ, about 22.0° 2θ, about 22.6° 2θ, about 23.5° 2θ, and about 26.2° 2θ. In some embodiments, the compound exhibits $^{13}C$ solid-state nuclear magnetic resonance (NMR) peaks centered at about 55.5 ppm, about 57.1 ppm, about 58.7 ppm, about 69.8 ppm, about 98.1 ppm, about 110.3 ppm, about 111.6 ppm, about 113.7 ppm, about 118.0 ppm, about 145.3 ppm, about 149.8 ppm, and about 155.8 ppm. The compound may exhibit $^{19}F$ solid-state NMR peaks centered at about −151.8 ppm, −145.2 ppm, and −131.6 ppm.

In some embodiments, the compound is orally administered to the patient, for example, in an amount of from about 100 mg per dose to about 200 mg per dose (e.g., about 100 mg per dose or about 200 mg per dose). Other routes of administration that may be used in conjunction with the compositions and methods of the invention are described herein. The compound may be administered to the patient one or more times per day, week, or month (e.g., 1, 2, 3, 4, 5, 6, 7, 8, 9, 10, or more times per day, week, or month). In some embodiments, the compound is administered to the patient in an amount of about 100 mg/day or about 200 mg/day.

In some embodiments, the compound is administered to the patient in an amount of about 50 mg every 12 hours (e.g., 50 mg every 12 hours), in an amount of about 25 mg every 6 hours (e.g., 25 mg every 6 hours), in an amount of about 16.67 mg every 4 hours (e.g., 16.67 mg every 4 hours), in an amount of about 12.5 mg every 3 hours (e.g., 12.5 mg every 3 hours), or the like, e.g., so as to achieve an amount of 100 mg/day.

In some embodiments, the compound is administered to the patient in an amount of about 100 mg/day (e.g., 100 mg/day). In some embodiments, the compound is administered to the patient in an amount of about 200 mg every 48 hours (e.g., 200 mg every 48 hours). In some embodiments, the compound is administered to the patient in an amount of about 300 mg every 72 hours (e.g., 300 mg every 72 hours). In some embodiments, the compound is administered to the patient in an amount of about 700 mg/week (e.g., 700 mg/week).

In some embodiments, the compound is administered to the patient in an amount of about 100 mg every 12 hours (e.g., 100 mg every 12 hours), in an amount of about 50 mg every 6 hours (e.g., 50 mg every 6 hours), in an amount of about 33.33 mg every 4 hours (e.g., 33.33 mg every 4 hours), in an amount of about 25 mg every 3 hours (e.g., 25 mg every 3 hours), or the like, e.g., so as to achieve an amount of 200 mg/day.

In some embodiments, the compound is administered to the patient in an amount of about 200 mg/day (e.g., 200 mg/day). In some embodiments, the compound is administered to the patient in an amount of about 400 mg every 48 hours (e.g., 400 mg every 48 hours). In some embodiments, the compound is administered to the patient in an amount of about 600 mg every 72 hours (e.g., 600 mg every 72 hours). In some embodiments, the compound is administered to the patient in an amount of about 1,400 mg/week (e.g., 1,400 mg/week).

The compound may be administered to the patient, for example, in the form of a tablet, capsule, gel cap, powder, liquid solution, or liquid suspension.

In some embodiments, the add-back therapy is administered to the patient daily, such as 1, 2, 3, 4, or more times daily. In some embodiments, the add-back therapy is administered to the patient once daily, for example, concurrently with the GnRH antagonist. For example, the GnRH antagonist may be administered to the patient orally, and concurrently with oral administration of the GnRH antagonist, the add-back therapy may be administered to the patient orally, transdermally, or intravaginally. In some embodiments, the add-back therapy is administered to the patient in the form of a pharmaceutical composition that further includes the GnRH antagonist, such as a single tablet, capsule, gel cap, powder, liquid solution, or liquid suspension, for instance, as described herein.

In some embodiments, the add-back therapy is administered to the patient daily, such as 1, 2, 3, 4, or more times daily (e.g., once daily), following administration of the GnRH antagonist. For example, the GnRH antagonist may be administered to the patient orally, and following oral administration of the GnRH antagonist, the add-back therapy may be administered to the patient orally, transdermally, or intravaginally.

In some embodiments, the add-back therapy is administered to the patient daily, such as 1, 2, 3, 4, or more times daily (e.g., once daily), prior to administration of the compound. For example, the GnRH antagonist may be administered to the patient orally, and prior to oral administration of the GnRH antagonist, the add-back therapy may be administered to the patient orally, transdermally, or intravaginally.

In some embodiments, the patient exhibits a serum concentration of $\beta$17-estradiol that is reduced to less than 50 pg/ml following administration of the compound to the patient. For instance, in some embodiments, the patient exhibits a serum concentration of $\beta$17-estradiol that is reduced to less than 50 pg/ml, less than 45 pg/ml, less than 40 pg/ml, less than 35 pg/ml, less than 30 pg/ml, less than 25 pg/ml, less than 20 pg/ml, less than 15 pg/ml, or less than 10 pg/ml following administration of the compound to the patient. In some embodiments, the patient exhibits a serum concentration of $\beta$17-estradiol that is reduced to less than 10 pg/ml to about 40 pg/ml, such as a serum concentration of $\beta$17-estradiol of 5 pg/ml, 10 pg/ml, 15 pg/ml, 20 pg/ml, 25 pg/ml, 30 pg/ml, 35 pg/ml, or 40 pg/ml. In some embodiments, the patient exhibits a serum concentration of $\beta$17-estradiol of from 5 pg/ml to 50 pg/ml following administration of the compound to the patient (e.g., a serum concentration of $\beta$17-estradiol of 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, 20 pg/ml, 21 pg/ml, 22 pg/ml, 23 pg/ml, 24 pg/ml, 25 pg/ml, 26 pg/ml, 27 pg/ml, 28 pg/ml, 29 pg/ml, 30 pg/ml, 31 pg/ml, 32 pg/ml, 33 pg/ml, 34 pg/ml, 35 pg/ml, 36 pg/ml, 37 pg/ml, 38 pg/ml, 39 pg/ml, 40 pg/ml, 41 pg/ml, 42 pg/ml, 43 pg/ml, 44 pg/ml, 45 pg/ml, 46 pg/ml, 47 pg/ml, 48 pg/ml, 49 pg/ml, or 50 pg/ml). In some embodiments, the patient exhibits a serum concentration of $\beta$17-estradiol of from 5 pg/ml to 20 pg/ml following administration of the compound to the patient (e.g., a serum concentration of $\beta$17-estradiol of 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 16 pg/ml, 17 pg/ml, 18 pg/ml, 19 pg/ml, or 20 pg/ml). In some embodiments, the patient exhibits a serum concentration of $\beta$17-estradiol of from 5 pg/ml to 10 pg/ml following administration of the compound to the patient (e.g., a serum concentration of $\beta$17-estradiol of 5 pg/ml, 6 pg/ml, 7 pg/ml, 8 pg/ml, 9 pg/ml, or 10 pg/ml).

In some embodiments, the patient exhibits a serum concentration of $\beta$17-estradiol of less than 50 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example within about 8 days to about 15 days, of the first administration of the compound to the patient.

In some embodiments, the patient exhibits a serum concentration of $\beta$17-estradiol of less than 20 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example, within about 8 days to about 15 days, of the first administration of the compound to the patient.

In some embodiments, the patient exhibits a serum concentration of $\beta$17-estradiol of less than 10 pg/ml, or within one of the ranges specified above, within about 1 to about 22 days of the first administration of the compound to the patient, such as within about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 22 days, for example, within about 8 days to about 15 days, of the first administration of the compound to the patient.

In some embodiments, the patient exhibits amenorrhea following administration of the compound to the patient. In some embodiments, the patient exhibits amenorrhea within about 2 weeks of the first administration of the compound to the patient, such as within about 3 days, 4 days, 5 days, 6 days, 7 days, 8 days, 9 days, 10 days, 11 days, 12 days, 13 days, or 14 days of the first administration of the compound to the patient. In some embodiments, the patient exhibits amenorrhea within about 1 week of the first administration of the compound to the patient, such as within about 3 days, 4 days, 5 days, 6 days, or 7 days of the first administration of the compound to the patient. In some embodiments, the amenorrhea is sustained for at least about 7 days, at least about 14 days, at least about 28 days, or more, such as for a period of from about 7 days to about 6 weeks, or longer (e.g., about 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, or more).

In some embodiments, the patient exhibits heavy menstrual bleeding prior to the initiation of treatment with the compound, such as daily treatment according to any of the aspects or embodiments of the invention described above or herein. The patient may exhibit, for example, menstrual blood loss of 80 ml or more (e.g., menstrual blood loss of 80 ml, 85 ml, 90 ml, 95 ml, 100 ml, 105 ml, 110 ml, 115 ml, 120 ml, 125 ml, or greater) per menstrual cycle prior to the initiation of treatment with the compound.

In some embodiments, the patient exhibits a reduced menstrual blood loss of less than 80 ml per menstrual cycle (e.g., 60 ml/menstrual cycle, 55 ml/menstrual cycle, 50 ml/menstrual cycle, 45 ml/menstrual cycle, 40 ml/menstrual cycle, 35 ml/menstrual cycle, or 30 ml/menstrual cycle) following administration of the compound to the patient. In some embodiments, the patient exhibits a reduced menstrual blood loss of less than 80 ml per menstrual cycle within about 2 weeks of the first administration of the compound to the patient, such as within about 3 days, 4 days, 5 days, 6 days, 7 days, 8 days, 9 days, 10 days, 11 days, 12 days, 13 days, or 14 days of the first administration of the compound to the patient. In some embodiments, the patient exhibits a reduced menstrual blood loss of less than 80 ml per menstrual cycle within about 1 week of the first administration of the compound to the patient, such as within about 3 days, 4 days, 5 days, 6 days, or 7 days of the first administration of the compound to the patient.

In some embodiments, the patient exhibits menstrual blood loss that is reduced by about 25% or more by volume per menstrual cycle, such as by about 25% to about 50% by volume per cycle, or more (e.g., menstrual blood loss that is reduced by 25%, 30%, 35%, 40%, 45%, or 50% by volume per menstrual cycle, or more) following administration of the compound to the patient relative to a measurement of the volume of menstrual blood loss exhibited by the patient prior to the initiation of treatment with the compound. In some embodiments, the patient exhibits menstrual blood loss that is reduced by about 25% or more by volume per menstrual cycle relative to a measurement of the volume of menstrual blood loss exhibited by the patient prior to the initiation of treatment with the compound, such as by about 25% to about 50% by volume per cycle, within about 2 weeks of the first administration of the compound to the patient, such as within about 3 days, 4 days, 5 days, 6 days, 7 days, 8 days, 9 days, 10 days, 11 days, 12 days, 13 days, or 14 days of the first administration of the compound to the patient. In some embodiments, the patient exhibits menstrual blood loss that is reduced by about 25% or more by volume per menstrual cycle relative to a measurement of the volume of menstrual blood loss exhibited by the patient prior to the initiation of treatment with the compound, such as by about 25% to about 50% by volume per cycle, within about 1 week of the first administration of the compound to the patient, such as within about 3 days, 4 days, 5 days, 6 days, or 7 days of the first administration of the compound to the patient.

In some embodiments, the patient exhibits a sustained low concentration of serum progesterone following administration of the compound to the patient. For instance, the patient may exhibit a sustained low concentration of serum progesterone for up to 12 days, 24, days, 36 days, 42 days, 48 days, 4 weeks, 8 weeks, 12 weeks, 24 weeks, 36 weeks, 48 weeks, 52 weeks, 64 weeks, or 76 weeks, or more (e.g., for from about 8 days to about 42 days, or more) following the first administration of the compound to the patient, such as for about 1 day, 2 consecutive days, 3 consecutive days, 4 consecutive days, 5 consecutive days, 6 consecutive days, 7 consecutive days, 8 consecutive days, 9 consecutive days, 10 consecutive days, 11 consecutive days, 12 consecutive days, 13 consecutive days, 14 consecutive days, 15 consecutive days, 16 consecutive days, 17 consecutive days, 18 consecutive days, 19 consecutive days, 20 consecutive days, 21 consecutive days, 22 consecutive days, 23 consecutive days, 24 consecutive days, 25 consecutive days, 26 consecutive days, 27 consecutive days, 28 consecutive days, 29 consecutive days, 30 consecutive days, 31 consecutive days, 32 consecutive days, 33 consecutive days, 34 consecutive days, 35 consecutive days, 36 consecutive days, 37 consecutive days, 38 consecutive days, 39 consecutive days, 40 consecutive days, 41 consecutive days, 42 consecutive days, or more, following the first administration of the compound to the patient. In some embodiments, the patient exhibits a serum progesterone concentration of from about 0.5 nM to about 0.7 nM following administration of the compound to the patient. For instance, the patient may exhibit a serum concentration of progesterone of 0.50 nM, 0.55 nM, 0.60 nM, 0.65 nM, or 0.70 nM following administration of the compound to the patient. As serum progesterone levels are positively correlated with ovulation, the GnRH antagonists described herein may therefore suppress ovulation in the patient, for instance, throughout the duration of a treatment cycle.

In some embodiments, the patient exhibits reduced pelvic pain following administration of the compound to the patient, for instance, as assessed using a Numerical Rating Score and/or a Verbal Rating Score as described herein.

In some embodiments, the patient exhibits reduced back pain following administration of the compound to the patient, for instance, as assessed using a Numerical Rating Score and/or a Verbal Rating Score as described herein.

In some embodiments, the patient does not exhibit a reduction in bone mineral density of greeter than 5% following administration of the compound to the patient. In some embodiments, the patient does not exhibit a reduction in bone mineral density of greeter than 1% following administration of the compound to the patient.

In some embodiments, the bone mineral density is assessed by dual energy X-ray absorptiometry, for instance, in the spine or femur of the patient.

In some embodiments, the bone mineral density is assessed by comparing the concentration of BAP in a sample (e.g., a urine sample) isolated from the patient following the administration to the concentration of BAP in a sample (e.g., a urine sample) isolated from the patient prior to the administration.

In some embodiments, the bone mineral density is assessed by comparing the concentration of DPD in a sample (e.g., a urine sample) isolated from the patient following the administration to the concentration of DPD in a sample (e.g., a urine sample) isolated from the patient prior to the administration.

In some embodiments, the bone mineral density is assessed by comparing the concentration of CTX in a sample (e.g., a urine sample) isolated from the patient following the administration to the concentration of CTX in a sample (e.g., a urine sample) isolated from the patient prior to the administration.

In some embodiments, the bone mineral density is assessed by comparing the concentration of P1NP in a sample (e.g., a urine sample) isolated from the patient following the administration to the concentration of P1NP in a sample (e.g., a urine sample) isolated from the patient prior to the administration.

In some embodiments, the compound (e.g., and add-back therapy) is administered to the patient daily (e.g., once daily and/or in any of the above-specified doses per day) for one or more treatment cycles. In some embodiments, the compound (e.g., and add-back therapy) is administered to the patient daily (e.g., once daily and/or in any of the above-specified doses per day) for one or more treatment cycles, each lasting for a period of about 4-72 weeks, or longer. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, 64 weeks, 65 weeks, 66 weeks, 67 weeks, 68 weeks, 69 weeks, 70 weeks, 71 weeks, 72 weeks, or more.

In some embodiments, the compound (e.g., and add-back therapy) is administered to the patient for one or more treatment cycles, each lasting for a period of about 4-64 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 53 weeks, 54 weeks, 55 weeks, 56 weeks, 57 weeks, 58 weeks, 59 weeks, 60 weeks, 61 weeks, 62 weeks, 63 weeks, or 64 weeks.

In some embodiments, the compound (e.g., and add-back therapy) is administered to the patient for one or more treatment cycles, each lasting for a period of about 4-52 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, or 52 weeks.

In some embodiments, the compound (e.g., and add-back therapy) is administered to the patient for one or more treatment cycles, each lasting for a period of about 4-48 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, or 48 weeks.

In some embodiments, the compound (e.g., and add-back therapy) is administered to the patient for one or more treatment cycles, each lasting for a period of about 4-24 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks.

In some embodiments, the compound (e.g., and add-back therapy) is administered to the patient for one or more treatment cycles, each lasting for a period of about 4-12 weeks. For instance, the compound (e.g., and add-back therapy) may be administered to the patient daily (e.g., once daily and/or in any of the above-specified doses per day) for one or more treatment cycles, each lasting about 4 weeks, 5 weeks, 6 weeks, 7 weeks, 8 weeks, 9 weeks, 10 weeks, 11 weeks, or 12 weeks.

In some embodiments, the compound (e.g., and add-back therapy) is administered to the patient for one or more treatment cycles (e.g., daily, such as once daily and/or in any of the above-specified doses per day), each treatment cycle lasting for a period of about 4 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 6 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 8 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 12 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 24 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 36 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 48 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 52 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 64 weeks. In some embodiments, the compound (e.g., and add-back therapy) is administered to the patient for one or more treatment cycles (e.g., daily, such as once daily and/or in any of the above-specified doses per day), each treatment cycle lasting for a period of about 72 weeks.

In another aspect, the invention features a kit containing a compound represented by formula (I),

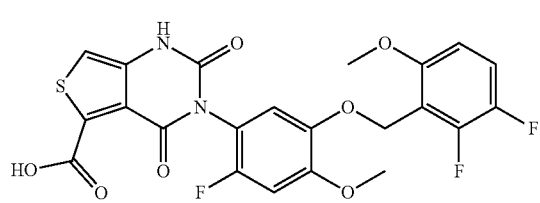
(I)

or a pharmaceutically acceptable salt thereof, and may further include a package insert, such as a package insert that instructs a user of the kit to perform a method of any of the aspects or embodiments of the invention described herein. In some embodiments, the compound within the kit is the choline salt of the compound represented by formula (I), shown as formula (II), below.

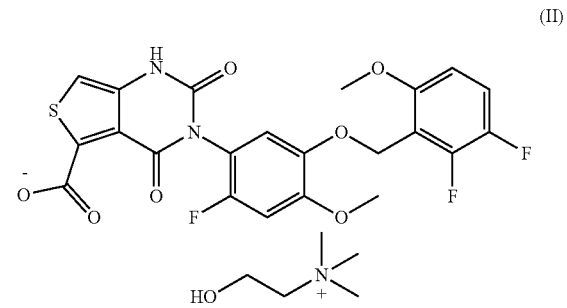
(II)

In some embodiments, the kit contains the above compound, or pharmaceutically acceptable salt thereof (e.g., the choline salt thereof) in an amount of about 100 mg per unit dosage form (e.g., 100 mg per unit dosage form). In some embodiments, the kit contains the above compound, or pharmaceutically acceptable salt thereof (e.g., the choline salt thereof) in an amount of about 200 mg per unit dosage form (e.g., 200 mg per unit dosage form). The kit may contain the compound in one or more unit dosage forms, such as a quantity of unit dosage forms sufficient for once-daily administration of the compound for from 1 day to 30 days, 1 day to 60 days, 1 day to 90 days, 1 day to 120 days, or more.

In some embodiments, the kit further includes a pharmaceutical composition containing add-back therapy, such as an estrogen and/or progestin described above or herein.

In some embodiments, the kit contains an estrogen, such as β17-estradiol. The β17-estradiol may be present within the kit in an amount of from about 0.1 mg to about 2.5 mg per unit dosage form, such as in an amount of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg per unit dosage form. The kit may contain the β17-estradiol in one or more unit dosage forms, such as a quantity of unit dosage forms sufficient for once-daily administration of the β17-estradiol for from 1 day to 30 days, 1 day to 60 days, 1 day to 90 days, 1 day to 120 days, or more.

In some embodiments, the estrogen is ethinyl estradiol. The ethinyl estradiol may be present within the kit in an amount of from about 1.0 μg to about 6.0 μg per unit dosage form, such as in an amount of about 1.0 μg, 1.1 μg, 1.2 μg, 1.3 μg, 1.4 μg, 1.5 μg, 1.6 μg, 1.7 μg, 1.8 μg, 1.9 μg, 2.0 μg, 2.1 μg, 2.2 μg, 2.3 μg, 2.4 μg, 2.5 μg, 2.6 μg, 2.7 μg, 2.8 μg, 2.9 μg, 3.0 μg, 3.1 μg, 3.2 μg, 3.3 μg, 3.4 μg, 3.5 μg, 3.6 μg, 3.7 μg, 3.8 μg, 3.9 μg, 4.0 μg, 4.1 μg, 4.2 μg, 4.2 μg, 4.3 μg, 4.4 μg, 4.5 μg, 4.6 μg, 4.7 μg, 4.8 μg, 4.9 μg, 5.0 μg, 5.1 μg, 5.2 μg, 5.3 μg, 5.4 μg, 5.5 μg, 5.6 μg, 5.7 μg, 5.8 μg, 5.9 μg, or 6.0 μg per unit dosage form. The kit may contain the ethinyl estradiol in one or more unit dosage forms, such as a quantity of unit dosage forms sufficient for once-daily administration of the ethinyl estradiol for from 1 day to 30 days, 1 day to 60 days, 1 day to 90 days, 1 day to 120 days, or more.

In some embodiments, the estrogen is a conjugated estrogen, such as a conjugated equine estrogen. The conjugated estrogen may be present within the kit in an amount of from about 0.1 mg to about 2.0 mg per unit dosage form, such as in an amount of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg per unit dosage form. The kit may contain the conjugated estrogen in one or more unit dosage forms, such as a quantity of unit dosage forms sufficient for once-daily administration of the conjugated estrogen for from 1 day to 30 days, 1 day to 60 days, 1 day to 90 days, 1 day to 120 days, or more.

In some embodiments, the kit contains a progestin. In some embodiments, the progestin is selected from the group consisting of norethindrone or an ester thereof, such as norethindrone acetate, or another agent such as progesterone, norgestimate, medroxyprogesterone, or drospirenone.

In some embodiments, the progestin is norethindrone or a compound that is metabolized in vivo to produce norethindrone, such as an ester of norethindrone that is de-esterified in vivo to produce norethindrone, for instance, norethindrone acetate.

In some embodiments, the progestin is norethindrone. The norethindrone may be present within the kit in an amount of from about 0.05 mg to about 5.0 mg per unit dosage form, such as in an amount of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg per unit dosage form. The kit may contain the norethindrone in one or more unit dosage forms, such as a quantity of unit dosage forms sufficient for once-daily administration of the norethindrone for from 1 day to 30 days, 1 day to 60 days, 1 day to 90 days, 1 day to 120 days, or more.

In some embodiments, the progestin is norethindrone acetate. The norethindrone acetate may be present within the kit in an amount of from about 0.05 mg to about 5.0 mg per unit dosage form, such as in an amount of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg per unit dosage form. The kit may contain the norethindrone acetate in one or more unit dosage forms, such as a quantity of unit dosage forms sufficient for once-daily administration of the norethindrone acetate for from 1 day to 30 days, 1 day to 60 days, 1 day to 90 days, 1 day to 120 days, or more.

In some embodiments, the progestin is progesterone. The progesterone may be present within the kit in an amount of from about 50 mg to about 250 mg per unit dosage form, such as in an amount of about 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, or 250 mg per unit dosage form. The kit may contain the progesterone in one or more unit dosage forms, such as a quantity of unit dosage forms sufficient for once-daily administration of the progesterone for from 1 day to 30 days, 1 day to 60 days, 1 day to 90 days, 1 day to 120 days, or more.

In some embodiments, the progestin is norgestimate. The norgestimate may be present within the kit in an amount of from about 0.01 mg to about 2.0 mg per unit dosage form, such as in an amount of about 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg per unit dosage form. The kit may contain the norgestimate in one or more unit dosage forms, such as a quantity of unit dosage forms sufficient for once-daily administration of the norgestimate for from 1 day to 30 days, 1 day to 60 days, 1 day to 90 days, 1 day to 120 days, or more.

In some embodiments, the progestin is medroxyprogesterone. The medroxyprogesterone may be present within the kit in an amount of from about 0.5 mg to about 10.0 mg per unit dosage form, such as in an amount of about 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg per unit dosage form. The kit may contain the medroxyprogesterone in one or more unit dosage forms, such as a quantity of unit dosage forms sufficient for once-daily administration of the medroxyprogesterone for from 1 day to 30 days, 1 day to 60 days, 1 day to 90 days, 1 day to 120 days, or more.

In some embodiments, the progestin is drospirenone. The drospirenone may be present within the kit in an amount of from about 0.1 mg to about 1.0 mg per unit dosage form, such as in an amount of about 0.1 mg, 0.2 mg, 0.3 mg, 0.4 mg, 0.5 mg, 0.6 mg, 0.7 mg, 0.8 mg, 0.9 mg, or 1.0 mg per unit dosage form. The kit may contain the drospirenone in one or more unit dosage forms, such as a quantity of unit dosage forms sufficient for once-daily administration of the drospirenone for from 1 day to 30 days, 1 day to 60 days, 1 day to 90 days, 1 day to 120 days, or more.

In some embodiments, the kit contains an estrogen and progestin, such as β17-estradiol and norethindrone or a compound that is metabolized in vivo to produce norethindrone, such as an ester of norethindrone that is de-esterified in vivo to produce norethindrone, for instance, norethindrone acetate. The β17-estradiol may be present within the kit in an amount of from about 0.1 mg to about 2.5 mg per unit dosage form, such as in an amount of about 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, or 2.5 mg per unit dosage form. The kit may contain the β17-estradiol in one or more unit dosage forms, such as a quantity of unit dosage forms sufficient for once-daily administration of the β17-estradiol for from 1 day to 30 days, 1 day to 60 days, 1 day to 90 days, 1 day to 120 days, or more. The norethindrone or compound that is metabolized in vivo to produce norethindrone, such as an ester of norethindrone that is de-esterified in vivo to produce norethindrone (e.g., norethindrone acetate) may be present within the kit in an amount of from about 0.05 mg to about 5.0 mg per unit dosage form, such as in an amount of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, or 5.0 mg per unit dosage form. The kit may contain the norethindrone or compound that is metabolized in vivo to produce norethindrone, such as an ester of norethindrone that is de-esterified in vivo to produce norethindrone (e.g., norethindrone acetate) in one or more unit dosage forms, such as a quantity of unit dosage forms sufficient for once-daily administration of the norethindrone for from 1 day to 30 days, 1 day to 60 days, 1 day to 90 days, 1 day to 120 days, or more.

In some embodiments, the kit contains the compound represented by formula (I) or a pharmaceutically acceptable salt thereof, such as the choline salt thereof, and the add-back therapy (e.g., estrogen and/or progestin) in a fixed-dose composition, such as a tablet, capsule, gel cap, powder, liquid solution, or liquid suspension containing each of these agents in combination with one another. In some embodiments, the compound, estrogen, and progestin, when present, are each present in separate pharmaceutical compositions. In some embodiments, the compound is present in one pharmaceutical composition, and the estrogen and progestin are present, in combination with one another, in a separate pharmaceutical composition.

Definitions

As used herein, the term "about" refers to a value that is within 10% above or below the value being described. For instance, a value of "about 5 nM" refers to a quantity that is from 4.5 nM to 5.5 nM.

As used herein, the term "add-back therapy" refers to the administration of estrogen during a treatment regimen, such as treatment with a GnRH antagonist (e.g., 3-[2-fluoro-5-

(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, as described herein), so as to counteract side effects that may otherwise be associated with excessive suppression of estradiol. Such side effects may include, for example, a reduction in bone mineral density (BMD). A patient's BMD may be assessed by dual energy X-ray absorptiometry, for instance, in the spine or femur of the patient. Add-back therapy may be administered to a patient according to the methods described herein so as to mitigate a reduction in BMD caused by the administration of a GnRH antagonist. For instance, add-back therapy may be administered to a patient undergoing GnRH antagonist therapy such that the patient does not exhibit a reduction in BMD of greater than 5% (e.g., no greater than 5%, 4%, 3%, 2%, 1%, 0.9%, 0.8%, 0.7%, 0.6%, 0.5%, 0.4%, 0.3%, 0.2%, 0.1%, or less). Add-back therapy may include estrogen in the form of β17-estradiol, ethinyl estrogen, or a conjugated estrogen, such as a conjugated equine estrogen, and may further include one or more additional agents, such as a progestin (e.g., norethindrone or a compound that is metabolized in vivo to produce norethindrone, such as an ester of norethindrone that is de-esterified in vivo to produce norethindrone, for instance, norethindrone acetate, among other progestins such as progesterone, norgestimate, medroxyprogesterone, and drospirenone). Add-back therapy may be formulated for oral administration, such as in the form of a tablet, capsule, gel cap, powder, liquid solution, or liquid suspension. Add-back therapy may feature a co-formulation containing estrogen (e.g., in the form of β17-estradiol) and an additional agent such as a progestin (e.g., norethindrone or a compound that is metabolized in vivo to produce norethindrone, such as an ester of norethindrone that is de-esterified in vivo to produce norethindrone, for instance, norethindrone acetate). For instance, add-back therapy may be administered to a patient in the form of a single tablet, capsule, gel cap, powder, liquid solution, or liquid suspension that contains both estrogen (e.g., in the form of β17-estradiol) and a progestin (e.g., norethindrone or a compound that is metabolized in vivo to produce norethindrone, such as an ester of norethindrone that is de-esterified in vivo to produce norethindrone, for instance, norethindrone acetate). In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate) in the form of a single pharmaceutical composition, such as a single tablet, capsule, gel cap, powder, liquid solution, or liquid suspension.

As used herein, the term "affinity" refers to the strength of a binding interaction between two molecules, such as a ligand and a receptor. The term "K", as used herein, is intended to refer to the inhibition constant of an antagonist for a particular molecule of interest, and can be expressed as a molar concentration (M). K values for antagonist-target interactions can be determined, e.g., using methods established in the art. Methods that can be used to determine the K of an antagonist for a molecular target include competitive binding experiments, e.g., as described in U.S. Pat. No. 9,040,693. The term "$K_d$", as used herein, is intended to refer to the dissociation constant, which can be obtained, e.g., from the ratio of the rate constant for the dissociation of the two molecules ($k_d$) to the rate constant for the association of the two molecules ($k_a$) and is expressed as a molar concentration (M). $K_d$ values for receptor-ligand interactions can be determined, e.g., using methods established in the art. Methods that can be used to determine the $K_d$ of a receptor-ligand interaction include surface plasmon resonance, e.g., through the use of a biosensor system such as a BIACORE® system.

As used herein, the term "amenorrhea" refers to the absence of menstruation in a female patient, such as a human female patient undergoing GnRH antagonist treatment according to a dosing regimen described herein. As such, amenorrhea is a clinical indicator of reduced menstrual blood loss, such as reduced menstrual blood loss in a uterine fibroids patient undergoing GnRH antagonist treatment according to a dosing regimen described herein.

As used herein, the terms "benefit" and "response" are used interchangeably in the context of a subject, such as a female human subject having uterine fibroids and/or suffering from heavy menstrual bleeding. These terms refers to any clinical improvement in the subject's condition. Exemplary benefits in the context of a subject having uterine fibroids and/or exhibiting heavy menstrual bleeding and receiving treatment with a GnRH antagonist described herein (e.g., a thieno[3,4d]pyrimidine compound, such as 3-[2-fluoro-5-(2,3-difluoro-6-methoxybenzyloxy)-4-methoxyphenyl]-2,4-dioxo-1,2,3,4-tetrahydrothieno [3,4d] pyrimidine-5-carboxylic acid or a pharmaceutically acceptable salt thereof, such as the choline salt thereof) include, without limitation, (i) a reduction in menstrual blood loss from an initial value of, for example, 80 ml or more per menstrual cycle (recorded prior to the initiation of treatment according to a dosing regimen described herein) to a reduced value of, for example, 60 ml, 55 ml, 50 ml, 45 ml, 40 ml, 35 ml, 30 ml, 25 ml, 20 ml, 15 ml, 10 ml, 5, ml, or less, of menstrual blood loss per menstrual cycle following the administration of the GnRH antagonist, (ii) a reduction in menstrual blood loss, for instance, of 25% or more by volume per menstrual cycle (e.g., a reduction in menstrual blood loss of 25%, 30%, 35%, 40%, 45%, 50%, 55%, 60%, 65%, 70%, 75%, 80%, 85%, 90%, 95%, 96%, 97%, 98%, 99%, 99.9%, 99.99%, or more (e.g., 100%) by volume per menstrual cycle) relative to a measurement of the volume of menstrual blood lost by the patient per menstrual cycle prior to the first administration of the GnRH antagonist to the patient, (iii) the onset of amenorrhea following administration of the GnRH antagonist to the patient, such as amenorrhea that is sustained, for instance, for a period of at least about 5 days, at least about 7 days, at least about 10 days, at least about 4 weeks, at least about 8 weeks, at least about 12 weeks, at least about 16 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, or more, such as for a period of from about 5 days to about 52 weeks, (iv) a reduction in the number of days during a patient's menstrual cycle in which the patient exhibits menstrual bleeding following administration of the GnRH antagonist to the patient, such as a reduction of from about 1% to about 100% (e.g., a reduction of from about 1 day to about 28 days in a 28-day menstrual cycle, such as a reduction of about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, or 28 days, or the entirety of the days in the patient's menstrual cycle), and (v) an increase in serum hemoglobin concentration, for instance, of from about 1% to 100% or more, such as an increase of 1%; 2%, 3%, 4%, 5%, 6%, 7%, 8%, 9%, 10%, 11%; 12%, 13%, 14%, 15%, 16%, 17%, 18%, 19%, 20%, 21%; 22%, 23%, 24%, 25%, 26%, 27%, 28%, 29%, 30%, 31%; 32%, 33%, 34%, 35%, 36%, 37%, 38%, 39%, 40%, 41%; 42%, 43%, 44%, 45%, 46%, 47%, 48%, 49%, 50%, 51%; 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%; 82%, 83%, 84%, 85%, 86%, 87%, 88%, 89%, 90%, 91%; 92%, 93%, 94%, 95%, 96%, 97%, 98%, 99%, 100%, 200%, 500%, or more, in the patient following administration of the GnRH antagonist to the patient.

As used herein, the term "crystalline" or "crystalline form" means having a physical state that is a regular three-dimensional array of atoms, ions, molecules or molecular assemblies. Crystalline forms have lattice arrays of building blocks called asymmetric units that are arranged according to well-defined symmetries into unit cells that are repeated in three-dimensions. In contrast, the term "amorphous" or "amorphous form" refers to an unorganized (no orderly) structure. The physical state of a therapeutic compound may be determined by exemplary techniques such as x-ray diffraction, polarized light microscopy and/or differential scanning calorimetry.

As used herein, the term "dose" refers to the quantity of a therapeutic agent, such as GnRH antagonist described herein, that is administered to a subject during a given time for the treatment of a disorder or condition, such as to reduce the volume of menstrual blood loss in a female mammalian subject (e.g., a female human subject). A therapeutic agent as described herein, such as a GnRH antagonist represented by formula (I), herein, or a pharmaceutically acceptable salt thereof, such as the choline salt represented by formula (II), herein, may be administered in a single dose or in multiple doses, for instance, over a given treatment period. In each case, the therapeutic agent may be administered using one or more unit dosage forms of the therapeutic agent. In the case of administration using two or more unit dosage forms, the unit dosage forms may be administered the same time or at different times, for instance, by the same or different routes of administration. For instance, a single dose of 200 mg of a therapeutic agent, such as a GnRH antagonist described herein, may be administered (e.g., orally) using, e.g., a single unit dosage form of 200 mg of the therapeutic agent (such as a single tablet, capsule, gel cap, powder, liquid solution, or liquid suspension containing 200 mg of the therapeutic agent) or two 100 mg unit dosage forms of the therapeutic agent (such as two tablets, capsules, gel caps, powders, liquid solutions, or liquid suspensions each containing 100 mg of the therapeutic agent). Similarly, a single dose of 100 mg of a therapeutic agent, such as a GnRH antagonist described herein, may be administered (e.g., orally) using, e.g., a single unit dosage form of 100 mg of the therapeutic agent (such as a single tablet, capsule, gel cap, powder, liquid solution, or liquid suspension containing 100 mg of the therapeutic agent) or two 50 mg unit dosage forms of the therapeutic agent (such as two tablets, capsules, gel caps, powders, liquid solutions, or liquid suspensions each containing 50 mg of the therapeutic agent).

As used herein, the term "dual energy X-ray absorptiometry" (DEXA) refers to a spectroscopic method of measuring bone mineral density in a patient (e.g., a human patient) in which X-ray radiation of two distinct frequencies are transmitted towards a target bone of the patient. The absorption of the transmitted radiation can subsequently be correlated with a measure of the bone mineral density within the target bone. Methods of determining bone mineral density using DEXA are described in detail, e.g., in Mazess et al., American Journal of Clinical Nutrition 51:1106-1112 (1990).

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell).

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell). Exogenous materials include those that are provided from an external source to an organism or to cultured matter extracted there from.

As used herein, the term "gonadotropin-releasing hormone antagonist" or "GnRH antagonist" refers to a compound capable of inhibiting the gonadotropin-releasing hormone receptor, e.g., such that release of one or more gonadotropins (such as follicle stimulating hormone and luteinizing hormone) is inhibited. GnRH antagonists for use with the compositions and methods described herein include thieno[3,4d]pyrimidine derivatives and variants, such as 3-[2-fluoro-5-(2,3-difluoro-6-methoxybenzyloxy)-4-methoxyphenyl]-2,4-dioxo-1,2,3,4-tetrahydrothieno [3,4d] pyrimidine-5-carboxylic acid or a pharmaceutically acceptable salt thereof, such as the choline salt thereof, e.g., as described in U.S. Pat. No. 9,169,266, the disclosure of which is incorporated herein by reference in its entirety.

As used herein, the terms "heavy menstrual bleeding," "heavy menstrual blood loss," and "menorrhagia" are used interchangeably and refer to abnormally high menstrual blood loss, such as menstrual blood loss of 80 ml or more (e.g., 80 ml, 90 ml, 100 ml, 110 ml, 120 ml, 130 ml, 140 ml, 150 ml, 160 ml, 170 ml, 180 ml, 190 ml, 200 ml, or more) per menstrual cycle (The Menorrhagia Research Group. Quantification of menstrual blood loss. The Obstetrician & Gynaecologist 6:88-92 (2004)).

As used herein, the term "$IC_{50}$" refers to the concentration of a substance (antagonist) that reduces the efficacy of a reference agonist or the constitutive activity of a biological target by 50%, e.g., as measured in a competitive ligand binding assay. Exemplary competitive ligand binding assays include competitive radioligand binding assays, competitive enzyme-linked immunosorbant assays (ELISA), and fluorescence anisotropy-based assays, among others known in the art.

As used herein in the context of providing or administering two or more therapeutic agents to a subject, such as in the context of providing or administering a GnRH antagonist described herein (e.g., a thieno[3,4d]pyrimidine compound described herein, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof) and add-back therapy to a subject, the phrase "in combination with" refers to the delivery of the two or more therapeutic agents to a subject (e.g., a mammalian subject, such as a female human subject having uterine fibroids) either (i) concurrently or (ii) at different times such that the later-administered agent is provided to the subject while there is still a detectable concentration of the earlier-administered agent, or a metabolite thereof, in the plasma and/or one or more tissue(s) or gland(s) (e.g., pituitary tissue) of the subject. For example, one therapeutic agent (such as a GnRH antagonist described herein) may be administered to a subject in combination with another therapeutic agent or agents (e.g., one or more add-back therapy agents described herein) by administering all agents to the subject concurrently, such as in a single pharmaceutical composition or in separate compositions that are administered to the subject simultaneously (e.g., by the same or different routes of administration). In another example, one therapeutic agent may be administered to a subject in combination with another by first administering to the subject one therapeutic agent and subsequently administering the other therapeutic agent, either by the same or different route of administration, while there is still a detectable quantity of the first agent in the plasma and/or tissue(s) of the subject. After the first administration of each agent (e.g., concurrently or at different times), it is not necessary that the subject receive the remaining agent(s) each and every time the subject receives a dose of the first agent. For instance, two or more agents are considered to be administered "in combination with" one another if the subject receives a daily dosage of a first agent and a weekly dosage of the remaining agent(s), as long as there is still a detectable concentration of the earlier-administered agent, or a metabolite thereof, in the plasma and/or one or more tissue(s) or gland(s) of the subject at the time of administration of the later-administered agent. The timing of administration of the two or more agents need not coincide.

As used herein, the term "menstrual cycle" refers to a recurring cycle of physiological changes in females, such as human females, that is associated with reproductive fertility. While the cycle length may vary from woman to woman, 28 days is generally taken as representative of the average ovulatory cycle in human females.

As used herein, the term "Numerical Rating Score" (NRS) refers to a score within an 11-point numerical scale of 0-10 that indicates the degree of pain experienced by a patient. For instance, a score of 0 may indicate the patient is experiencing no pain, while scores from 1-3 may indicate that the patient is experiencing mild pain. A score of from 4-6 may indicate that the patient is experiencing moderate pain, and a score of from 7-10 may indicate that the patient is experiencing severe pain. Typically, to determine a NRS score, the patient is asked to indicate the level of pain currently being experienced, as well as the pain experienced at its most intense and least intense occurrences. Methods for determining a NRS are described in detail, e.g., in McCaffery et al., Pain: Clinical Manual for Nursing Practice. Baltimore (1993).

As used herein in the context of administration of a therapeutic agent, the term "periodically" refers to administration of the agent two or more times over the course of a treatment period (e.g., two or more times daily, weekly, monthly, or yearly).

As used herein, the term "pharmaceutical composition" means a mixture containing a therapeutic compound to be administered to a patient, such as a mammal, e.g., a human, in order to prevent, treat, or control a particular disease or condition affecting the mammal, such as uterine fibroids or heavy menstrual bleeding, for example, resulting therefrom.

As used herein, the term "pharmaceutically acceptable" refers to those compounds, materials, compositions and/or dosage forms, which are suitable for contact with the tissues of a patient, such as a mammal (e.g., a human) without excessive toxicity, irritation, allergic response and other problem complications commensurate with a reasonable benefit/risk ratio.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a patient.

As used herein, the phrases "specifically binds" and "binds" refer to a binding reaction which is determinative of the presence of a particular protein in a heterogeneous population of proteins and other biological molecules that is recognized, e.g., by a ligand with particularity. A ligand (e.g., a protein, proteoglycan, or glycosaminoglycan) that specifically binds to a protein will bind to the protein, e.g., with a $K_D$ of less than 100 nM. For example, a ligand that specifically binds to a protein may bind to the protein with a $K_D$ of up to 100 nM (e.g., between 1 µM and 100 nM). A ligand that does not exhibit specific binding to a protein or a domain thereof may exhibit a $K_D$ of greater than 100 nM (e.g., greater than 200 nM, 300 nM, 400 nM, 500 nM, 600 nm, 700 nM, 800 nM, 900 nM, 1 µM, 100 µM, 500 µM, or 1 mM) for that particular protein or domain thereof. A variety of assay formats may be used to determine the affinity of a ligand for a specific protein. For example, solid-phase ELISA assays are routinely used to identify ligands that specifically bind a target protein. See, e.g., Harlow & Lane, Antibodies, A Laboratory Manual, Cold Spring Harbor Press, New York (1988) and Harlow & Lane, Using Antibodies, A Laboratory Manual, Cold Spring Harbor Press, New York (1999), for a description of assay formats and conditions that can be used to determine specific protein binding.

As used herein, the terms "subject" and "patient" are used interchangeably and refer to an organism, such as a mammal (e.g., a human) that receives treatment for a particular disease or condition as described herein (such as heavy menstrual blood loss occurring in a patient having uterine fibroids) or that is diagnosed as having a disease or condition according to the methods described herein. Examples of patients include mammals, such as humans, receiving treatment for diseases or conditions, for example, heavy menstrual bleeding. Those patients that are "in need of treatment" using a GnRH antagonist according to the dosing regimens described herein include, e.g., female patients already diagnosed as having uterine fibroids, such as human female patients exhibiting menstrual blood loss of greater than 40 ml per menstrual cycle, such as human female patients exhibiting menstrual blood loss of 80 ml or more per menstrual cycle. Menstrual blood loss of 80 ml or more per menstrual cycle is indicative of heavy menstrual bleeding, also referred to as menorrhagia (The Menorrhagia Research Group. Quantification of menstrual blood loss. The Obstetrician & Gynaecologist 6:88-92 (2004)). Patients in need of GnRH antagonist treatment according to a GnRH antagonist dosing regimens described herein, such as a dosing regimen for the administration of thieno[3,4d]pyrimidine derivatives and variants, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, include female human patients exhibiting menorrhagia, such as those presenting with or diagnosed as having uterine fibroids. For example, patients that may be treated using the compositions and methods described herein include those that (i) exhibit heavy menstrual blood loss (e.g., loss of from 80 ml to 200 ml, or more, per menstrual cycle, such as a loss of 80 ml, 85 ml, 90 ml, 95 ml, 100 ml, 105 ml, 110 ml, 115 ml, 120 ml, 125 ml, 130 ml, 135 ml, 140 ml, 145 ml, 150 ml, 155 ml, 160 ml, 165 ml, 170 ml, 175 ml, 180 ml, 185 ml, 190 ml, 195 ml, 200 ml, or more, per menstrual cycle), (ii) have exhibited heavy menstrual blood loss (e.g., loss of from 80 ml to 200 ml, or more, per menstrual cycle, such as a loss of 80 ml, 85 ml, 90 ml, 95 ml, 100 ml, 105 ml, 110 ml, 115 ml, 120 ml, 125 ml, 130 ml, 135 ml, 140 ml, 145 ml, 150 ml, 155 ml, 160 ml, 165 ml, 170 ml, 175 ml, 180 ml, 185 ml, 190 ml, 195 ml, 200 ml, or more, per menstrual cycle) for each of the previous two menstrual cycles, (iii) have menstrual cycles of from about 21 days to about 40 days, such as menstrual cycles of about 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, or 40 days, (iv) are premenopausal, and/or (v) are diagnosed as having uterine fibroids. Patients that may be treated using a GnRH antagonist dosing regimen described herein include those that exhibit one or more, or all, of the foregoing characteristics, for example, prior to the first administration the GnRH antagonist (such as a thieno[3,4d]pyrimidine compound, for example, 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof).

As used herein in the context of a GnRH antagonist, such as a thieno[3,4d]pyrimidine compound, for example, 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, the term "therapeutically effective amount" refers to a quantity of the GnRH antagonist that achieves a beneficial treatment outcome for a subject having uterine fibroids and/or exhibiting heavy menstrual bleeding. For example, "therapeutically effective amounts" of a GnRH antagonist described herein are amounts that are capable of achieving (i) a reduction in menstrual blood loss from an initial value of, for example, 80 ml or more per menstrual cycle (recorded prior to the initiation of treatment according to a dosing regimen described herein) to a reduced value of, for example, 60 ml, 55 ml, 50 ml, 45 ml, 40 ml, 35 ml, 30 ml, 25 ml, 20 ml, 15 ml, 10 ml, 5, ml, or less, of menstrual blood loss per menstrual cycle following the administration of the GnRH antagonist, (ii) a reduction in menstrual blood loss, for instance, of 25% or more by volume per menstrual cycle (e.g., a reduction in menstrual blood loss of 25%, 30%, 35%, 40%, 45%, 50%, 55%, 60%, 65%, 70%, 75%, 80%, 85%, 90%, 95%, 96%, 97%, 98%, 99%, 99.9%, 99.99%, or more (e.g., 100%) by volume per menstrual cycle) relative to a measurement of the volume of menstrual blood lost by the patient per menstrual cycle prior to the first administration of the GnRH antagonist to the patient, (iii) the onset of amenorrhea following administration of the GnRH antagonist to the patient, such as amenorrhea that is sustained, for instance, for a period of at least about 5 days, at least about 7 days, at least about 10 days, at least about 4 weeks, at least about 8 weeks, at least about 12 weeks, at least about 16 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, or more, such as for a period of from about 5 days to about 52 weeks, (iv) a reduction in the number of days during a patient's menstrual cycle in which the patient exhibits menstrual bleeding following administration of the GnRH antagonist to the patient, such as a reduction of from about 1% to about 100% (e.g., a reduction of from about 1 day to about 28 days in a 28-day menstrual cycle, such as a reduction of about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, or 28 days, or the entirety of the days in the patient's menstrual cycle), and/or (v) an increase in serum hemoglobin concentration, for instance, of from about 1% to 100% or more, such as an increase of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 500%, or more, in the patient following administration of the GnRH antagonist to the patient.

As used herein, the terms "treat" or "treatment" refer to therapeutic treatment, in which the object is to prevent or slow down (lessen) an undesired physiological change or disorder, such as heavy menstrual bleeding in a patient presenting with and/or previously diagnosed as having uterine fibroids. Beneficial or desired clinical results indicative of successful treatment of a patient having uterine fibroids as described herein include, but are not limited to, alleviation of symptoms, such as reduction in menstrual blood loss in patients having uterine fibroids. As a non-limiting example, uterine fibroids in a patient, such as a human female patient, may be considered to be treated using a dosing regimen described herein if the patient exhibits a reduction in menstrual blood loss from an initial value of 80 ml per menstrual cycle or more (recorded prior to the initiation of treatment according to a dosing regimen described herein) to a reduced value of, for example, 60 ml, 55 ml, 50 ml, 45 ml, 40 ml, 35 ml, 30 ml, 25 ml, 20 ml, 15 ml, 10 ml, 5, ml, or less, of menstrual blood loss per menstrual cycle following the administration of a GnRH antagonist, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, to a patient according to a dosing regimen described herein. The reduction in menstrual blood loss may occur, for instance, within from about 3 days to about 52 weeks, from about 3 days to about 24 weeks, or from about 3 days to about 28 days of the first administration of the GnRH antagonist to the patient. This reduction in menstrual blood loss per menstrual cycle may occur, for instance, during the patient's final menstrual cycle of a 24-week treatment period. An additional clinical indicator of successful treatment of uterine fibroids in a patient is a finding that the patient exhibits a reduction in menstrual blood loss, for instance, of 25% or more by volume per menstrual cycle (e.g., a reduction in menstrual blood loss of 25%, 30%, 35%, 40%, 45%, 50%, 55%, 60%, 65%, 70%, 75%, 80%, 85%, 90%, 95%, 96%, 97%, 98%, 99%, 99.9%, 99.99%, or more (e.g., 100%) by volume per menstrual cycle) relative to a measurement of the volume of menstrual blood lost by the patient per menstrual cycle prior to the first administration of the GnRH antagonist to the patient. For example, successful treatment of uterine fibroids may be signaled by a finding that the patient exhibits a reduction in menstrual blood loss of 50% or more by volume per menstrual cycle (e.g., a reduction in menstrual blood loss of 50%, 55%, 60%, 65%, 70%, 75%, 80%, 85%, 90%, 95%, 96%, 97%, 98%, 99%, 99.9%, 99.99%, or more (e.g., 100%) by volume per menstrual cycle) relative to a measurement of the volume of menstrual blood lost by the patient per menstrual cycle prior to the first administration of the GnRH antagonist to the patient The reduction in menstrual blood loss may occur, for instance, within from about 3 days to about 52 weeks, from about 3 days to about 24 weeks, or from about 3 days to about 28 days of the first administration of the GnRH antagonist to the patient. In some embodiments, the reduction in menstrual blood loss is observed within the last 28 days of a 24-week treatment period of the GnRH antagonist, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof. Another significant clinical indicator of reduced menstrual blood loss and successful treatment of uterine fibroids is amenorrhea. Thus, in another example, uterine fibroids in a patient, such as a human female patient, may be considered to be treated using a dosing regimen described herein if the patient exhibits amenorrhea following administration of the GnRH antagonist to the patient. The amenorrhea may be sustained, for instance, for a period of at least about 5 days, at least about 7 days, at least about 10 days, at least about 4 weeks, at least about 8 weeks, at least about 12 weeks, at least about 16 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, or more, such as for a period of from about 5 days to about 52 weeks (e.g., about 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more). The amenorrhea may occur, for instance, within from about 3 days to about 52 weeks, from about 3 days to about 24 weeks, or from about 3 days to about 28 days of the first administration of the GnRH antagonist to the patient. In some embodiments, successful treatment of uterine fibroids is signaled by an observation that the patient exhibits sustained amenorrhea within the last 28 days of a 24-week treatment period of the GnRH antagonist, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof. Successful treatment of uterine fibroids may also manifest as a reduction in the number of days during a patient's menstrual cycle in which the patient exhibits menstrual bleeding, such as a reduction of from about 1% to about 100% (e.g., a reduction of from about 1 day to about 28 days in a 28-day menstrual cycle, such as a reduction of about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, or 28 days, or the entirety of the days in the patient's menstrual cycle). The reduction in the quantity of days in the patient's menstrual cycle in which the patient exhibits menstrual bleeding may be observed, for instance, within from about 3 days to about 52 weeks, from about 3 days to about 24 weeks, or from about 3 days to about 28 days of the first administration of the GnRH antagonist to the patient. The reduction in the quantity of days in the patient's menstrual cycle in which the patient exhibits menstrual bleeding may be observed, for example, during the patient's final menstrual cycle of a 24-week treatment period. Additional clinical indicators of successful treatment of a patient having uterine fibroids include a finding that the patient exhibits an increase in serum hemoglobin concentration, for instance, of from about 1% to 100% or more, such as an increase of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 500%, or more. The increase in serum hemoglobin may be observed, for instance, within from about 3 days to about 52 weeks, from about 3 days to about 24 weeks, or from about 3 days to about 28 days of the first administration of the GnRH antagonist to the patient. In some embodiments, the increase in serum hemoglobin is observed within 24 weeks of initiating treatment with the GnRH antagonist, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof.

As used herein, the terms "treatment period" and "treatment cycle" are used interchangeably and refer to a duration of time over which a patient may be administered a therapeutic agent, such as a GnRH antagonist described herein, optionally in combination with add-back therapy described herein, for example, so as to treat uterine fibroids or reduce the volume of menstrual blood loss in a patient, such as a female human patient. Treatment periods as described herein may have a duration of several days, weeks, months, or years. For instance, a treatment period for administration of a GnRH antagonist described herein, such as a thieno[3,4d] pyrimidine compound (for example, 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof), may last for from one or more days to one or more months or years, such as from about 4 weeks to about 52 weeks, or longer. Exemplary treatment periods during which a patient, such as a female human patient having uterine fibroids, may be periodically administered a GnRH antagonist described herein, such as a thieno[3,4d] pyrimidine compound (for example, 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof), optionally in combination with add-back therapy, include cycles of about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more. For instance, the GnRH antagonist (e.g., and add-back therapy) may be administered to the patient daily for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25, weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more. In some embodiments, the GnRH antagonist (e.g., and add-back therapy) is periodically administered to the patient for one or more treatment cycles, each lasting for a period of about 4-48 weeks. For instance, the GnRH antagonist (e.g., and add-back therapy) may be administered to the patient daily for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25, weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, or 48 weeks. In some embodiments, the GnRH antagonist (e.g., and add-back therapy) is periodically administered to the patient for one or more treatment cycles, each lasting for a period of about 4-24 weeks. For instance, the GnRH antagonist (e.g., and add-back therapy) may be administered to the patient daily for one or more treatment cycles, each lasting about 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks. In some embodiments, the GnRH antagonist (e.g., and add-back therapy) is periodically administered to the patient for one or more treatment cycles, each lasting for a period of about 4-12 weeks. For instance, the compound (e.g., and add-back therapy) may be administered to the patient daily for one or more treatment cycles, each lasting about 4 weeks, 5 weeks, 6 weeks, 7 weeks, 8 weeks, 9 weeks, 10 weeks, 11 weeks, or 12 weeks. In some embodiments, the GnRH antagonist (e.g., and add-back therapy) is periodically administered to the patient for one or more treatment cycles, each lasting for a period of about 4 weeks. In some embodiments, the GnRH antagonist (e.g., and add-back therapy) is periodically administered to the patient for one or more treatment cycles, each lasting for a period of about 6 weeks. In some embodiments, the GnRH antagonist (e.g., and add-back therapy) is periodically administered to the patient for one or more treatment cycles, each lasting for a period of about 8 weeks. In some embodiments, the GnRH antagonist (e.g., and add-back therapy) is periodically administered to the patient for one or more treatment cycles, each lasting for a period of about 12 weeks. In some embodiments, the GnRH antagonist (e.g., and add-back therapy) is periodically administered to the patient for one or more treatment cycles, each lasting for a period of about 24 weeks. In some embodiments, the GnRH antagonist (e.g., and add-back therapy) is periodically administered to the patient for one or more treatment cycles, each lasting for a period of about 36 weeks. In some embodiments, the GnRH antagonist (e.g., and add-back therapy) is periodically administered to the patient for one or more treatment cycles, each lasting for a period of about 48 weeks. In some embodiments, the GnRH antagonist (e.g., and add-back therapy) is periodically administered to the patient for one or more treatment cycles, each lasting for a period of about 52 weeks. In some embodiments, the GnRH antagonist (e.g., and add-back therapy) is periodically administered to the patient for one or more treatment cycles, each lasting for a period of about 64 weeks. In some embodiments, the GnRH antagonist (e.g., and add-back therapy) is periodically administered to the patient for one or more treatment cycles, each lasting for a period of about 76 weeks.

As used herein, the term "Verbal Rating Score" (VRS) refers to a subjective multi-point scale used to indicate the level of pain being experienced by a patient undergoing therapy or that has previously undergone therapy for a disease or condition, such as heavy menstrual blood loss occurring in a patient that has uterine fibroids. The VRS may be a five-point scale and can be assessed by prompting the patient with one or more questions in order to determine the level of pain currently being experienced by the patient. Methods for assessing a VRS are described in detail, e.g., in Jensen et al., Journal of Pain and Symptom Management 41:1073-1093 (2011).

As used herein in the context of achieving a therapeutic effect within a certain time period of administering treatment to a patient, such as the administration of a GnRH antagonist to a patient presenting with heavy menstrual blood loss, phrases such as "within about 4 weeks of said administering," "within about 8 weeks of said administering," "within about 12 weeks of said administering," "within about 24 weeks of said administering," "within about 36 weeks of said administering," and the like refer to the achievement of a therapeutic phenotype within about the indicated time period as measured from the date of the initial administration of the particular GnRH antagonist to the patient. Exemplary therapeutic phenotypes that may be achieved by administration of a GnRH antagonist to a patient suffering from heavy menstrual blood loss, such as a human patient having uterine fibroids, include reduced β17-estradiol (E2), luteinizing hormone (LH), and/or follicle-stimulating hormone (FSH) concentrations in the serum of the patient, as well as reduced menstrual blood loss. For instance, a patient is considered to exhibit a reduced E2, LH, or FSH level "within about 4 days" of administering a GnRH antagonist to the patient according to a dosing schedule described herein if the patient presents with a diminished E2, LH, or FSH concentration, respectively (e.g., as assessed in a sample isolated from the patient), within about 4 days from the date of the first instance of administration of the GnRH antagonist to the patient. A patient may be administered, for example, a GnRH antagonist represented by formula (I) or (II) herein at a dosing schedule of, e.g., 100 mg/day or 200 mg/day, with or without add-back therapy. The patient is considered to present with a therapeutic phenotype of interest, such as a reduced E2 level (e.g., an E2 level of from 20 µg/ml to 50 µg/ml or less, such as an E2 level of less than 10 µg/ml) within about 4 days of administering the GnRH antagonist to the patient if the patient presents with the therapeutic phenotype of interest within about 4 days from the date of the first instance of administration of the GnRH antagonist represented by formula (I) or (II) to the patient.

DETAILED DESCRIPTION

Figure 1:
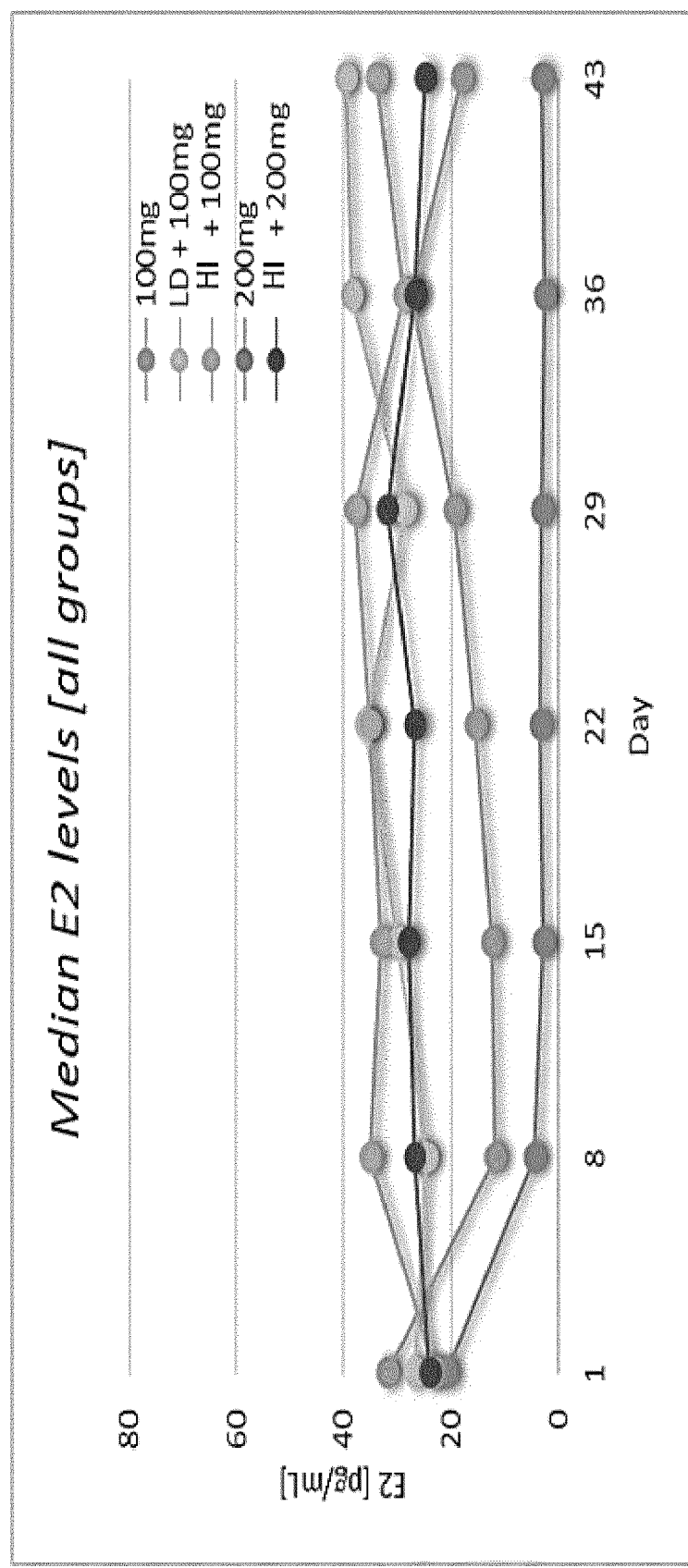
FIG. 1 is a graph demonstrating the effect of various doses of compound (II), with or without add-back therapy, on the median serum β17-estradiol concentration of healthy human female subjects over the course of a 43-day period, during which subjects were administered compound (II), with or without add-back therapy, once daily for 42 days, followed by a post-treatment monitoring period. Certain subjects received 100 mg/day or 200 mg/day of compound (II) as stand-alone therapeutics, while others received compound (II) in combination with 1.0 mg/day of β17-estradiol and 0.5 mg/day of norethindrone acetate (referred to throughout the figures as "HI" add-back therapy) or in combination with 0.5 mg/day of β17-estradiol and 0.1 mg/day of norethindrone acetate (referred to throughout the figures as "LD" add-back therapy). Data are shown in the following order, from bottom to top as observed at day 43: 200 mg of compound (II) alone, 100 mg of compound (II) alone, HI+200 mg of compound (II), HI+100 mg of compound (II), LD+100 mg of compound (II).

The invention features compositions and methods for reducing menstrual blood loss in a patient, such as a female human patient. The patient may be presenting with or diagnosed as having uterine fibroids, and may have an accompanying anemia, such as iron deficiency anemia due to the excessive loss of menstrual blood during the patient's menstrual cycle. Using the compositions and methods described herein, a gonadotropin-releasing hormone (GnRH) antagonist can be administered to a patient, such as a human female patient, according to a defined dosing regimen so as to reduce the loss of menstrual blood in the patient. GnRH antagonists suitable for use in conjunction with the compositions and methods described herein include thieno[3,4d]pyrimidine derivatives, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid and a pharmaceutically acceptable salt thereof, such as the choline salt thereof.

The GnRH antagonists described herein represent a useful therapeutic paradigm for the reduction of heavy menstrual bleeding, such as in uterine fibroids patients. For example, by attenuating the release of follicle-stimulating hormone (FSH) and luteinizing hormone (LH) from the anterior pituitary, the GnRH antagonists described herein can be used to suppress the production of estrogen, such as to below 20 µg/ml (e.g., to below 10 µg/ml). This reduction in endogenous serum estrogen concentration correlates with a reduction in menstrual blood loss, as described in Example 1, below. However, excessive hypoestrogenemia has been associated with the potentially harmful side effect of a reduction in bone mineral density (Barbieri, Am. J. Obstet. Gynecol. 166:740-745 (1992)). The invention is based in part on the discovery of dosing regimens for the administration of the GnRH antagonists 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid and a pharmaceutically acceptable salt thereof, such as the choline salt thereof, shown as compounds (I) and (II) below, that both effectively reduce menstrual blood loss in a patient and do not induce the deleterious side effect of reduced bone mineral density that has been observed with estrogen modulation.

Using the compositions and methods described herein, a patient may be treated with a GnRH antagonist, such as in an amount of about 100 mg per dose or about 200 mg per dose, for instance, at a dose of 100 mg/day or 200 mg/day, optionally in combination with add-back therapy. According to the dosing regimens described herein, for instance, a patient, such as a patient having uterine fibroids, may be treated with 100 mg or 200 mg of the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, as a stand-alone treatment, without a need for add-back therapy, to reduce the volume of menstrual blood lost by the patient without inducing a loss in bone mineral density. In another example, a patient may be treated with 100 mg/day or 200 mg/day of the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, in combination with add-back therapy to reduce the volume of menstrual blood lost by the patient without inducing a loss in bone mineral density.

In some embodiments, using the compositions and methods described herein, a patient, such as a human female patient presenting with or diagnosed as having uterine fibroids, may undergo a daily dosing schedule of the GnRH antagonist 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, at a dose of 100 mg/day or 200 mg/day. The treatment may be chronic, and may continue for one or more treatment cycles, such as a treatment cycle lasting 4 weeks, 6 weeks, 8 weeks, 12 weeks, 24 weeks, 48 weeks, or more.

3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid (Compound I)

3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, and the choline salt thereof, represented by formula (II), below are orally active, non-peptide GnRH antagonists. These compounds are capable of suppressing endogenous β17-estradiol (E2) concentrations and of significantly reducing menstrual blood loss in patients, such as patients presenting with and/or previously diagnosed as having uterine fibroids.

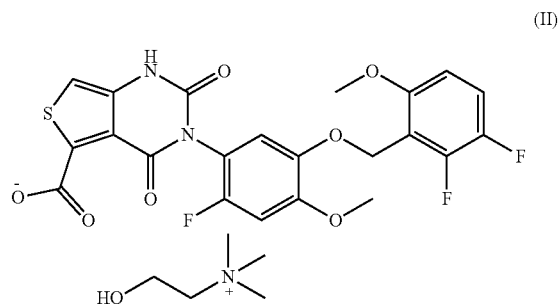

Compound (I) and pharmaceutically acceptable salts thereof, such as the choline salt thereof (compound (II)), can be synthesized, for example, using the methodology described in WO 2014/042176, the disclosure of which is incorporated herein by reference in its entirety. An exemplary synthetic scheme that may be used for the preparation of compound (I) and the choline salt thereof is shown in Scheme 1, below.

Scheme 1. Exemplary preparation of compound (I) and the choline salt thereof

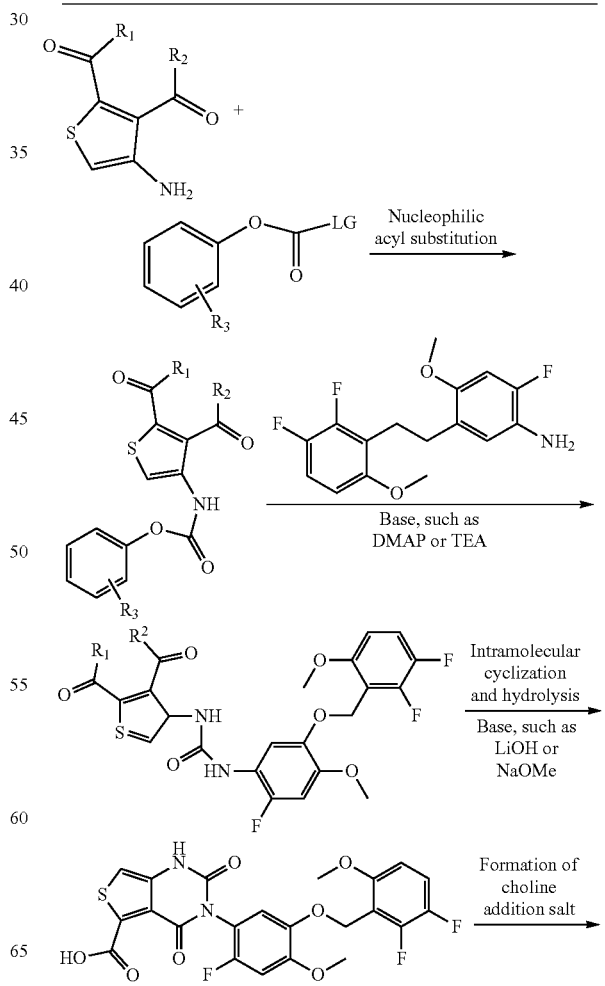

-continued

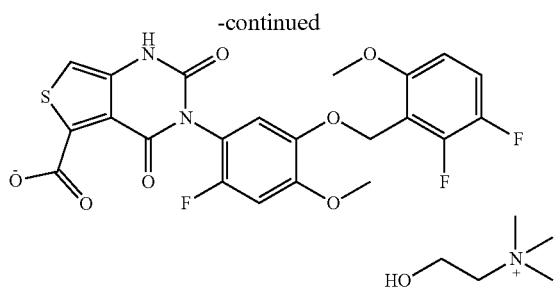

wherein $R_1$ and $R_2$ are each independently $C_{1-6}$ alkoxy groups; LG is a nucleofugal leaving group, such as chlorine or bromine, among others; $R_3$ represents an optional substituent, such as halogen, acyl group, $C_{1-6}$ alkyl group, or a nitro substituent; DMAP denotes N-dimethylaminopyridine; and TEA denotes trimethylamine.

Crystalline compound (II) has been characterized spectroscopically, for instance, in U.S. Pat. No. 9,169,266, the disclosure of which is incorporated herein by reference in its entirety. Several The foregoing crystalline form has been shown to exhibit characteristic X-ray powder diffraction peaks at about 7.1° 2θ, about 11.5° 2θ, about 19.4° 2θ, about 21.5° 2θ, about 22.0° 2θ, about 22.6° 2θ, about 23.5° 2θ, and about 26.2° 2θ. Additionally, this crystalline form exhibits $^{13}C$ solid-state nuclear magnetic resonance (NMR) peaks centered at about 55.5 ppm, about 57.1 ppm, about 58.7 ppm, about 69.8 ppm, about 98.1 ppm, about 110.3 ppm, about 111.6 ppm, about 113.7 ppm, about 118.0 ppm, about 145.3 ppm, about 149.8 ppm, and about 155.8 ppm. This crystalline form further exhibits $^{19}F$ solid-state NMR peaks centered at about −151.8 ppm, −145.2 ppm, and −131.6 ppm.

Compound (I), as well as pharmaceutically acceptable salts thereof, such as the choline salt thereof, exhibit a high affinity for human GnRH receptor (27.4 nM) and are capable of significantly suppressing serum LH concentration and E2 secretion. As described in Example 1, below, compound (I) and pharmaceutically acceptable salts thereof, including the choline salt thereof (compound (II)), are capable of inducing amenorrhea in human patients exhibiting menstrual blood loss without inducing a loss in bone mineral density, such as when administered at a dose of 100 mg/day as a stand-along therapeutic or in combination with add-back therapy, for instance, at a dose of 1.0 mg of E2 and 0.5 mg of norethindrone acetate and 0.5 mg of E2 and 0.1 mg of norethindrone acetate, as well as when administered a dose of 200 mg/day in combination with add-back therapy, such as a daily dosage of 1.0 mg of E2 and 0.5 mg of norethindrone acetate.

Using the compositions and methods described herein, a patient that is presenting with or has been diagnosed as having uterine fibroids may be treated with compound (I) or a pharmaceutically acceptable salt thereof, such as the choline salt thereof, daily, for instance, at a dose of 100 mg/day or 200 mg/day, optionally in combination with add-back therapy. In addition to having uterine fibroids, the patient may have an accompanying anemia, such as an iron deficiency anemia. As demonstrated by their ability to induce sustained amenorrhea in patients exhibiting heavy menstrual bleeding, compound (I) and pharmaceutically acceptable salts thereof, such as the choline salt (compound (II)), can be administered to a patient experiencing heavy menstrual bleeding and optionally having an accompanying anemia, such as iron deficiency anemia, according to a dosing regimen described herein. In this way, the treatment may induce a reduction in menstrual blood loss, and may concomitantly ameliorate the patient's anemia by curtailing further red blood cell deficiency.

Methods of Assessing Successful Treatment

Successful treatment of uterine fibroids using the compositions and methods described herein can be detected in a variety of clinical manifestations. In some embodiments, treatment of a patient having uterine fibroids may manifest in a finding that the patient exhibits a reduction in menstrual blood loss. The reduction may be, for example, from an initial value of 80 ml per menstrual cycle or more, which is indicative of heavy menstrual bleeding, to a reduced value of, for example, 60 ml, 55 ml, 50 ml, 45 ml, 40 ml, 35 ml, 30 ml, 25 ml, 20 ml, 15 ml, 10 ml, 5, ml, or less, of menstrual blood loss per menstrual cycle following the administration of a GnRH antagonist described herein. The reduction in menstrual blood loss may occur, for instance, within from about 3 days to about 52 weeks, from about 3 days to about 24 weeks, or from about 3 days to about 28 days of the first administration of the GnRH antagonist to the patient. This reduction in menstrual blood loss per menstrual cycle may occur, for instance, during the patient's final menstrual cycle of a 24-week treatment period.

Additional indicators of successful treatment of uterine fibroids in a patient include a finding that the patient exhibits a reduction in menstrual blood loss, for instance, of 25% or more by volume per menstrual cycle (e.g., a reduction in menstrual blood loss of 25%, 30%, 35%, 40%, 45%, 50%, 55%, 60%, 65%, 70%, 75%, 80%, 85%, 90%, 95%, 96%, 97%, 98%, 99%, 99.9%, 99.99%, or more (e.g., 100%) by volume per menstrual cycle) relative to a measurement of the volume of menstrual blood lost by the patient per menstrual cycle prior to the first administration of a GnRH antagonist described herein to the patient. For example, successful treatment of uterine fibroids may be signaled by a finding that the patient exhibits a reduction in menstrual blood loss of 50% or more by volume per menstrual cycle (e.g., a reduction in menstrual blood loss of 50%, 55%, 60%, 65%, 70%, 75%, 80%, 85%, 90%, 95%, 96%, 97%, 98%, 99%, 99.9%, 99.99%, or more (e.g., 100%) by volume per menstrual cycle) relative to a measurement of the volume of menstrual blood lost by the patient per menstrual cycle prior to the first administration of the GnRH antagonist to the patient The reduction in menstrual blood loss may occur, for instance, within from about 3 days to about 52 weeks, from about 3 days to about 24 weeks, or from about 3 days to about 28 days of the first administration of the GnRH antagonist to the patient. In some embodiments, the reduction in menstrual blood loss is observed within the last 28 days of a 24-week treatment period of the GnRH antagonist, such as 3-[2-fluoro-5-(2,3-difluoro-6-methoxybenzyloxy)-4-methoxyphenyl]-2,4-dioxo-1,2,3,4-tetrahydrothieno[3,4d]pyrimidine-5-carboxylic acid or a pharmaceutically acceptable salt thereof, such as the choline salt thereof.

Another significant clinical indicator of reduced menstrual blood loss and successful treatment of uterine fibroids is amenorrhea. Thus, in another example, uterine fibroids in a patient, such as a human female patient, may be considered to be treated using a dosing regimen described herein if the patient exhibits amenorrhea following administration of the GnRH antagonist to the patient. The amenorrhea may be sustained, for instance, for a period of at least about 5 days, at least about 7 days, at least about 10 days, at least about 4 weeks, at least about 8 weeks, at least about 12 weeks, at least about 16 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, or more, such as for a period of from about 5 days to about 52 weeks (e.g., about 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more).

The amenorrhea may occur, for instance, within from about 3 days to about 52 weeks, from about 3 days to about 24 weeks, or from about 3 days to about 28 days of the first administration of the GnRH antagonist to the patient. In some embodiments, successful treatment of uterine fibroids is signaled by an observation that the patient exhibits sustained amenorrhea within the last 28 days of a 24-week treatment period of the GnRH antagonist, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof.

Successful treatment of uterine fibroids may also manifest as a reduction in the number of days during a patient's menstrual cycle in which the patient exhibits menstrual bleeding, such as a reduction of from about 1% to about 100% (e.g., a reduction of from about 1 day to about 28 days in a 28-day menstrual cycle, such as a reduction of about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, or 28 days, or the entirety of the days in the patient's menstrual cycle). The reduction in the quantity of days in the patient's menstrual cycle in which the patient exhibits menstrual bleeding may be observed, for instance, within from about 3 days to about 52 weeks, from about 3 days to about 24 weeks, or from about 3 days to about 28 days of the first administration of the GnRH antagonist to the patient. The reduction in the quantity of days in the patient's menstrual cycle in which the patient exhibits menstrual bleeding may be observed, for example, during the patient's final menstrual cycle of a 24-week treatment period.

Additional clinical indicators of successful treatment of a patient having uterine fibroids include a finding that the patient exhibits an increase in serum hemoglobin concentration, for instance, of from about 1% to 100% or more, such as an increase of 1%; 2%, 3%, 4%, 5%, 6%, 7%, 8%, 9%, 10%, 11%; 12%, 13%, 14%, 15%, 16%, 17%, 18%, 19%, 20%, 21%; 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%; 52%, 53%, 54%, 55%, 56%, 57%, 58%, 59%, 60%, 61%; 62%, 63%, 64%, 65%, 66%, 67%, 68%, 69%, 70%, 71%; 72%, 73%, 74%, 75%, 76%, 77%, 78%, 79%, 80%, 81%; 82%, 83%, 84%, 85%, 86%, 87%, 88%, 89%, 90%, 91%; 92%, 93%, 94%, 95%, 96%, 97%, 98%, 99%; 100%, 200%, 500%, or more. The increase in serum hemoglobin may be observed, for instance, within from about 3 days to about 52 weeks, from about 3 days to about 24 weeks, or from about 3 days to about 28 days of the first administration of the GnRH antagonist to the patient. In some embodiments, the increase in serum hemoglobin is observed within 24 weeks of initiating treatment with the GnRH antagonist, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof.

Yet another clinical indicator of successful treatment of a patient having uterine fibroids is a finding that the patient exhibits a reduced serum concentration of β17-estradiol, FHS, and/or LH. For instance, successful treatment of uterine fibroids in a human patient may be signaled by a reduction in either of these substances by 10%, 15%, 20%, 25%, 30%, 35%, 40%, 45%, 50%, 55%, 60%, 65%, 70%, 75%, 80%, 85%, 90%, 95%, or more. Particularly, a finding that the serum β17-estradiol concentration in a human patient has decreased to less than 50 μg/ml, less than 20 μg/ml, less than 10 μg/ml, or less than 5 μg/ml, may serve as an indication that the patient has been successfully treated, and as an indication that the patient may exhibit a reduced volume of menstrual blood loss, for example, as described above.

Methods of Assessing Menstrual Blood Loss

Quantitation of Menstrual Blood Loss by the Alkaline Hematin Method

Techniques for quantifying menstrual blood loss are known in the art and include, for instance, the alkaline hematin method, as described, for instance, in Hallberg et al., Scand. J. Clin. Lab. Invest. 16:244-248 (1964), the disclosure of which is incorporated herein by reference as it pertains to techniques for assessing the volume of blood lost by a patient. In the alkaline hematin approach, menstrual blood soaked into, for example, a sanitary napkin, vaginal tampon, or cotton pad, is reconstituted in a basic aqueous solution, such as a solution of 5% (w/v) sodium hydroxide. This incubation enables (i) extraction of the iron-containing porphyrin of hemoglobin and (ii) oxidation of the ferrous ion to a hydroxy-coordinated ferric ion in each chelate, thus forming hematin. Hematin is a detectable chromophore, absorbing light at between 550 and 546 nm. By comparing the concentration of hematin obtained from incubation of a soaked menstrual blood sample with aqueous sodium hydroxide to the concentration of hematin obtained from incubation of venous blood with aqueous sodium hydroxide, one can stoichiometrically determine the volume of menstrual blood lost by a patient, such as a patient having uterine fibroids. Improvements to the original alkaline hematin method are known in the art and are described, for example, in Newton et al., Contraception 16:269-282 (1977), and in van Eijkeren et al., Eur. J. Obstet. Gynecol. Reprod. Biol. 22:345-351 (1986), the disclosures of each of which are incorporated herein by reference as they pertain to methods of determining the volume of menstrual blood lost by a patient.

Qualitative Measures of Suppressed Menstrual Blood Loss

In addition to quantifying menstrual blood loss, one of skill in the art can monitor menstrual blood loss qualitatively, such as by implementing a system in which patients undergoing treatment with a therapeutic agent, such as a GnRH antagonist as described herein, maintain a journal or other manual log of the relative degree of blood lost on a day-by-day basis. For instance, a patient may rank the quantity of blood lost using a qualitative scale in which blood lost is characterized as heavy, moderate, spotting, or no blood loss observed. By comparing a patient's daily assessment of qualitative blood lost, one of skill in the art can monitor the suppression of menstrual blood loss over a period of time, such as over the course of one or more treatment cycles during which a patient is administered a GnRH antagonist, such as -[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof.

Add-Back Therapy

Among the potential side-effects of GnRH antagonist therapy is a reduction in bone mineral density due to excessive depletion of estrogen (Newhall-Perry et al., American Journal of Obstetrics and Gynecology 173:824-829 (1995)). To combat this potential side effect, a patient undergoing GnRH antagonist therapy using the compositions and methods described herein can be administered add-back therapy. Add-back therapy may contain an estrogen (such as β17-estradiol, ethinyl estradiol, or a conjugated estrogen, such as a conjugated equine estrogen) optionally in combination with a progestin (such as norethindrone or an ester thereof, e.g., norethindrone acetate, or another agent such as progesterone, norgestimate, medroxyprogesterone, or drospirenone).

Endogenous estrogens are largely responsible for the development and maintenance of the female reproductive system and secondary sexual characteristics. Although circulating estrogens exist in a dynamic equilibrium of metabolic interconversions, estradiol is the principal intracellular human estrogen and is substantially more potent than its metabolites, estrone and estriol, at the receptor level. The primary source of estrogen in normally cycling adult women is the ovarian follicle, which secretes 70 to 500 μg of estradiol daily, depending on the phase of the menstrual cycle. After menopause, most endogenous estrogen is produced by conversion of androstenedione, secreted by the adrenal cortex, to estrone by peripheral tissues. Thus, estrone and the sulfate conjugated form, estrone sulfate, are the most abundant circulating estrogens in postmenopausal women. Circulating estrogens modulate the pituitary secretion of the gonadotropins, LH and FSH, through a negative feedback mechanism. Estrogens act to reduce the elevated levels of these hormones seen in postmenopausal women.

Progestin compounds, such as norethindrone and esters thereof (e.g., norethindrone acetate), as well as progesterone, norgestimate, medroxyprogesterone, and drospirenone, enhance cellular differentiation and generally oppose the actions of estrogens by decreasing estrogen receptor levels, increasing local metabolism of estrogens to less active metabolites, or inducing gene products that blunt cellular responses to estrogen. Progestins exert their effects in target cells by binding to specific progesterone receptors that interact with progesterone response elements in target genes. Progesterone receptors have been identified in the female reproductive tract, breast, pituitary, hypothalamus, and central nervous system. Progestins produce similar endometrial changes to those of the naturally occurring hormone progesterone. Progestins may be included in combination with estrogen in add-back therapy. For instance, according to the methods described herein, one can administer estrogen (e.g., E2) in conjunction with a progestin (e.g., norethindrone or an ester thereof, such as norethindrone acetate) to a patient undergoing GnRH antagonist therapy as to counteract the hypoestrogenemia that may be induced by the antagonist. In this way, add-back therapy can be used to mitigate or prevent potentially deleterious side effects, such as a reduction in bone mineral density.

Add-back therapy may be formulated for oral administration. For instance, add-back therapy administered in conjunction with the compositions and methods described herein may be formulated as a tablet, capsule, gel cap, powder, liquid solution, or liquid suspension. In some embodiments, the add-back therapy includes both an estrogen, such as β17-estradiol, and a progestin, such as norethindrone or norethindrone acetate. The estrogen and progestin may be administered separately or admixed in a single composition, such as a single tablet, capsule, gel cap, powder, liquid solution, or liquid suspension. For example, add-back therapy may feature a co-formulation containing estrogen (e.g., in the form of E2) and an additional agent such as a progestin (e.g., norethindrone or a compound that is metabolized in vivo to produce norethindrone, such as an ester of norethindrone that is de-esterified in vivo to produce norethindrone, for instance, norethindrone acetate). In some embodiments, add-back therapy is administered to a patient in the form of a single tablet, capsule, gel cap, powder, liquid solution, or liquid suspension that contains both estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate). In some embodiments, add-back therapy is administered as a fixed dose combination containing a GnRH antagonist, estrogen, and one or more additional agents, such as a progestin, in a single pharmaceutical composition. For instance, add-back therapy may be administered as a fixed dose combination of a GnRH antagonist, estrogen (e.g., in the form of E2) and a progestin (e.g., norethindrone or a compound that is metabolized in vivo to produce norethindrone, such as an ester of norethindrone that is de-esterified in vivo to produce norethindrone, for instance, norethindrone acetate) in the form of a single pharmaceutical composition, such as a single tablet, capsule, gel cap, powder, liquid solution, or liquid suspension.

Pharmaceutical Compositions

GnRH antagonists suitable for use with the compositions and methods described herein can be formulated into a pharmaceutical composition for administration to a patient, such as a female human patient, in a biologically compatible form suitable for administration in vivo. A pharmaceutical composition containing a GnRH antagonist, such as 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid or a pharmaceutically acceptable salt thereof, such as the choline salt thereof, may additionally contain a suitable diluent, carrier, or excipient. GnRH antagonists can be administered to a patient, for example, orally or by intravenous injection. Under ordinary conditions of storage and use, a pharmaceutical composition may contain a preservative, e.g., to prevent the growth of microorganisms. Conventional procedures and ingredients for the selection and preparation of suitable formulations are described, for example, in Remington: The Science and Practice of Pharmacy (2012, $22^{nd}$ ed.) and in The United States Pharmacopeia: The National Formulary (2015, USP 38 NF 33).

Pharmaceutical compositions may include sterile aqueous solutions, dispersions, or powders, e.g., for the extemporaneous preparation of sterile solutions or dispersions. In all cases the form may be sterilized using techniques known in the art and may be fluidized to the extent that may be easily administered to a patient in need of treatment.

A pharmaceutical composition may be administered to a patient, e.g., a human patient, alone or in combination with one or more pharmaceutically acceptable carriers, e.g., as described herein, the proportion of which may be determined by the solubility and/or chemical nature of the compound, chosen route of administration, and standard pharmaceutical practice.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regards as their invention.

Example 1. Evaluation of the Effects of choline 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylate on Serum Estradiol and Menstrual Blood Loss in Human Female Subjects Subject Population and Study Design To assess the effects of compound (II) on serum β17-estradiol concentration and menstrual blood loss, a total of 75 healthy human female subjects were divided into five treatment groups, as described in Table 1, below. The subjects were screened for a period of four weeks prior to the commencement of treatment with compound (II). At the conclusion of the four week screening period, the subjects in each treatment arm were administered an equivalent dosage of norethindrone acetate of 5 mg×3 times daily. This 15 mg/day dosage was administered for a total of 11 days so as to allow synchronization of menses among the subjects. The subjects were subsequently not treated for the ensuing 4 days. Following this withdrawal period, the subjects were treated with compound (II), with or without add-back therapy, once daily for 42 days according to the dosages set forth in Table 1. Following the 42-day treatment cycle, the subjects were further monitored for a period of 13 days.

TABLE 1

Treatment arms of subjects receiving choline 3-[2-fluoro-5-(2,3-difluoro-6-methoxybenzyloxy)-4-methoxyphenyl]-2,4-dioxo-1,2,3, 4-tetrahydrothieno [3,4d]pyrimidine-5-carboxylate

| Treatment Arm | Dosage of Compound (II) | Add-back Therapy |
|---|---|---|
| 1 | 100 mg/day | None |
| 2 | 100 mg/day | 1.0 mg/day of β17-estradiol + 0.5 mg/day of norethindrone acetate |
| 3 | 100 mg/day | 0.5 mg/day of β17-estradiol + 0.1 mg/day of norethindrone acetate |
| 4 | 200 mg/day | None |
| 5 | 200 mg/day | 1.0 mg/dayof β17-estradiol + 0.5 mg/day of norethindrone acetate |

As used herein, the add-back regime of 1.0 mg/day β17-estradiol and 0.5 mg/day norethindrone acetate is referred to as the "high-dose" or "HI" add-back dosage, while the add-back regime of 0.5 mg/day β17-estradiol and 0.1 mg/day norethindrone acetate was referred to as the "low-dose" or "LD" add-back dosage. This labeling convention is used throughout this Example and is additionally referred to in the Figures.

Figure 2:
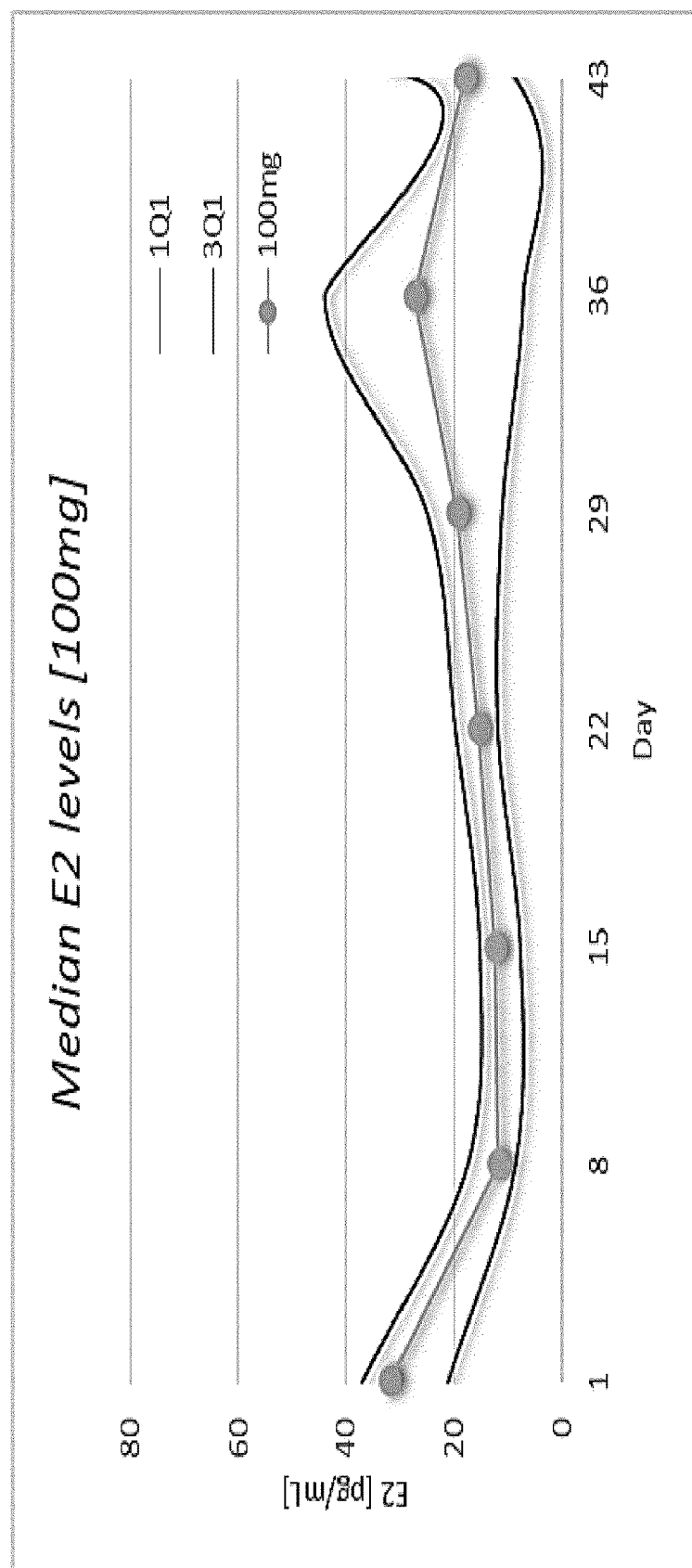
FIG. 2 is a graph demonstrating the effect of 100 mg/day of compound (II), without add-back therapy, on the median serum β17-estradiol concentration of healthy human female subjects over the course of a 43-day period, during which subjects were administered compound (II) once daily for 42 days, followed by a post-treatment monitoring period. The lower quartile is indicated as "1Q1," and the upper quartile is indicated as "3Q1."
Figure 3:
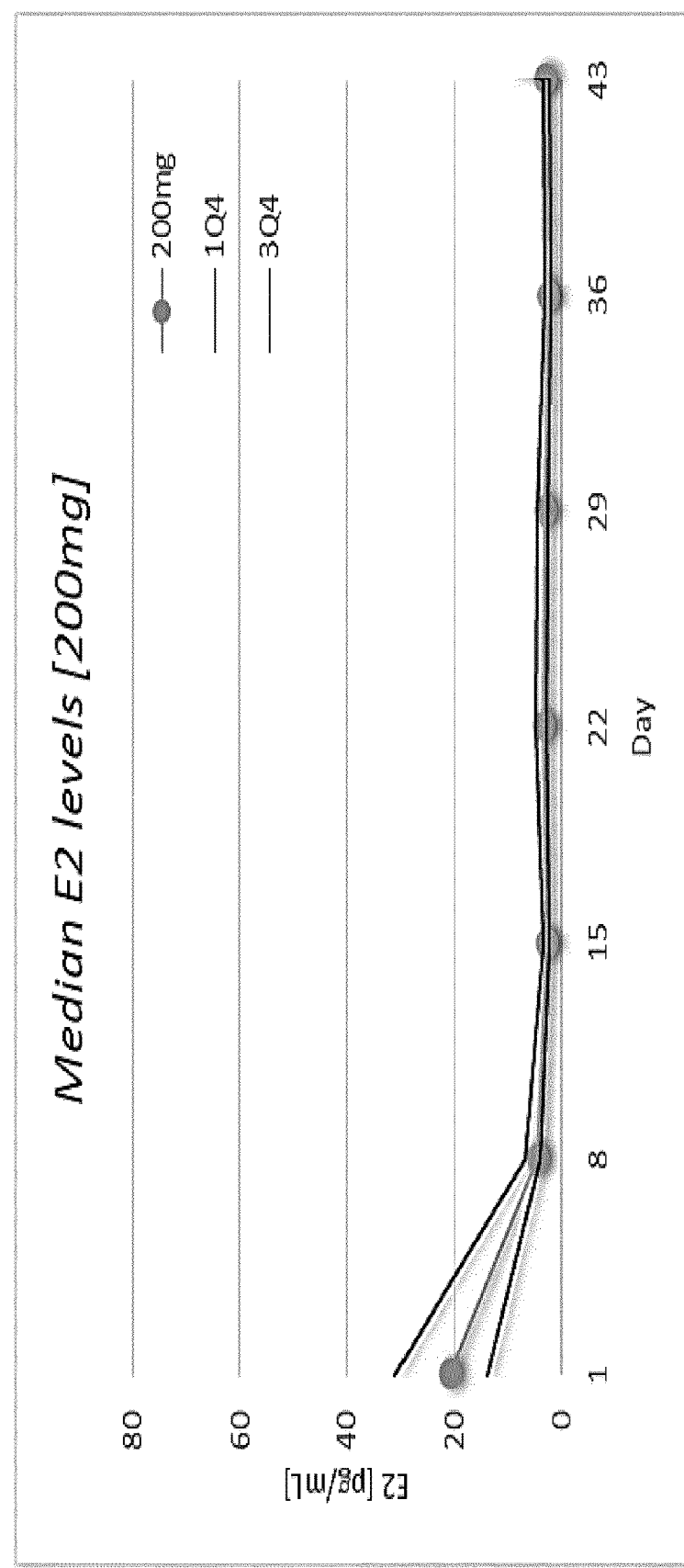
FIG. 3 is a graph demonstrating the effect of 200 mg/day of compound (II), without add-back therapy, on the median serum β17-estradiol concentration of healthy human female subjects over the course of a 43-day period, during which subjects were administered compound (II) once daily for 42 days, followed by a post-treatment monitoring period. The lower quartile is indicated as "1Q4," and the upper quartile is indicated as "3Q4."
Figure 4:
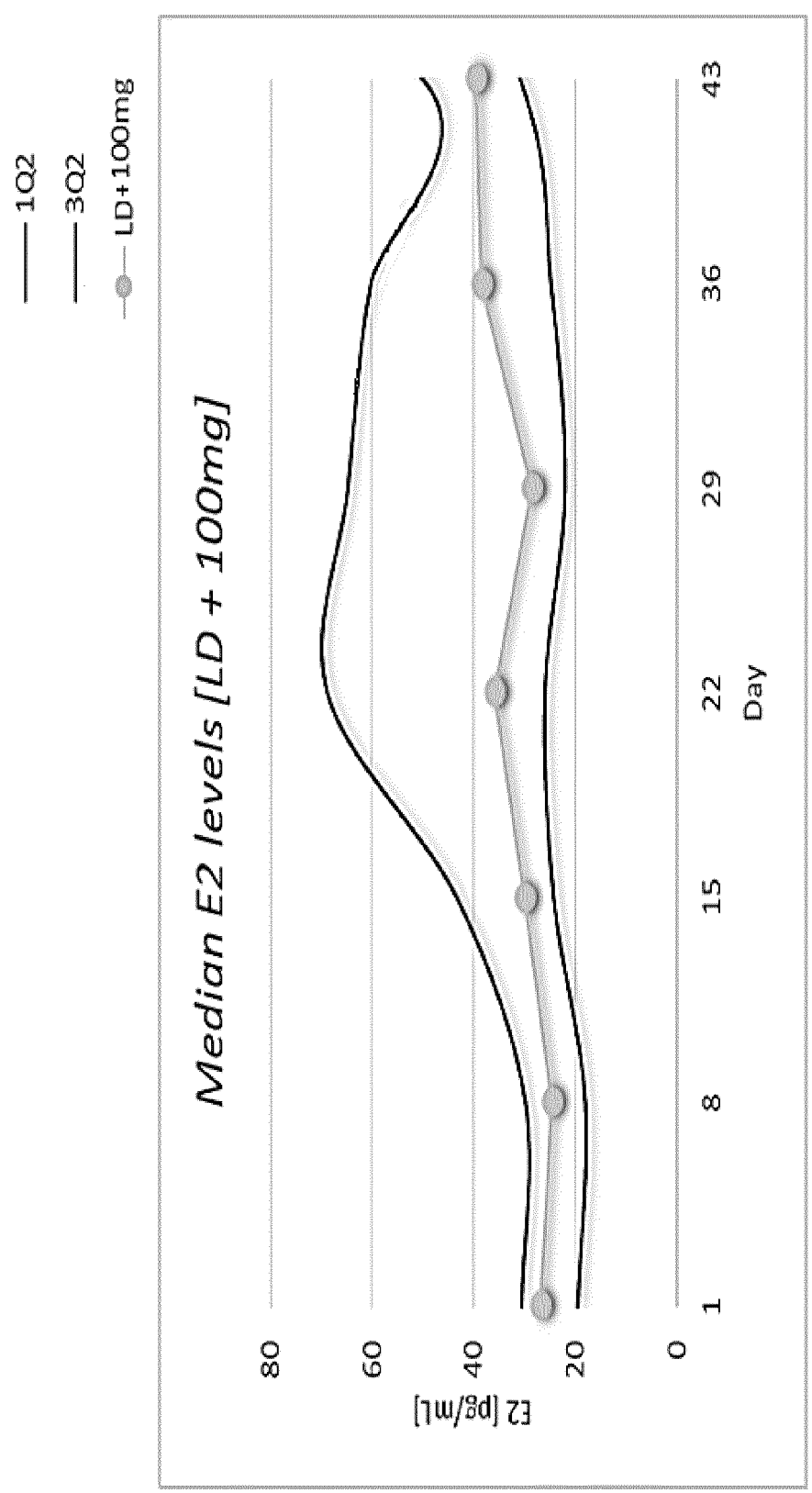
FIG. 4 is a graph demonstrating the effect of 100 mg/day of compound (II), in combination with 0.5 mg/day of β17-estradiol and 0.1 mg/day of norethindrone acetate, on the median serum β17-estradiol concentration of healthy human female subjects over the course of a 43-day period, during which subjects were administered compound (II) and the add-back therapy once daily for 42 days, followed by a post-treatment monitoring period. The lower quartile is indicated as "1Q2," and the upper quartile is indicated as "3Q2."
Figure 5:
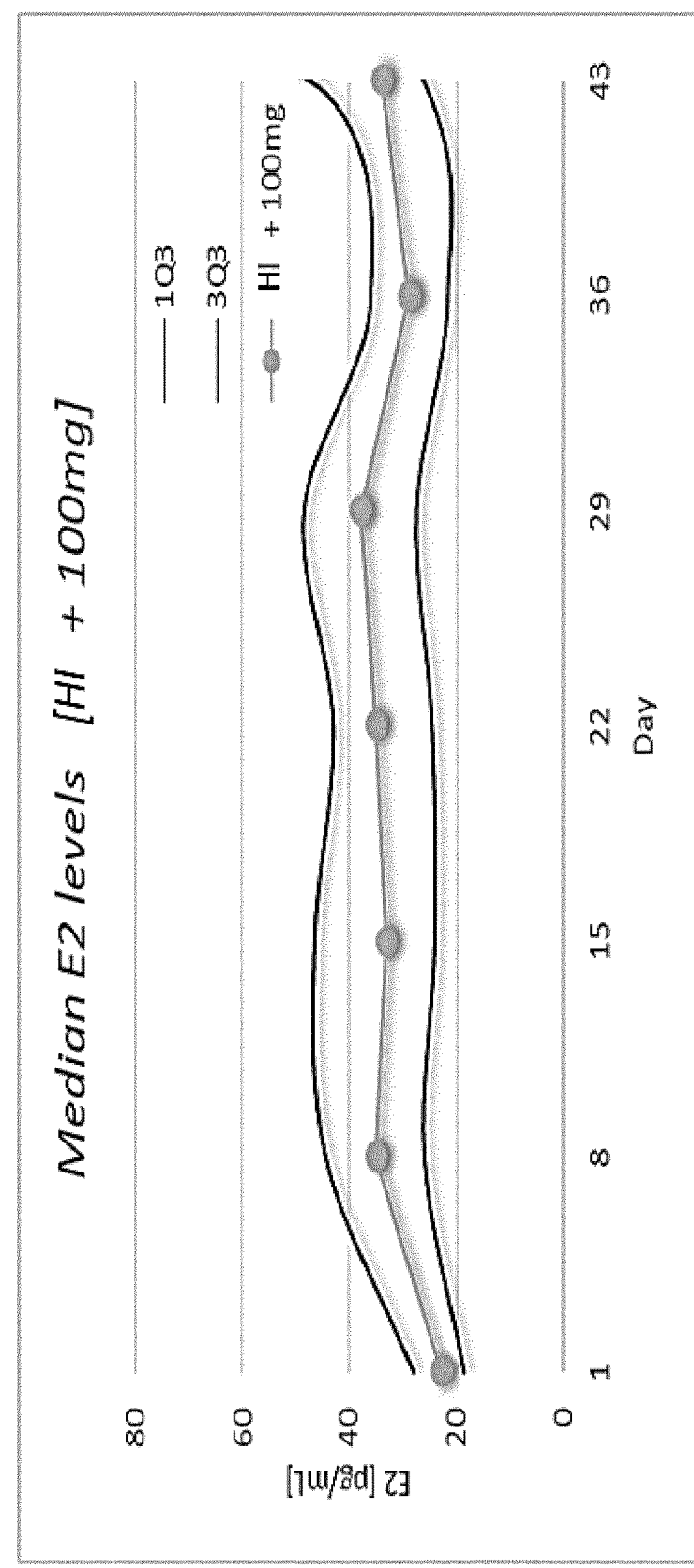
FIG. 5 is a graph demonstrating the effect of 100 mg/day of compound (II), in combination with 1.0 mg/day of β17-estradiol and 0.5 mg/day of norethindrone acetate, on the median serum β17-estradiol concentration of healthy human female subjects over the course of a 43-day period, during which subjects were administered compound (II) and the add-back therapy once daily for 42 days, followed by a post-treatment monitoring period. The lower quartile is indicated as "1Q3," and the upper quartile is indicated as "3Q3."
Figure 6:
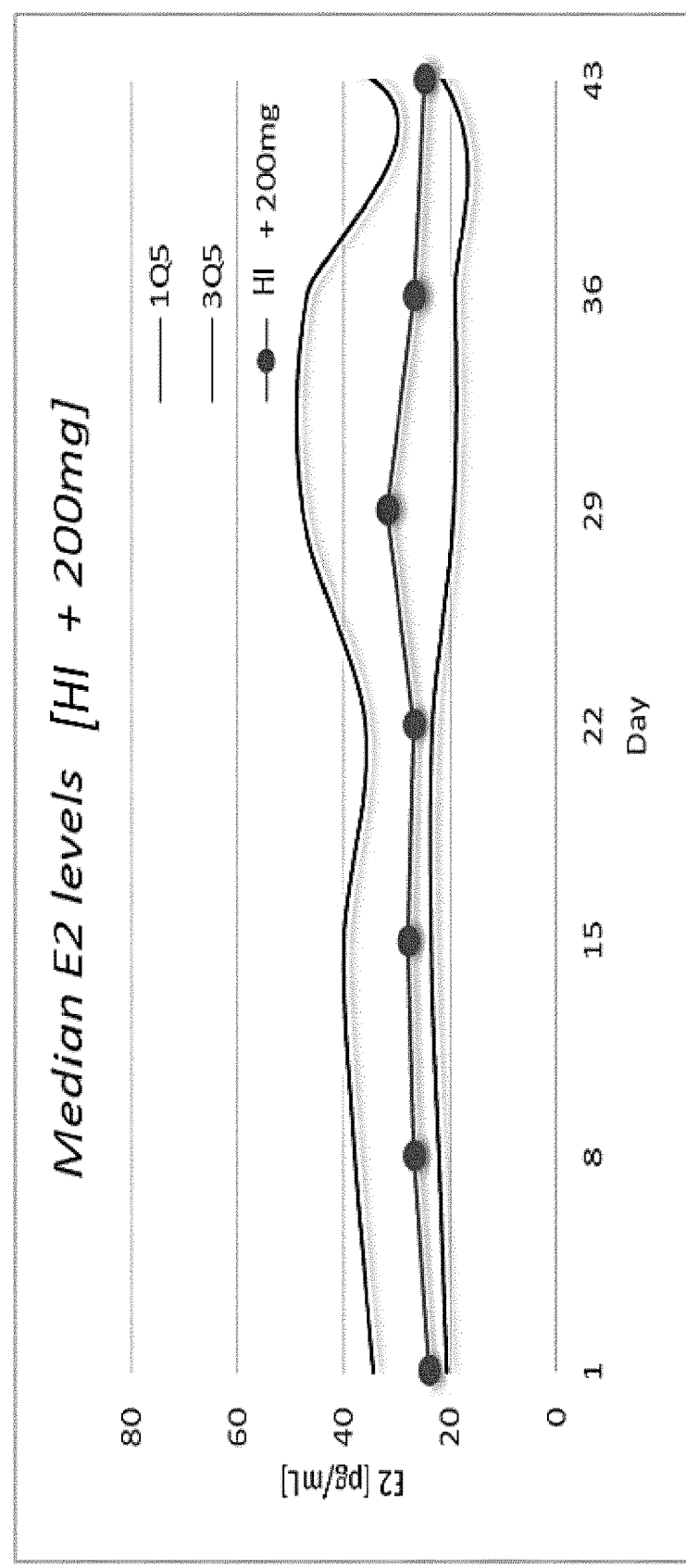
FIG. 6 is a graph demonstrating the effect of 200 mg/day of compound (II), in combination with 1.0 mg/day of β17-estradiol and 0.5 mg/day of norethindrone acetate, on the median serum β17-estradiol concentration of healthy human female subjects over the course of a 43-day period, during which subjects were administered compound (II) and the add-back therapy once daily for 42 days, followed by a post-treatment monitoring period. The lower quartile is indicated as "1Q5," and the upper quartile is indicated as "3Q5."
Figure 7:
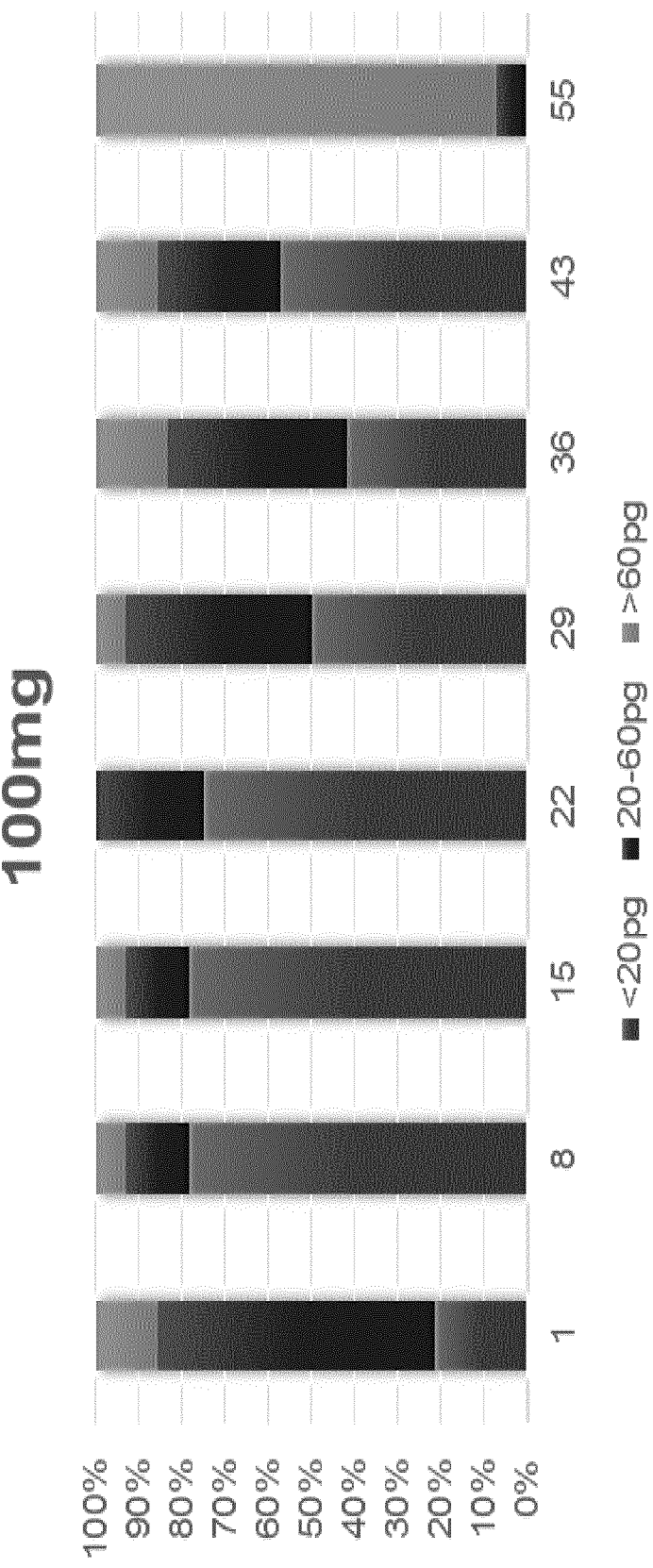
FIG. 7 is a graph demonstrating the distribution of serum β17-estradiol levels among human female subjects that received 100 mg/day of compound (II) without add-back therapy over the course of a 42-day treatment period, followed by a 13-day post-treatment period in which subjects were monitored, but were not administered a therapeutic agent. Shaded regions of each bar correspond to the following serum β17-estradiol levels, from the top of each bar to the bottom: >60 pg/ml, 20-60 pg/ml, and <20 pg/ml.
Figure 8:
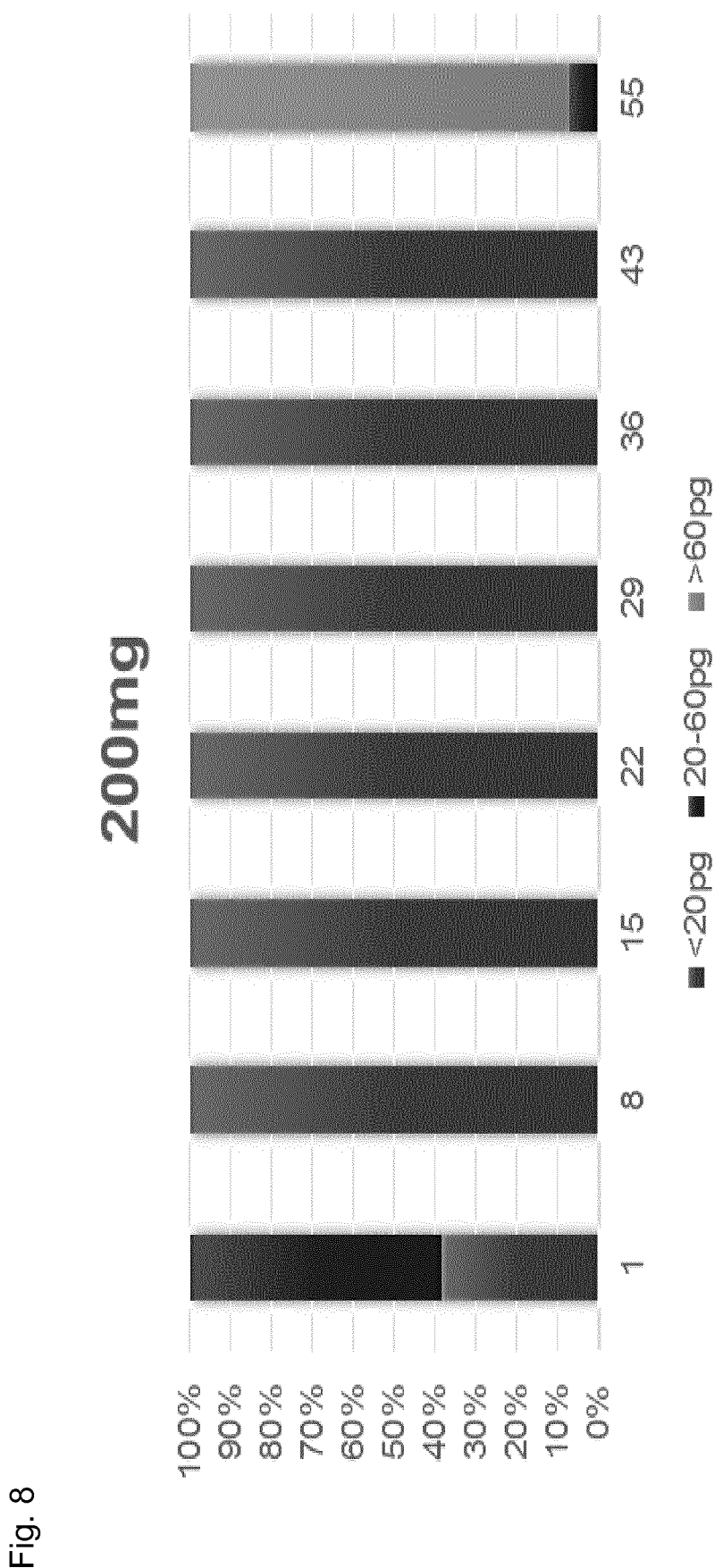
FIG. 8 is a graph demonstrating the distribution of serum β17-estradiol levels among human female subjects that received 200 mg/day of compound (II) without add-back therapy over the course of a 42-day treatment period, followed by a 13-day post-treatment period in which subjects were monitored, but were not administered a therapeutic agent. Shaded regions of the bar at day 1 correspond to the following serum β17-estradiol levels, from the top of the bar to the bottom: 20-60 pg/ml and <20 pg/ml. Shaded regions of the bar at day 55 correspond to the following serum β17-estradiol levels, from the top of the bar to the bottom: >60 pg/ml and 20-60 pg/ml.
Figure 9:
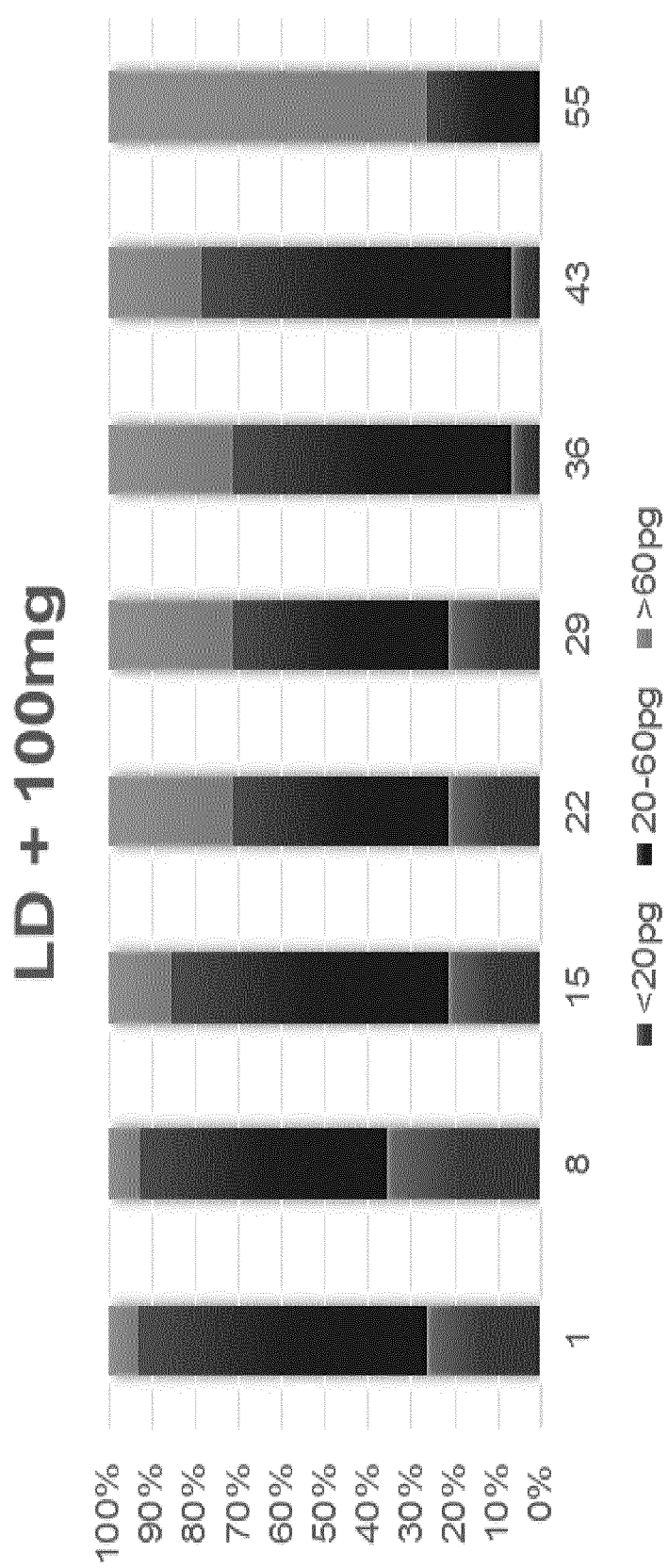
FIG. 9 is a graph demonstrating the distribution of serum β17-estradiol levels among human female subjects that received 100 mg/day of compound (II) in combination with 0.5 mg/day of 617-estradiol and 0.1 mg/day of norethindrone acetate over the course of a 42-day treatment period, followed by a 13-day post-treatment period in which subjects were monitored, but were not administered a therapeutic agent. Shaded regions of each bar correspond to the following serum β17-estradiol levels, from the top of each bar to the bottom: >60 pg/ml, 20-60 pg/ml, and <20 pg/ml.
Figure 10:
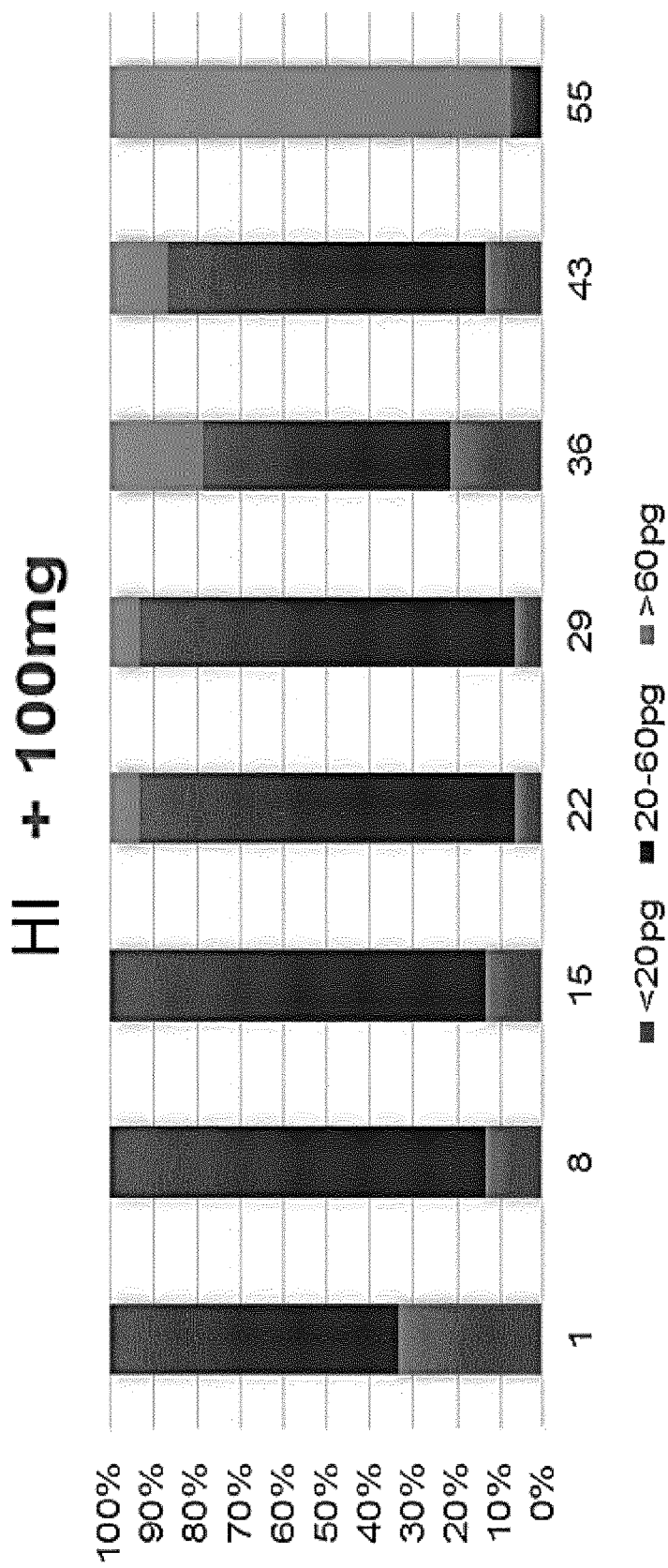
FIG. 10 is a graph demonstrating the distribution of serum β17-estradiol levels among human female subjects that received 100 mg/day of compound (II) in combination with 1.0 mg/day of 617-estradiol and 0.5 mg/day of norethindrone acetate over the course of a 42-day treatment period, followed by a 13-day post-treatment period in which subjects were monitored, but were not administered a therapeutic agent. Shaded regions of each bar generally correspond to the following serum β17-estradiol levels, from the top of each bar to the bottom: >60 pg/ml, 20-60 pg/ml, and <20 pg/ml.
Figure 11:
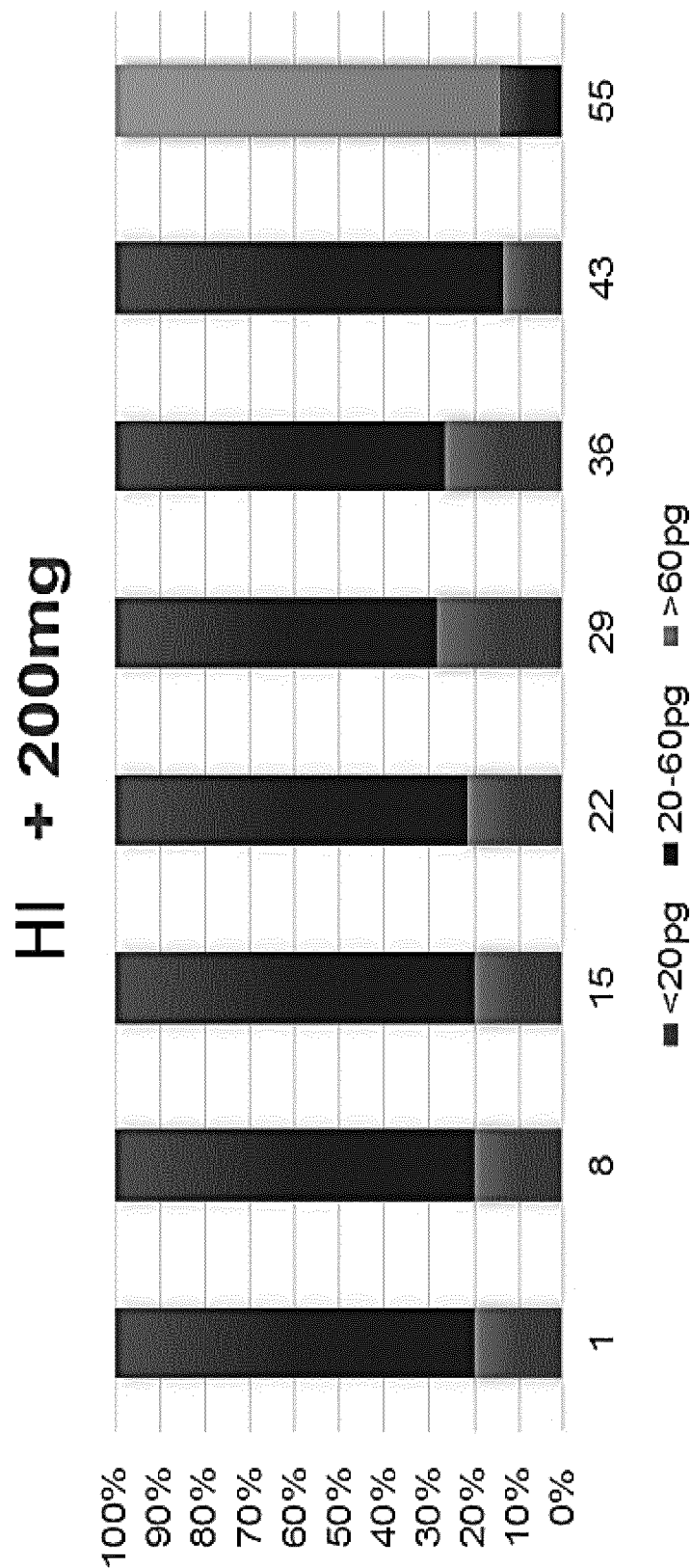
FIG. 11 is a graph demonstrating the distribution of serum β17-estradiol levels among human female subjects that received 200 mg/day of compound (II) in combination with 1.0 mg/day of 617-estradiol and 0.5 mg/day of norethindrone acetate over the course of a 42-day treatment period, followed by a 13-day post-treatment period in which subjects were monitored, but were not administered a therapeutic agent. Shaded regions of each bar generally correspond to the following serum β17-estradiol levels, from the top of each bar to the bottom: >60 pg/ml, 20-60 pg/ml, and <20 pg/ml.
Figure 12:
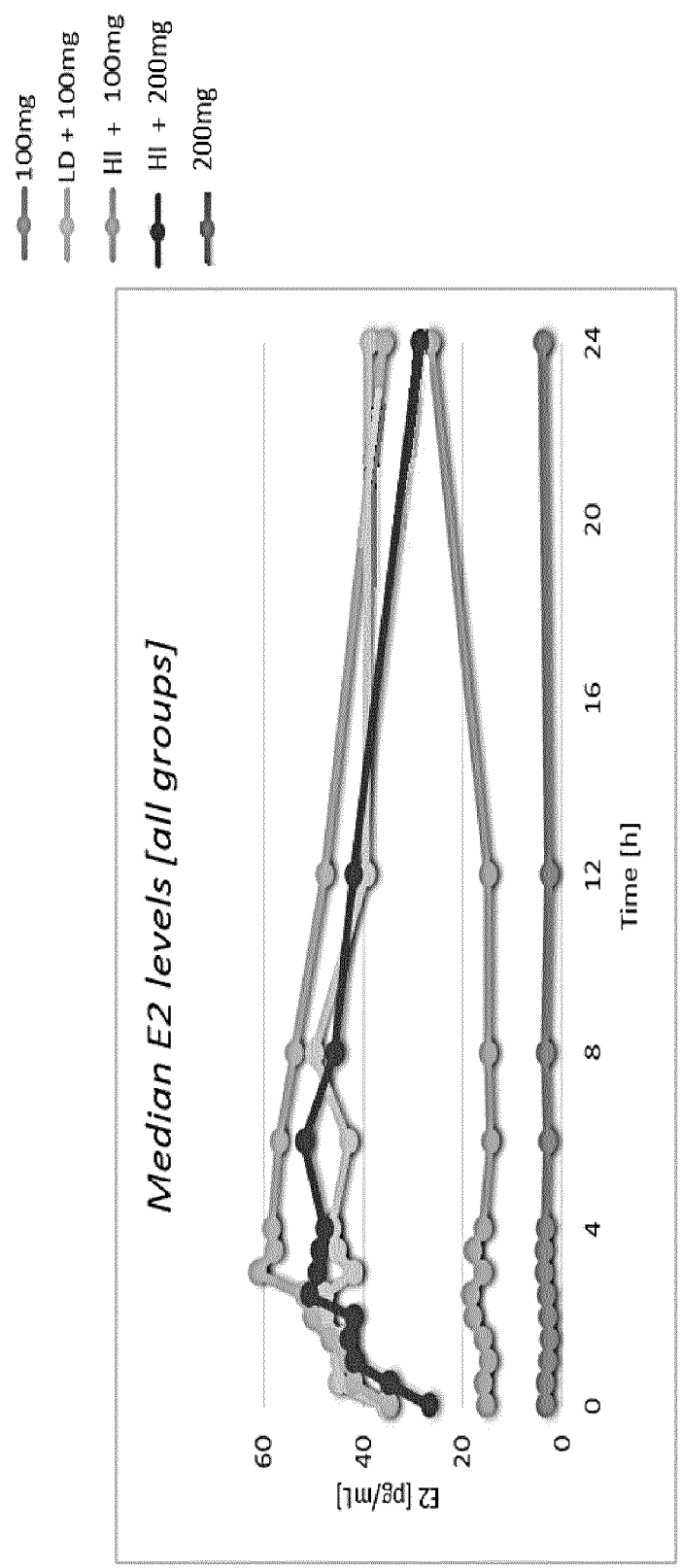
FIG. 12 is a graph demonstrating the effect of various doses of compound (II), with or without add-back therapy, on the median serum β17-estradiol concentration of healthy human female subjects over the course of a 24-hour period. The measurements shown in FIG. 12 were recorded on day 23 of a 42-day treatment schedule in which subjects were administered compound (II) once daily, with or without add-back therapy, at the indicated dosages. Data are shown in the following order, from bottom to top as observed at day 24: 200 mg of compound (II) alone, 100 mg of compound (II) alone, HI+200 mg of compound (II), HI+100 mg of compound (II), LD+100 mg of compound (II).
Figure 13:
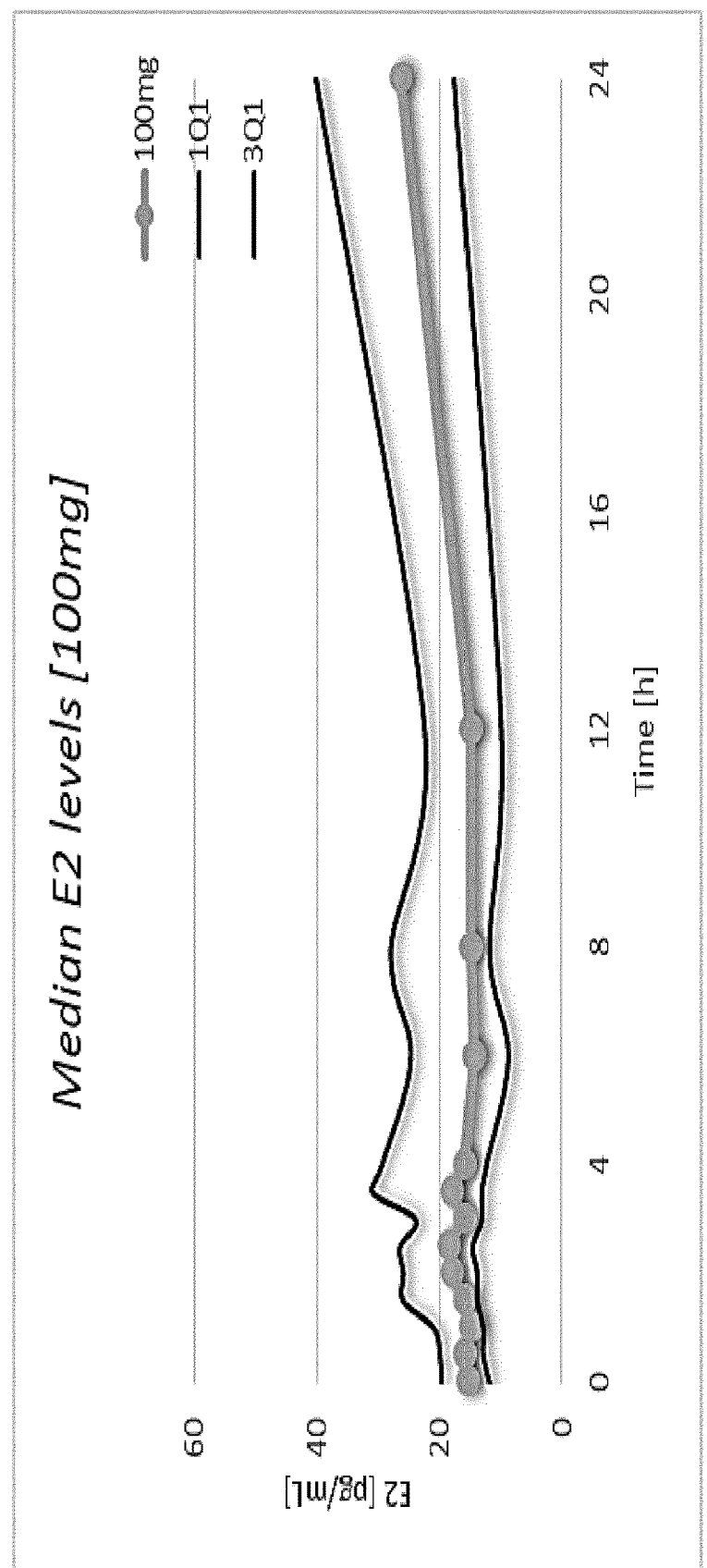
FIG. 13 is a graph demonstrating the effect of 100 mg/day of compound (II), without add-back therapy, on the median serum β17-estradiol concentration of healthy human female subjects over the course of a 24-hour period on day 23 of a 42-day treatment schedule in which subjects were administered compound (II) once daily. The lower quartile is indicated as "1Q1," and the upper quartile is indicated as "3Q1."
Figure 14:
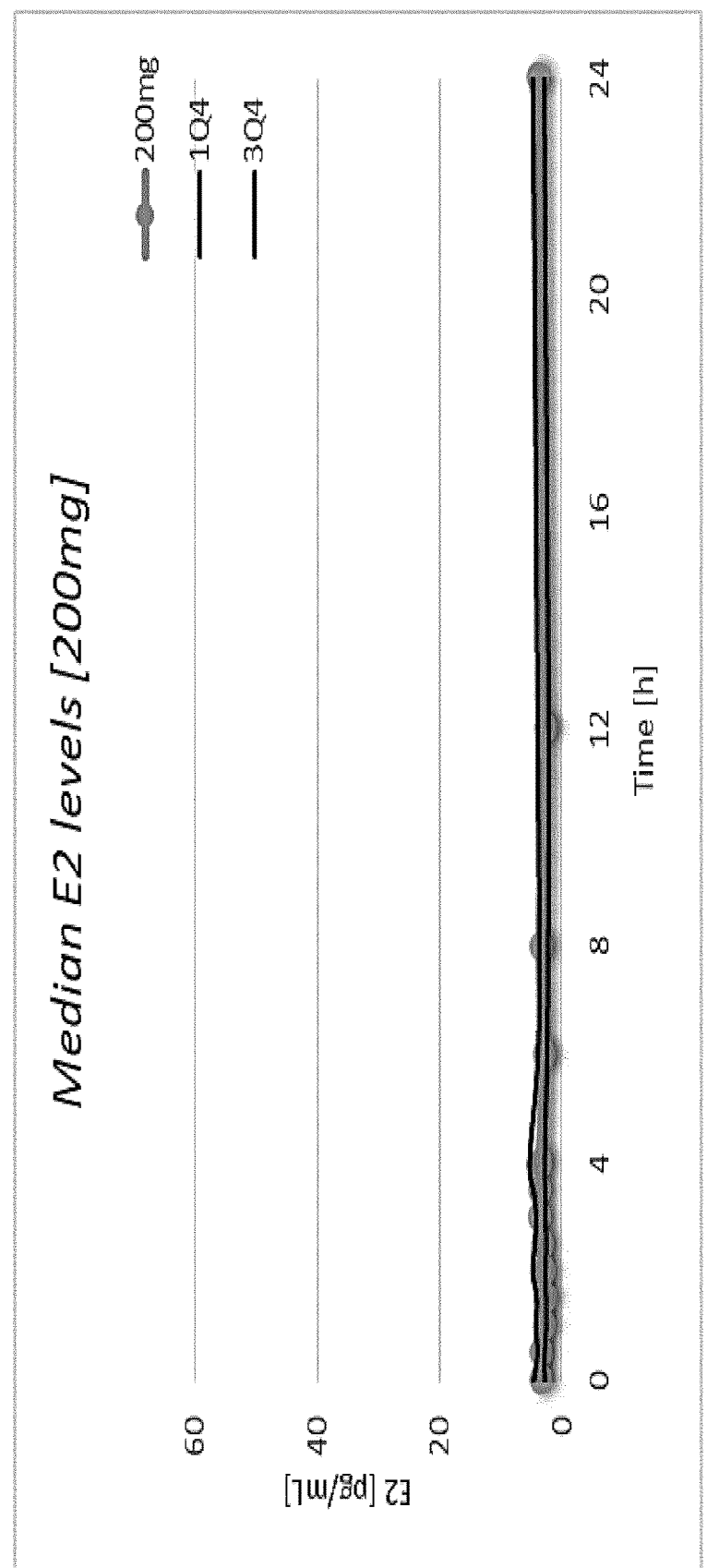
FIG. 14 is a graph demonstrating the effect of 200 mg/day of compound (II), without add-back therapy, on the median serum β17-estradiol concentration of healthy human female subjects over the course of a 24-hour period on day 23 of a 42-day treatment schedule in which subjects were administered compound (II) once daily. The lower quartile is indicated as "1Q4," and the upper quartile is indicated as "3Q4."
Figure 15:
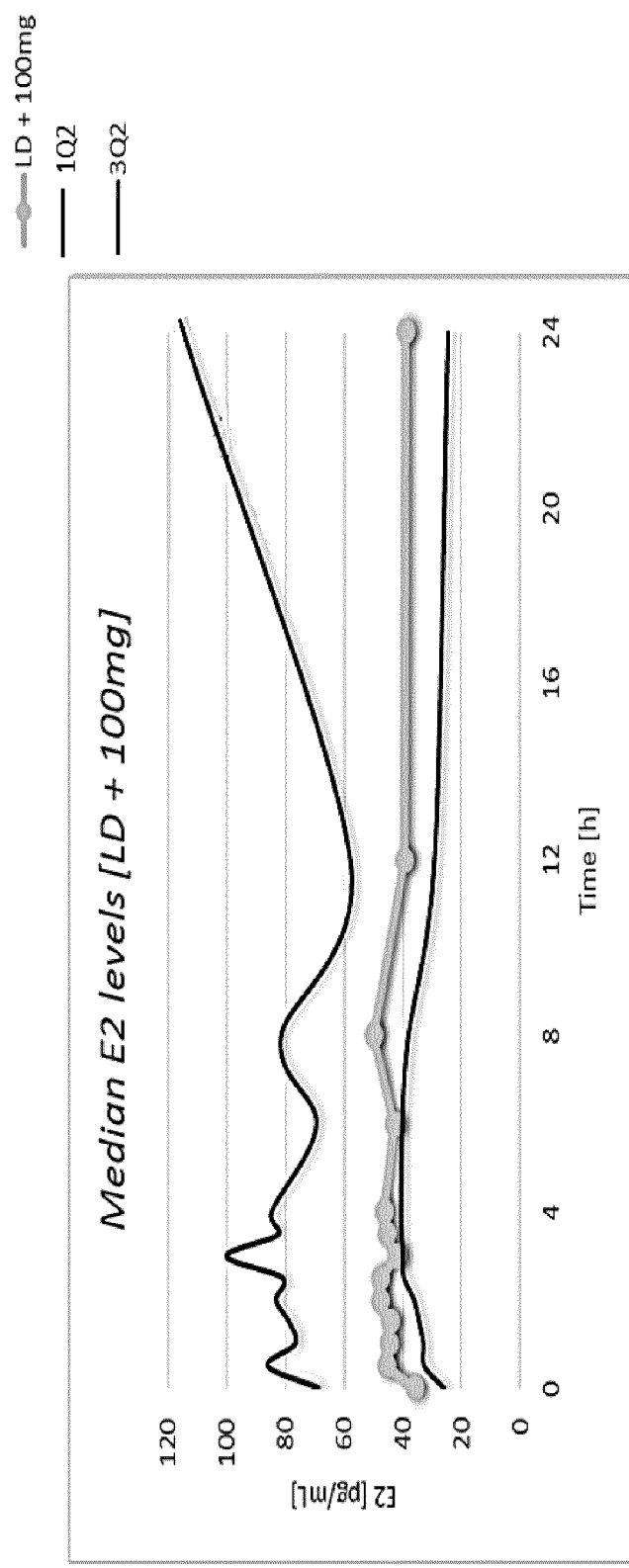
FIG. 15 is a graph demonstrating the effect of 100 mg/day of compound (II), in combination with 0.5 mg/day of β17-estradiol and 0.1 mg/day of norethindrone acetate, on the median serum β17-estradiol concentration of healthy human female subjects over the course of a 24-hour period on day 23 of a 42-day treatment schedule in which subjects were administered compound (II) and the add-back therapy once daily. The lower quartile is indicated as "1Q2," and the upper quartile is indicated as "3Q2."
Figure 16:
FIG. 16 is a graph demonstrating the effect of 100 mg/day of compound (II), in combination with 1.0 mg/day of β17-estradiol and 0.5 mg/day of norethindrone acetate, on the median serum β17-estradiol concentration of healthy human female subjects over the course of a 24-hour period on day 23 of a 42-day treatment schedule in which subjects were administered compound (II) and the add-back therapy once daily. The lower quartile is indicated as "1Q3," and the upper quartile is indicated as "3Q3."
Figure 17:
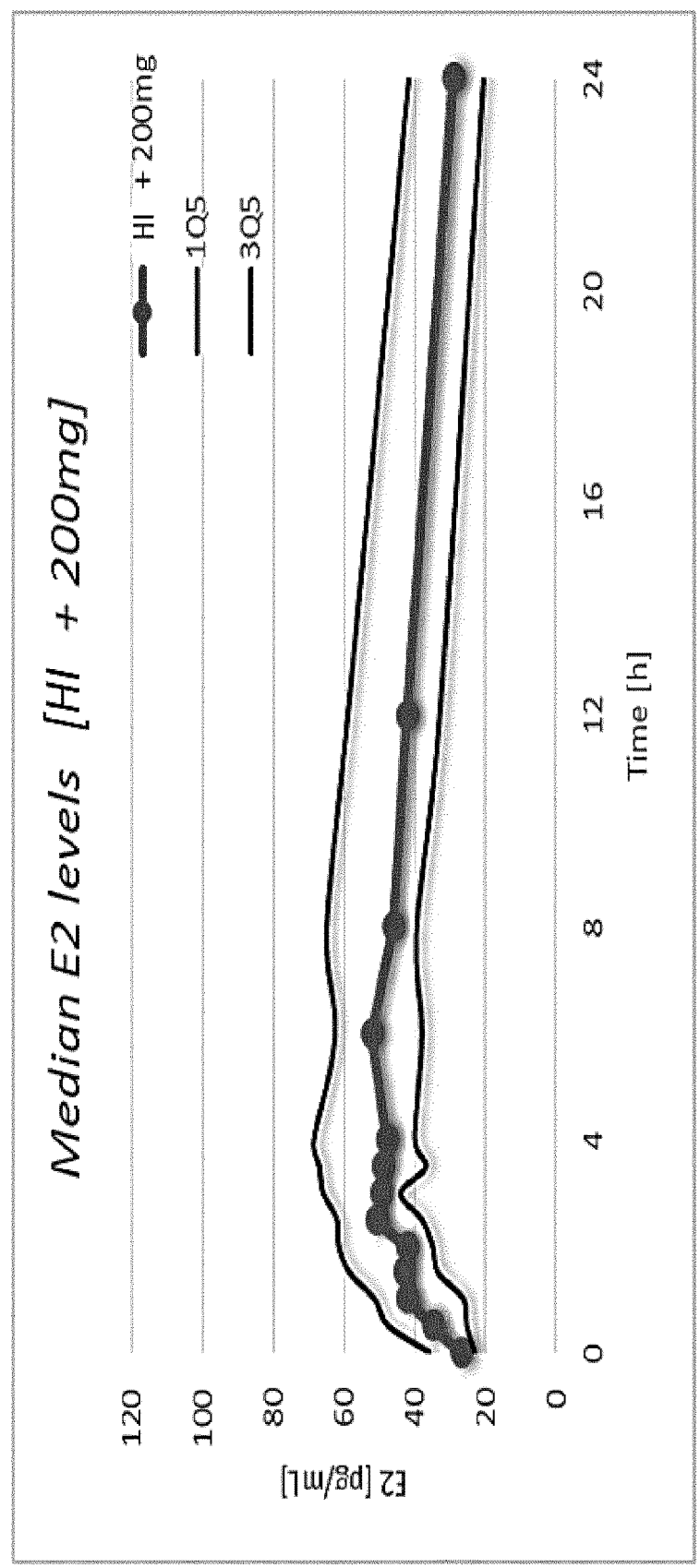
FIG. 17 is a graph demonstrating the effect of 200 mg/day of compound (II), in combination with 1.0 mg/day of β17-estradiol and 0.5 mg/day of norethindrone acetate, on the median serum β17-estradiol concentration of healthy human female subjects over the course of a 24-hour period on day 23 of a 42-day treatment schedule in which subjects were administered compound (II) and the add-back therapy once daily. The lower quartile is indicated as "1Q5," and the upper quartile is indicated as "3Q5."

Effects of choline 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylate on Serum Estradiol Upon evaluation of each subject's β17-estradiol (E2) levels over the course of the 42-day treatment cycle, a reduction in serum E2 concentration was observed as a function of the quantity of compound (II) administered to the subjects. As shown in FIG. 1, median serum E2 levels were reduced in a dose-dependent manner, and the median serum E2 levels observed for all add-back regimes were within about 20 µg/ml to about 40 µg/ml. Further, FIGS. 2, 4, and 5 demonstrate that, when administered at a dose of 100 mg/day with or without add-back therapy, compound (II) exhibited a low variability in reducing serum E2 concentrations. As shown in FIG. 3, when administered at a dose of 200 mg/day in the absence of add-back therapy, compound (II) exhibited no substantial variability in suppressing serum E2 concentrations. When compound (II) was administered in combination with 1.0 mg E2 and 0.5 mg norethindrone acetate, median serum E2 levels were suppressed to between 25 µg/ml and 32 µg/ml (FIG. 6). This dose-dependent and low-variable reduction in serum E2 is also manifest in FIGS. 30-34, which display the serum E2 concentrations of every subject in each treatment arm of this investigation.

FIGS. 7-11 provide a graphical display of the proportion of subjects that exhibited a serum E2 concentration of less than 20 µg/ml, from 20 µg/ml to 60 µg/ml, and greater than 60 µg/ml throughout the 42-day treatment cycle. A dose-dependent reduction is again manifest, as all subjects in the 200 mg/day compound (II) stand-alone treatment arm exhibited serum E2 concentrations of less than 20 µg/ml on each of days 8, 15, 22, 29, and 36 of the treatment period. Among subjects treated with 100 mg/day of compound (II) in the absence of add-back therapy, the majority of subjects exhibited E2 levels of less than 20 µg/ml on each of days 8, 15, and 22 of the treatment period.

In addition to reducing serum E2 concentrations over the course of the 42-day treatment cycle, compound (II) induced a dose-dependent reduction in serum E2 levels over a 24-hour period starting from the first administration of the compound. As was observed over the course of the full treatment cycle, the reduction in serum E2 over a 24-hour window occurred in a dose-dependent fashion (FIGS. 12-17) and was generally characterized by low variability.

Effects of choline 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylate on Menstrual Blood Loss To assess the effects of compound (II) on menstrual blood loss, the volume of menstrual blood lost by each subject was evaluated over the course of the entirety of the study, including the 11-day screening period, 4-day withdrawal period, 42-treatment period, and 13-day post-treatment evaluation period. Assessment of menstrual blood loss was conducted using an electronic diary method, as subjects recorded daily whether their bleeding for each day was heavy, moderate, or light spotting.

As shown in FIGS. 20-24, compound (II) was capable of inducing sustained amenorrhea, indicative of suppression of menstrual blood loss.

Among subjects in the 100 mg/day compound (II) stand-alone arm, amenorrhea was observed in at least 86% of subjects (12/14 subjects) during the last 4 weeks of treatment, and no bleeding or spotting was observed in at least 93% of subjects (13/14 subjects) during the final 4 weeks of treatment. Among subjects in the 100 mg/day compound (II) arm that also received 0.5 mg E2 and 0.1 mg norethindrone acetate, amenorrhea was observed in at least 21% of subjects (3/14 subjects) during the last 4 weeks of treatment, and no bleeding or spotting was observed in at least 57% of subjects (8/14 subjects) during the final 4 weeks of treatment. Among subjects in the 100 mg/day compound (II) arm that also received 1.0 mg E2 and 0.5 mg norethindrone acetate, amenorrhea was observed in at least 53% of subjects (8/15 subjects) during the last 4 weeks of treatment, and no bleeding or spotting was observed in at least 93% of subjects (14/15 subjects) during the final 4 weeks of treatment. Thus, surprisingly, among subjects that were administered 100 mg/day of compound (II), those subjects that received the higher dosage of add-back therapy (1.0 mg/day of E2 and 0.5 mg/day of norethindrone acetate) exhibited a more sustained reduction in menstrual blood loss relative to those subjects that were administered the lower dosage of add-back therapy (0.5 mg/day of E2 and 0.1 mg/day of norethindrone acetate).

Among subjects in the 200 mg/day compound (II) stand-alone arm, amenorrhea was observed in at least 87% of subjects (13/15 subjects) during the last 4 weeks of treatment, and no bleeding or spotting was observed in 100% of subjects (15/15 subjects) during the final 4 weeks of treatment. Among subjects in the 200 mg/day compound (II) arm that also received 1.0 mg E2 and 0.5 mg norethindrone acetate, amenorrhea was observed in at least 33% of subjects (5/15 subjects) during the last 4 weeks of treatment, and no bleeding or spotting was observed in at least 60% of subjects (9/15 subjects) during the final 4 weeks of treatment.

Figure 18:
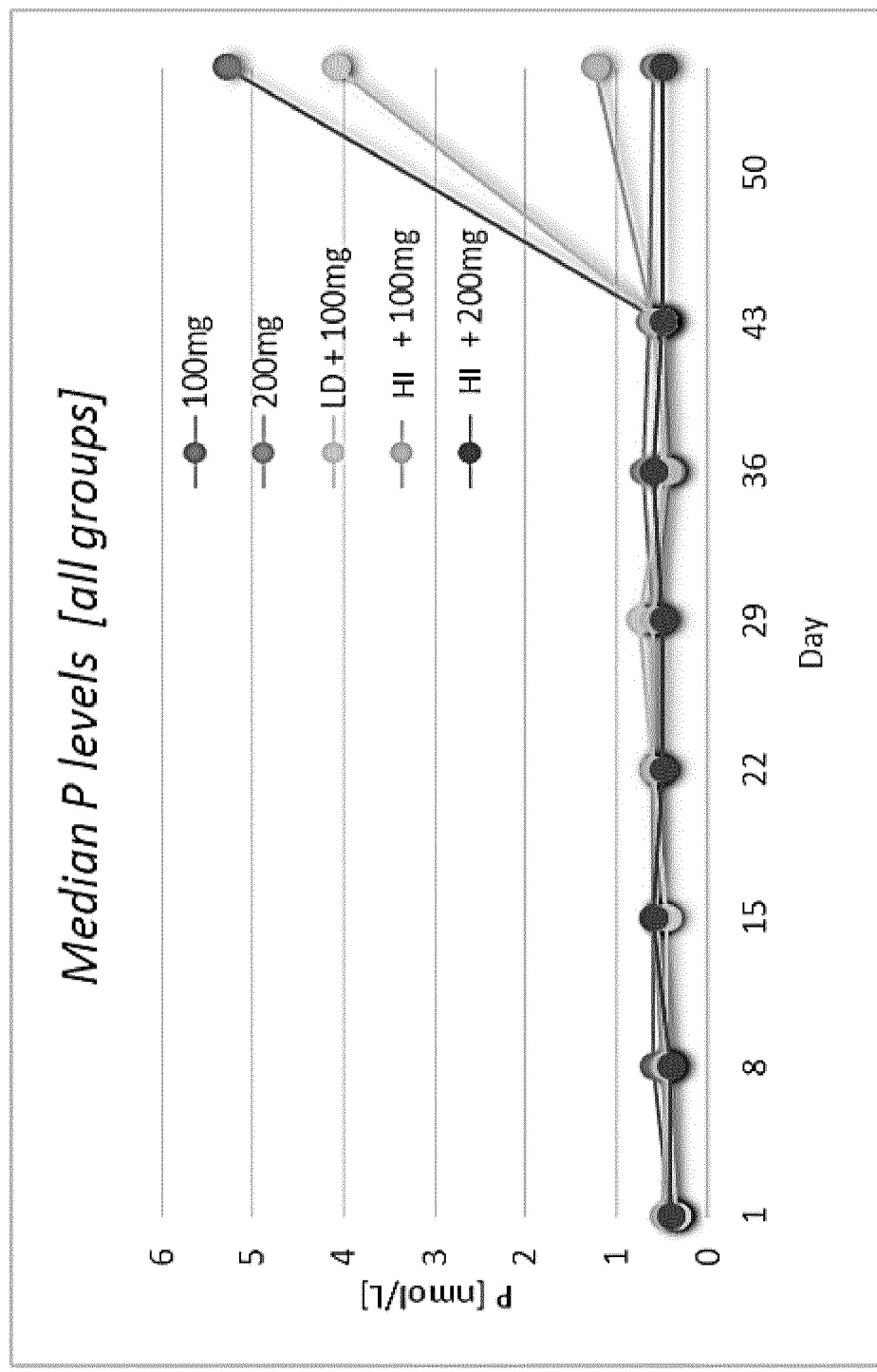
FIG. 18 is a graph demonstrating the effect of various doses of compound (II), with or without add-back therapy, on the median serum progesterone concentration of healthy human female subjects over the course of a 55-day period, during which subjects were administered compound (II), with or without add-back therapy, once daily for 42 days, followed by a post-treatment monitoring period. Data are shown in the following order, from bottom to top as observed at day 50: HI+200 mg of compound (II), 200 mg of compound (II) alone, HI+100 mg of compound (II), LD+100 mg of compound (II), 100 mg of compound (II) alone.
Figure 19A:
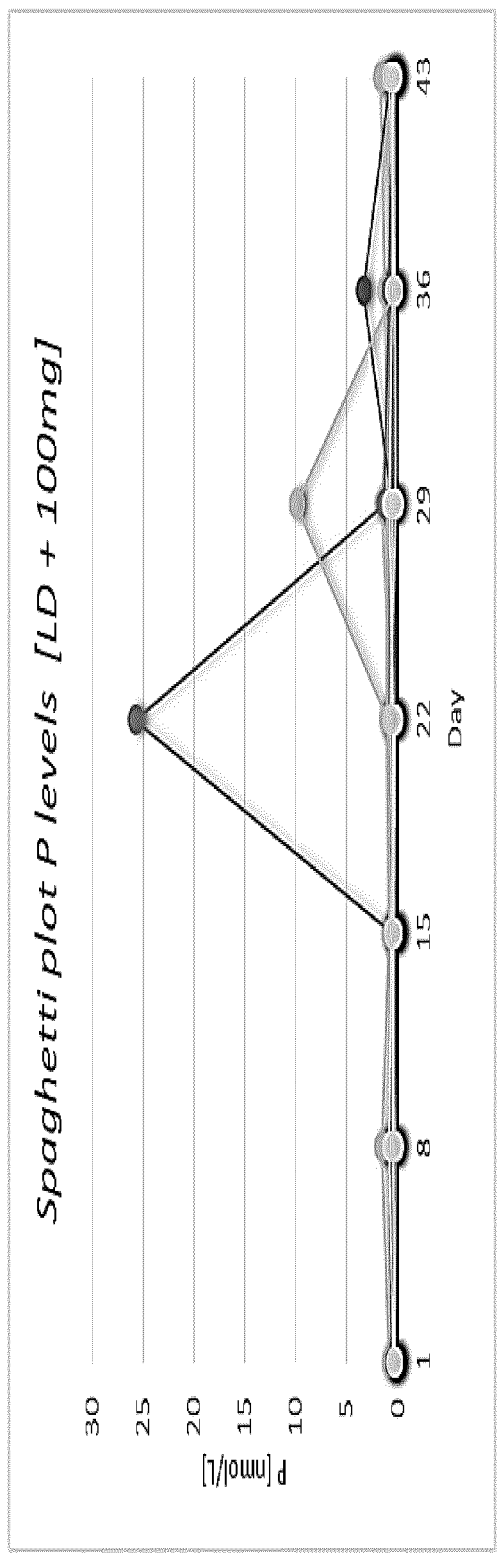
FIG. 19A is a graph demonstrating the effect of 100 mg/day of compound (II), in combination with 0.5 mg/day of β17-estradiol and 0.1 mg/day of norethindrone acetate, on the serum progesterone concentrations of each of 15 healthy human female subject over the course of a 42-day treatment period, followed by a post-treatment period in which subjects were monitored, but were not administered a therapeutic agent.
Figure 19B:
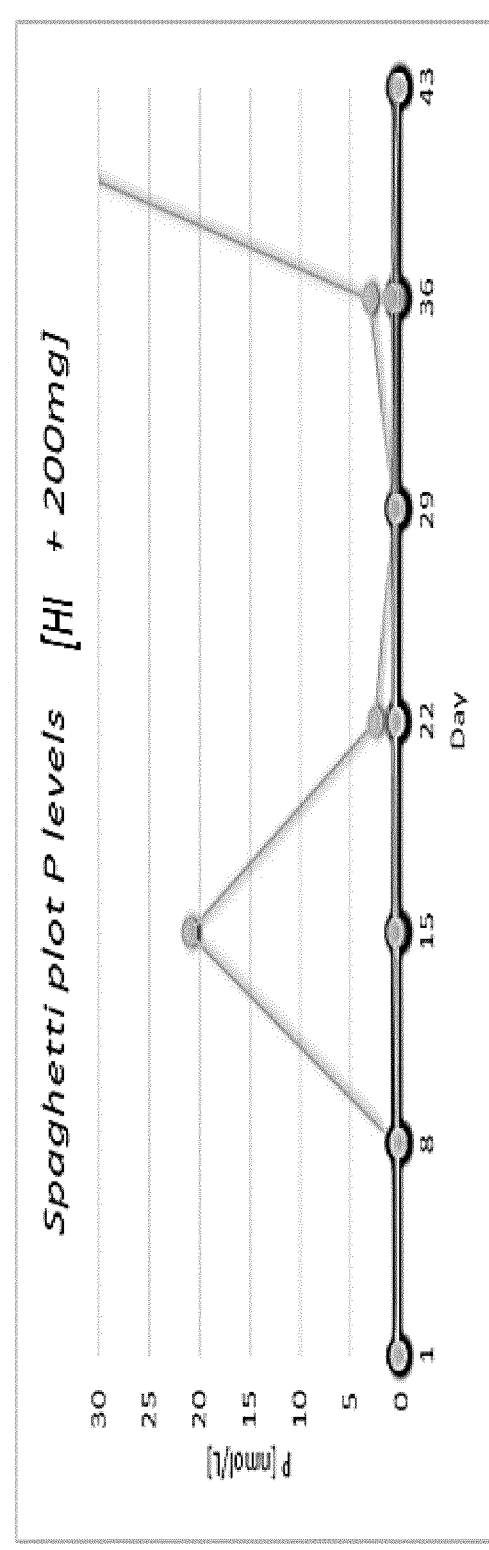
FIG. 19B is a graph demonstrating the effect of 200 mg/day of compound (II), in combination with 1.0 mg/day of β17-estradiol and 0.5 mg/day of norethindrone acetate, on the serum progesterone concentrations of each of 15 healthy human female subject over the course of a 42-day treatment period, followed by a post-treatment period in which subjects were monitored, but were not administered a therapeutic agent.
Figure 20:
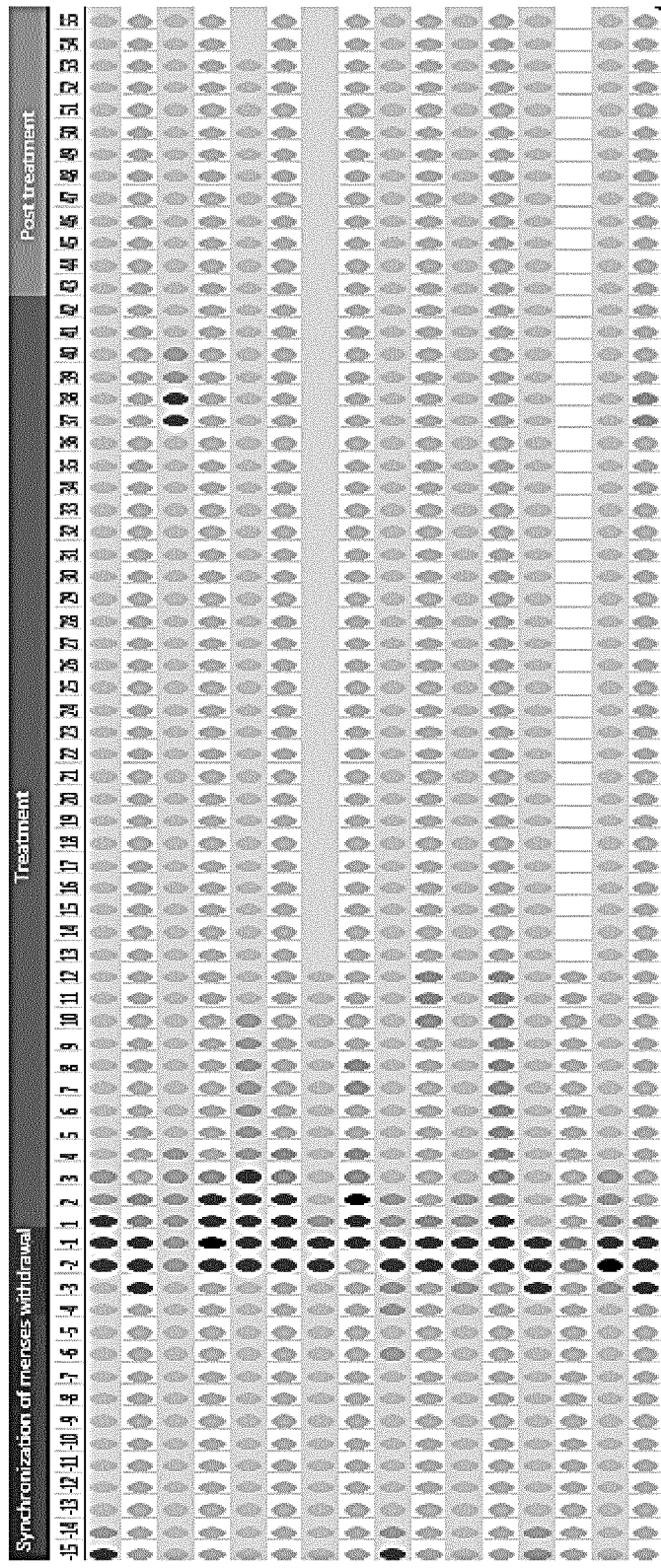
FIG. 20 is a chart illustrating the effect of 100 mg/day of compound (II), without add-back therapy, on menstrual bleeding in human female subjects over the course of an 11-day screening period, 4-day withdrawal period, 42-treatment period, and a 13-day post-treatment evaluation period. Assessment of menstrual blood loss was conducted using the alkaline hematin method. Each row of the chart denotes an individual subject's bleeding pattern over the full course of the experiment. The chart uses a shading continuum to convey the quantity of menstrual blood lost on each day as follows: The darkest spots in each row represent the days of heaviest bleeding, spots of intermediate darkness represent moderate bleeding, and spots of little darkness designate spotting. The lightest spots in the chart indicate that no menstrual bleeding was observed.
Figure 21:
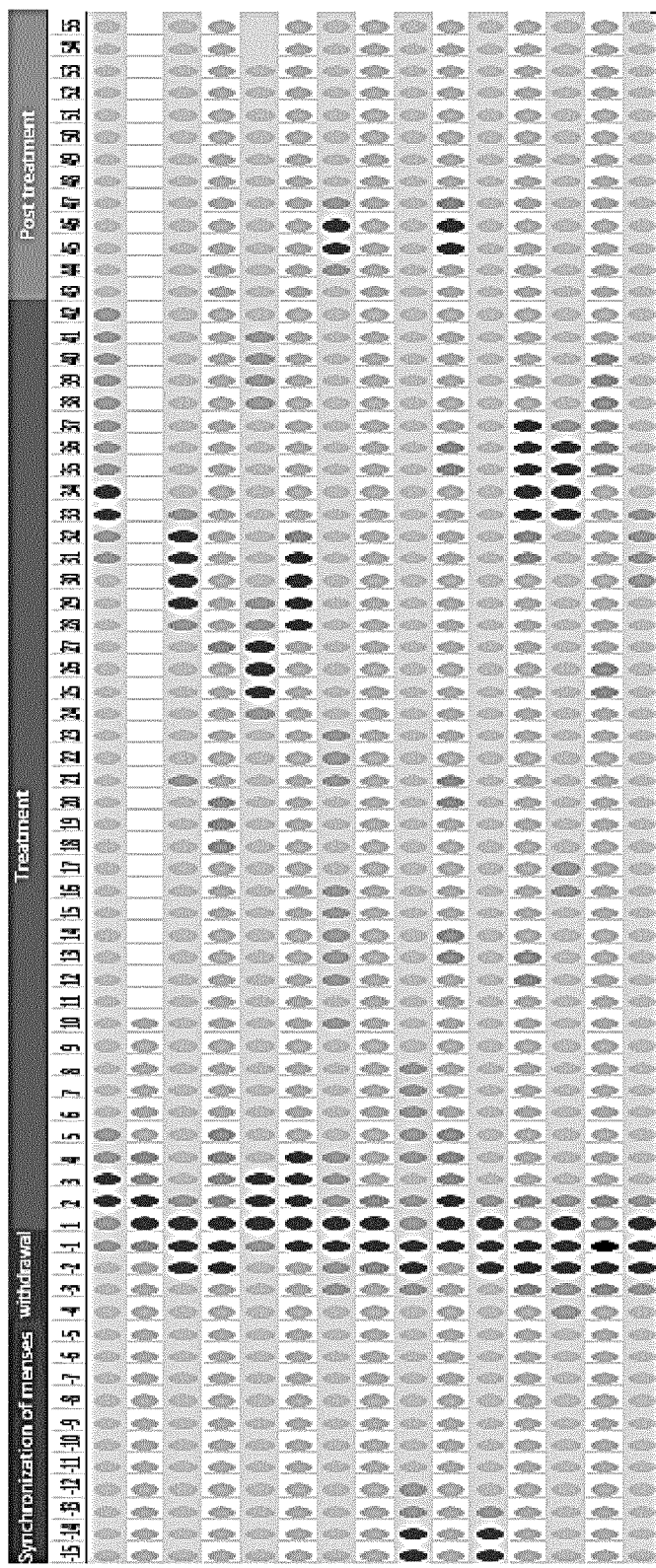
FIG. 21 is a chart illustrating the effect of 100 mg/day of compound (II), in combination with 0.5 mg/day of β17-estradiol and 0.1 mg/day of norethindrone acetate, on menstrual bleeding in human female subjects over the course of an 11-day screening period, 4-day withdrawal period, 42-treatment period, and a 13-day post-treatment evaluation period. Assessment of menstrual blood loss was conducted using the alkaline hematin method. Each row of the chart denotes an individual subject's bleeding pattern over the full course of the experiment. The chart uses a shading continuum to convey the quantity of menstrual blood lost on each day as follows: The darkest spots in each row represent the days of heaviest bleeding, spots of intermediate darkness represent moderate bleeding, and spots of little darkness designate spotting. The lightest spots in the chart indicate that no menstrual bleeding was observed.
Figure 22:
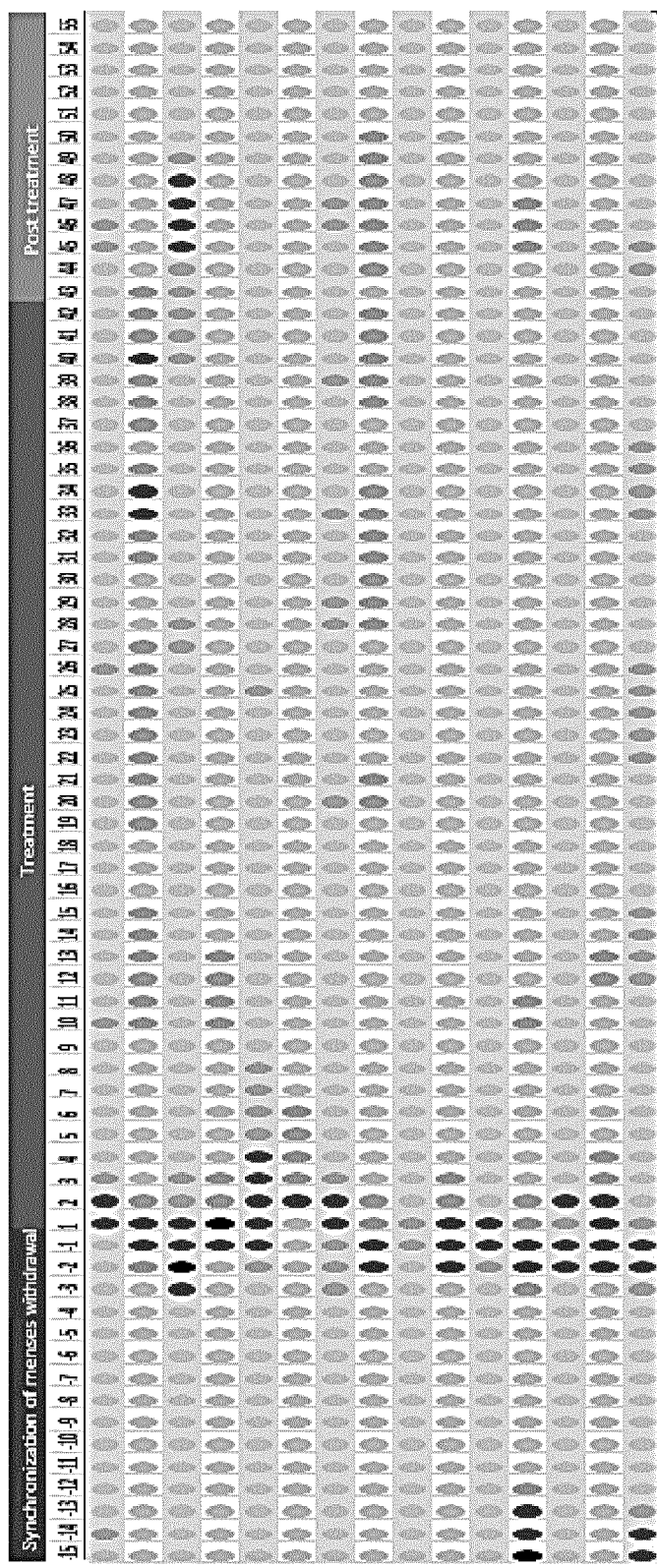
FIG. 22 is a chart illustrating the effect of 100 mg/day of compound (II), in combination with 1.0 mg/day of β17-estradiol and 0.5 mg/day of norethindrone acetate, on menstrual bleeding in human female subjects over the course of an 11-day screening period, 4-day withdrawal period, 42-treatment period, and a 13-day post-treatment evaluation period. Assessment of menstrual blood loss was conducted using the alkaline hematin method. Each row of the chart denotes an individual subject's bleeding pattern over the full course of the experiment. The chart uses a shading continuum to convey the quantity of menstrual blood lost on each day as follows: The darkest spots in each row represent the days of heaviest bleeding, spots of intermediate darkness represent moderate bleeding, and spots of little darkness designate spotting. The lightest spots in the chart indicate that no menstrual bleeding was observed.
Figure 23:
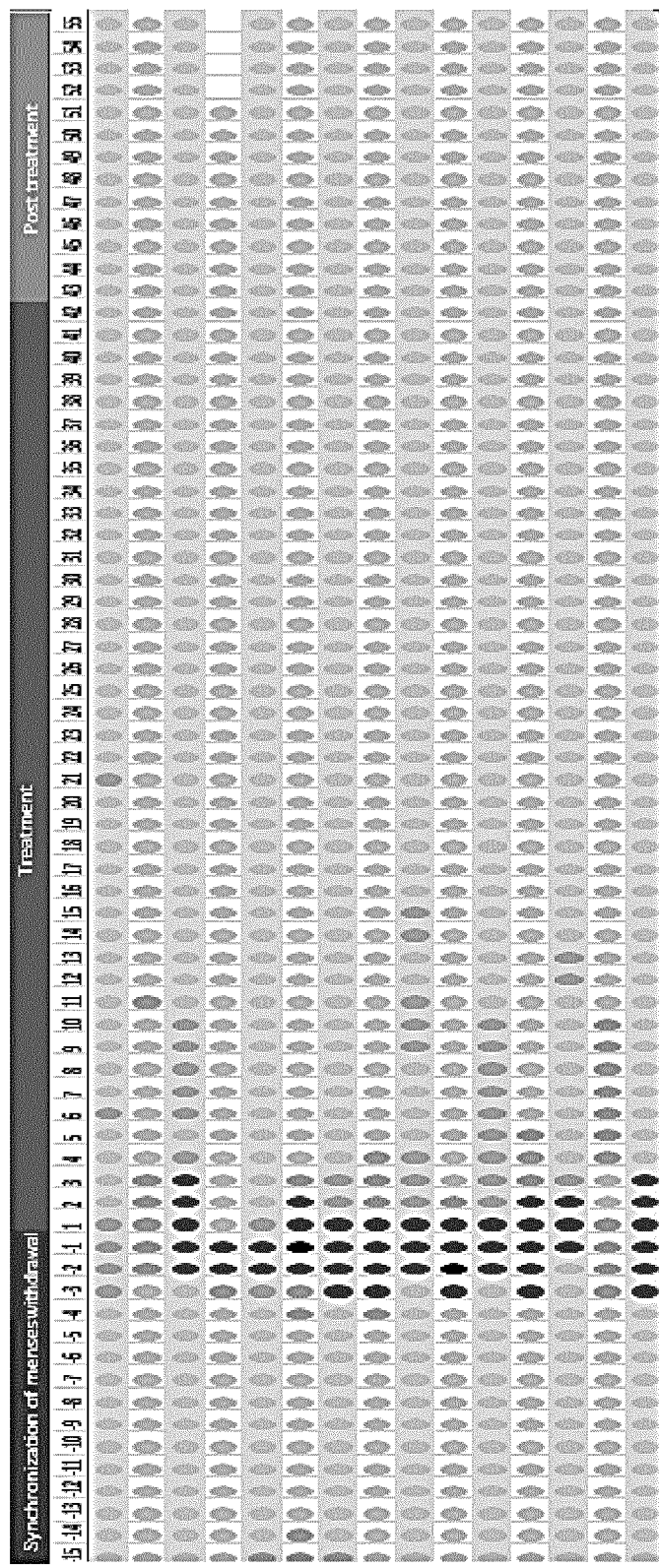
FIG. 23 is a chart illustrating the effect of 200 mg/day of compound (II), without add-back therapy, on menstrual bleeding in human female subjects over the course of an 11-day screening period, 4-day withdrawal period, 42-treatment period, and a 13-day post-treatment evaluation period. Assessment of menstrual blood loss was conducted using the alkaline hematin method. Each row of the chart denotes an individual subject's bleeding pattern over the full course of the experiment. The chart uses a shading continuum to convey the quantity of menstrual blood lost on each day as follows: The darkest spots in each row represent the days of heaviest bleeding, spots of intermediate darkness represent moderate bleeding, and spots of little darkness designate spotting. The lightest spots in the chart indicate that no menstrual bleeding was observed.
Figure 24:
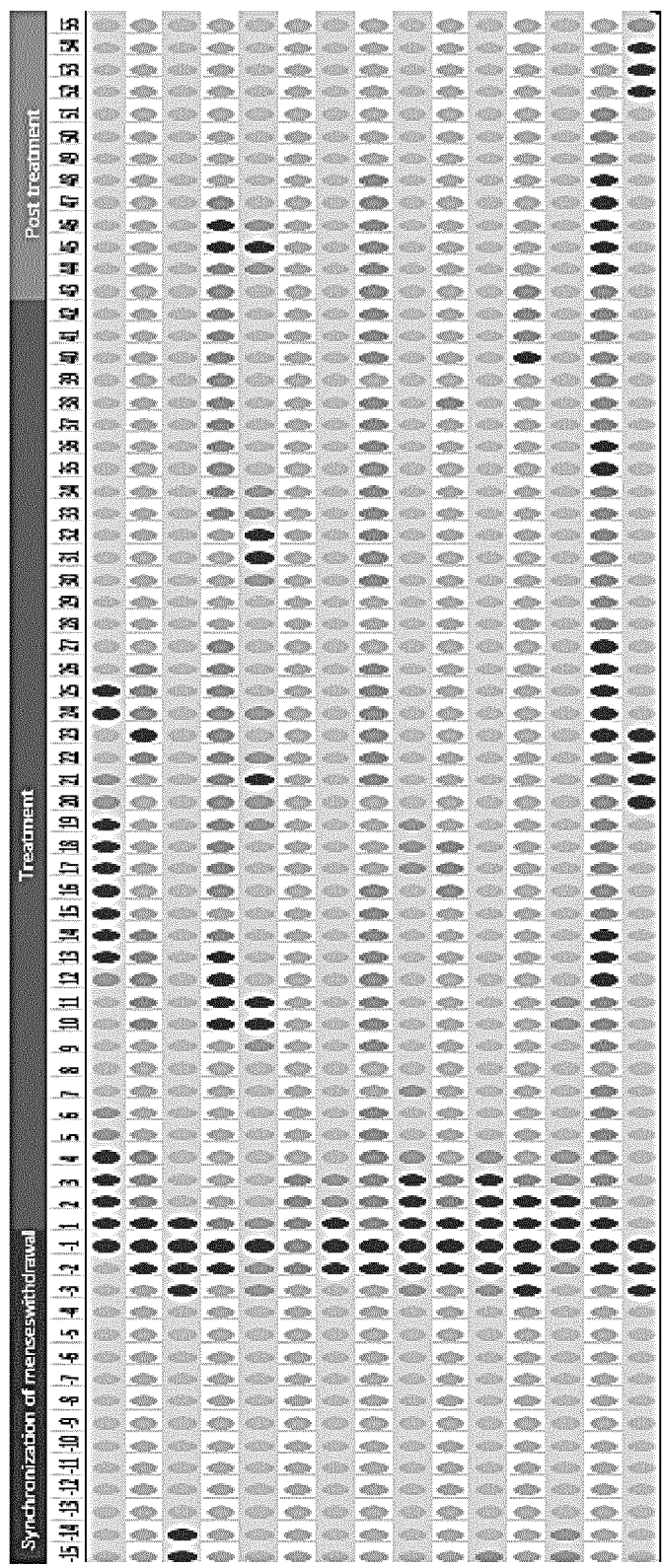
FIG. 24 is a chart illustrating the effect of 200 mg/day of compound (II), in combination with 1.0 mg/day of β17-estradiol and 0.5 mg/day of norethindrone acetate, on menstrual bleeding in human female subjects over the course of an 11-day screening period, 4-day withdrawal period, 42-treatment period, and a 13-day post-treatment evaluation period. Assessment of menstrual blood loss was conducted using the alkaline hematin method. Each row of the chart denotes an individual subject's bleeding pattern over the full course of the experiment. The chart uses a shading continuum to convey the quantity of menstrual blood lost on each day as follows: The darkest spots in each row represent the days of heaviest bleeding, spots of intermediate darkness represent moderate bleeding, and spots of little darkness designate spotting. The lightest spots in the chart indicate that no menstrual bleeding was observed.

Effects of choline 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylate on Serum Progesterone In addition to modulating serum E2 concentration, compound (II) was additionally capable of maintaining a consistent, low level of progesterone throughout the 42-day treatment period (FIG. 18). As shown in FIGS. 18 and 19, compound (II) was capable of sustaining reduced serum progesterone levels (from 0.51 nM to 0.69 nM) with low variability, with the exception of three outliers in the study (FIG. 19). As serum progesterone levels are positively correlated with ovulation, the GnRH antagonists described herein may therefore modulate ovulation in the patient, for instance, throughout the duration of a treatment cycle.

Figure 25:
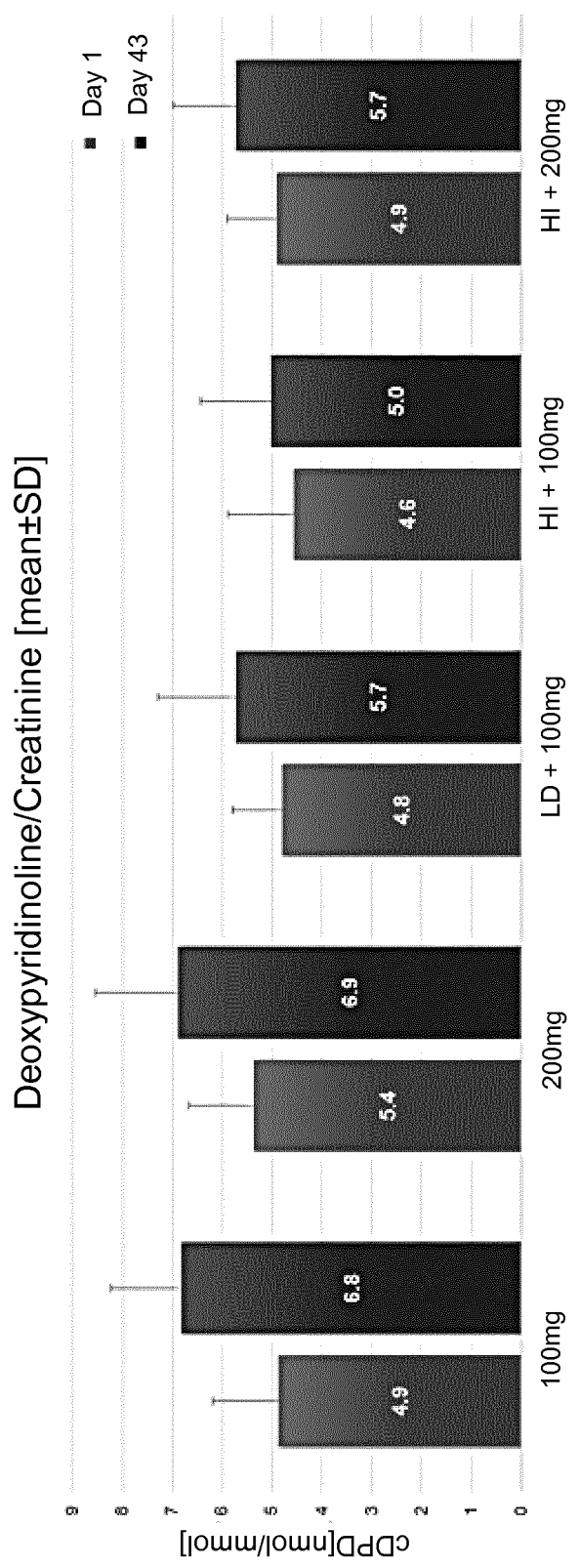
FIG. 25 is a graph demonstrating the effect of various doses of compound (II), with or without add-back therapy, on the ratio of deoxypyridinoline, a biomarker of bone resorption, to creatinine in urine samples obtained from healthy human female subjects over the course of a 43-day period, during which subjects were administered compound (II), with or without add-back therapy, once daily for 42 days, followed by a post-treatment monitoring period. Certain subjects received 100 mg/day or 200 mg/day of compound (II) as stand-alone therapeutics, while others received compound (II) in combination with 1.0 mg/day of β17-estradiol and 0.5 mg/day of norethindrone acetate or in combination with 0.5 mg/day of β17-estradiol and 0.1 mg/day of norethindrone acetate.
Figure 26:
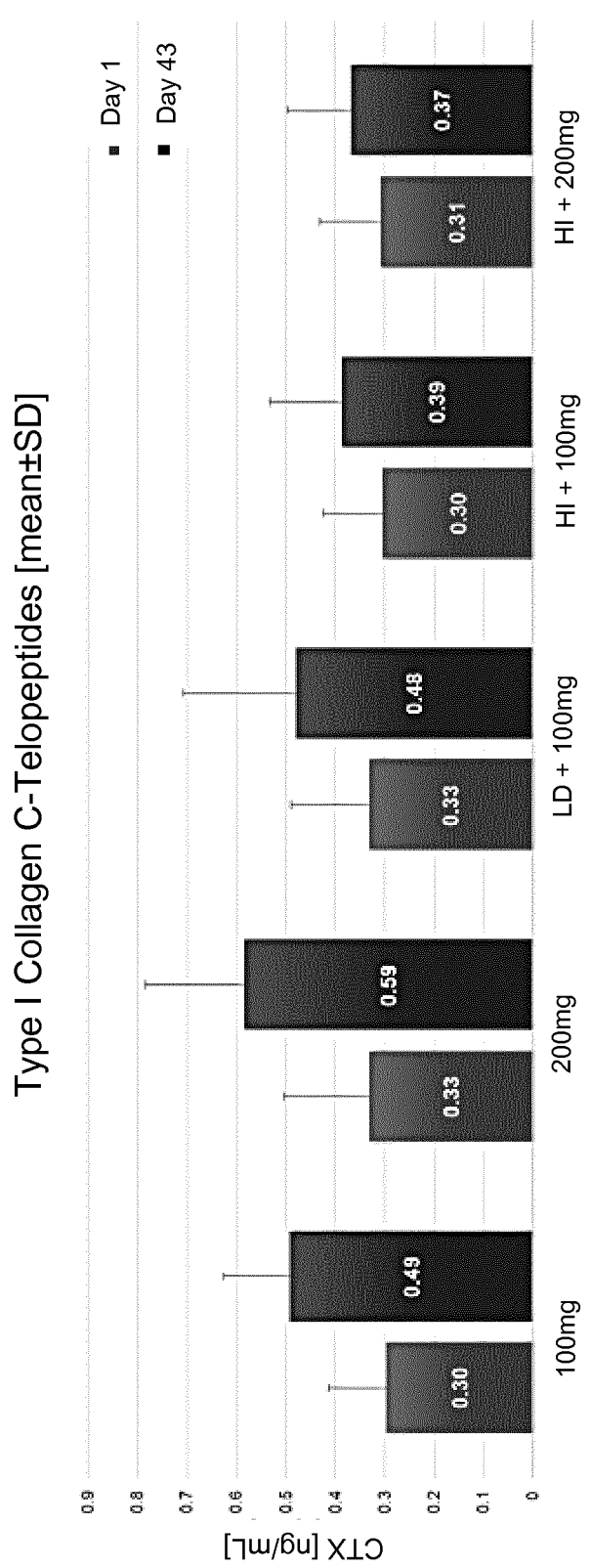
FIG. 26 is a graph demonstrating the effect of various doses of compound (II), with or without add-back therapy, on type I collagen C-terminal telopeptide, a biomarker of bone mineral density loss, in urine samples obtained from healthy human female subjects over the course of a 43-day period, during which subjects were administered compound (II), with or without add-back therapy, once daily for 42 days, followed by a post-treatment monitoring period. Certain subjects received 100 mg/day or 200 mg/day of compound (II) as stand-alone therapeutics, while others received compound (II) in combination with 1.0 mg/day of β17-estradiol and 0.5 mg/day of norethindrone acetate or in combination with 0.5 mg/day of β17-estradiol and 0.1 mg/day of norethindrone acetate.
Figure 27:
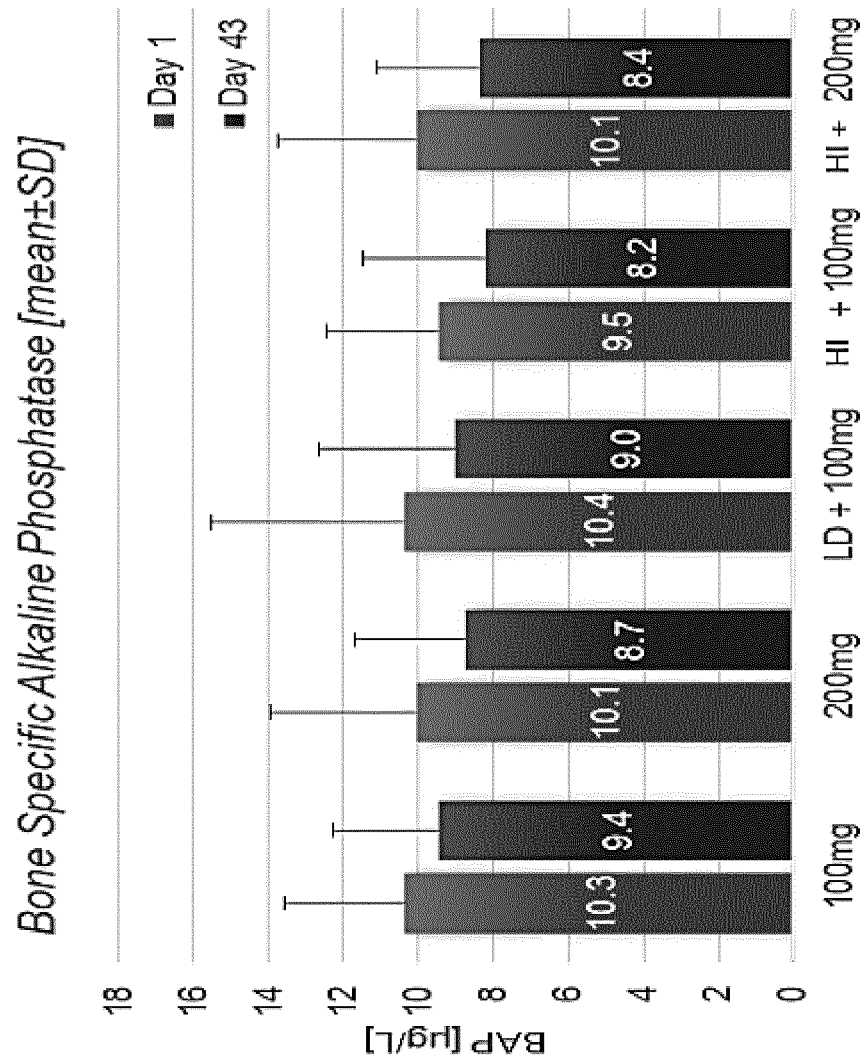
FIG. 27 is a graph demonstrating the effect of various doses of compound (II), with or without add-back therapy, on bone specific alkaline phosphatase, a biomarker of bone mineral density loss, in urine samples obtained from healthy human female subjects over the course of a 43-day period, during which subjects were administered compound (II), with or without add-back therapy, once daily for 42 days, followed by a post-treatment monitoring period. Certain subjects received 100 mg/day or 200 mg/day of compound (II) as stand-alone therapeutics, while others received compound (II) in combination with 1.0 mg/day of β17-estradiol and 0.5 mg/day of norethindrone acetate or in combination with 0.5 mg/day of β17-estradiol and 0.1 mg/day of norethindrone acetate.
Figure 28:
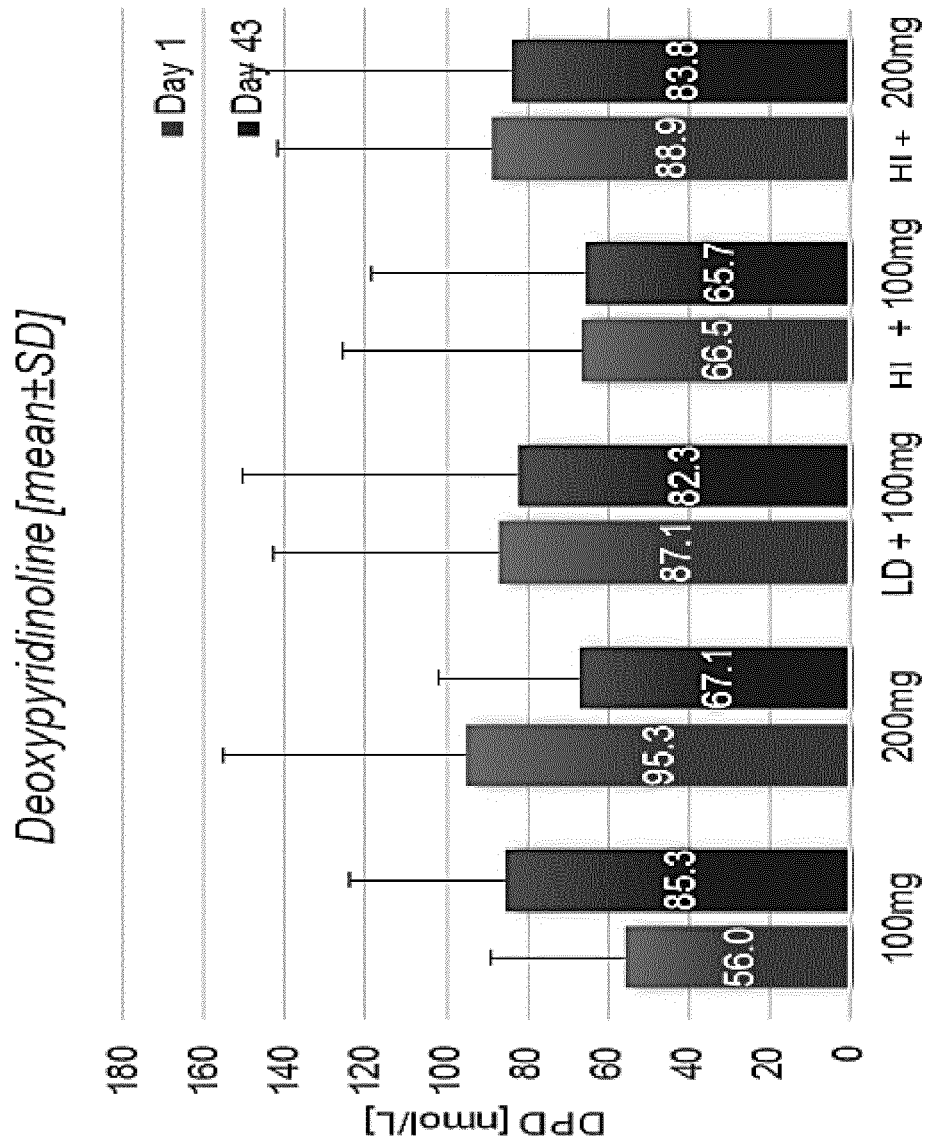
FIG. 28 is a graph demonstrating the effect of various doses of compound (II), with or without add-back therapy, on deoxypyridinoline, a biomarker of bone resorption, in urine samples obtained from healthy human female subjects over the course of a 43-day period, during which subjects were administered compound (II), with or without add-back therapy, once daily for 42 days, followed by a post-treatment monitoring period. Certain subjects received 100 mg/day or 200 mg/day of compound (II) as stand-alone therapeutics, while others received compound (II) in combination with 1.0 mg/day of β17-estradiol and 0.5 mg/day of norethindrone acetate or in combination with 0.5 mg/day of β17-estradiol and 0.1 mg/day of norethindrone acetate.
Figure 29:
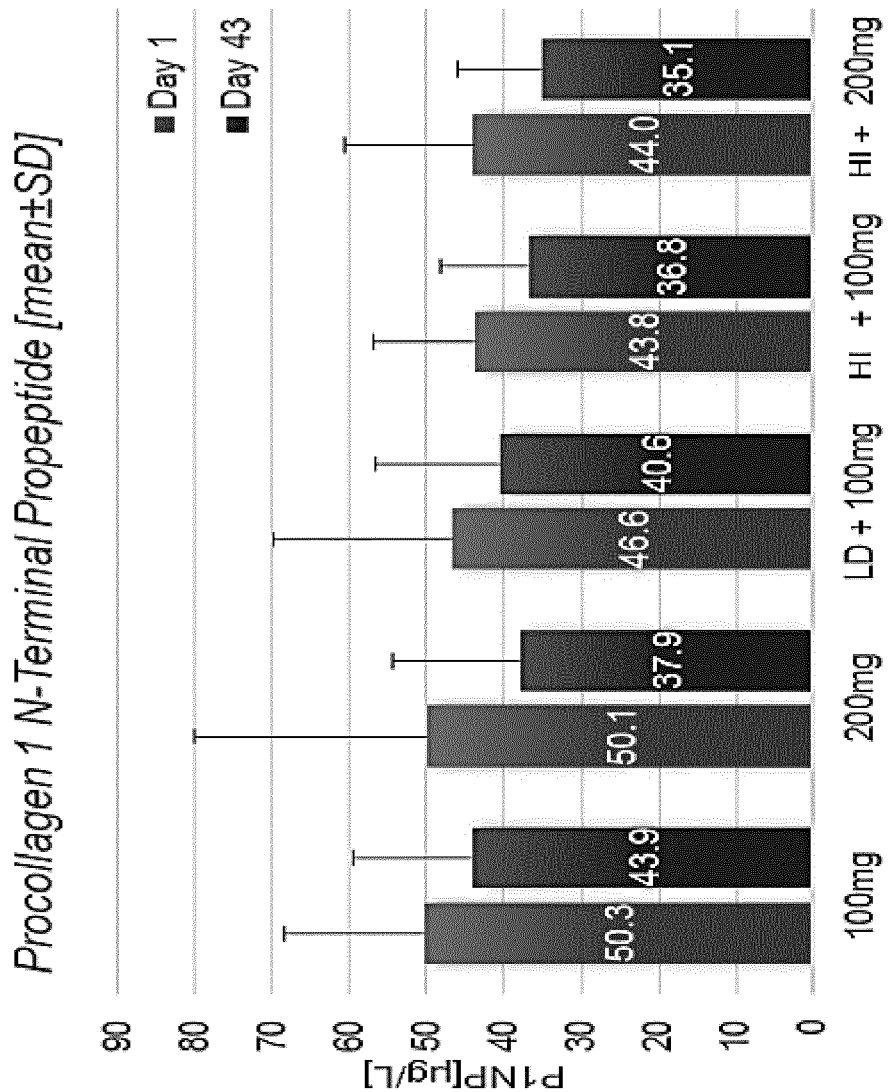
FIG. 29 is a graph demonstrating the effect of various doses of compound (II), with or without add-back therapy, on procollagen 1 N-terminal propeptide, a biomarker of bone mineral density loss, in urine samples obtained from healthy human female subjects over the course of a 43-day period, during which subjects were administered compound (II), with or without add-back therapy, once daily for 42 days, followed by a post-treatment monitoring period. Certain subjects received 100 mg/day or 200 mg/day of compound (II) as stand-alone therapeutics, while others received compound (II) in combination with 1.0 mg/day of β17-estradiol and 0.5 mg/day of norethindrone acetate or in combination with 0.5 mg/day of β17-estradiol and 0.1 mg/day of norethindrone acetate.
Figure 30:
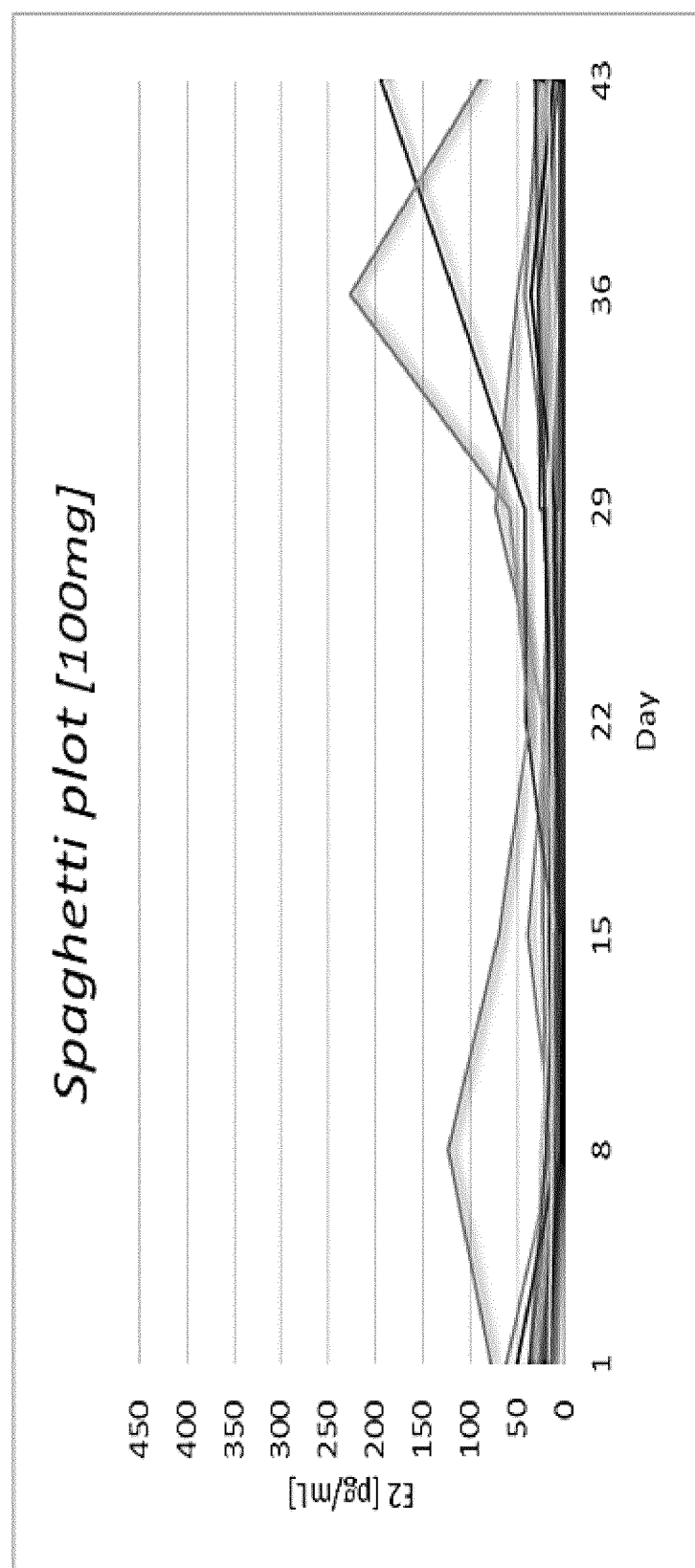
FIG. 30 is a graph demonstrating the effect of 100 mg/day of compound (II), without add-back therapy, on the serum β17-estradiol concentrations of 15 healthy human female subjects over the course of a 43-day period, during which subjects were administered compound (II) once daily for 42 days, followed by a post-treatment monitoring period.
Figure 31:
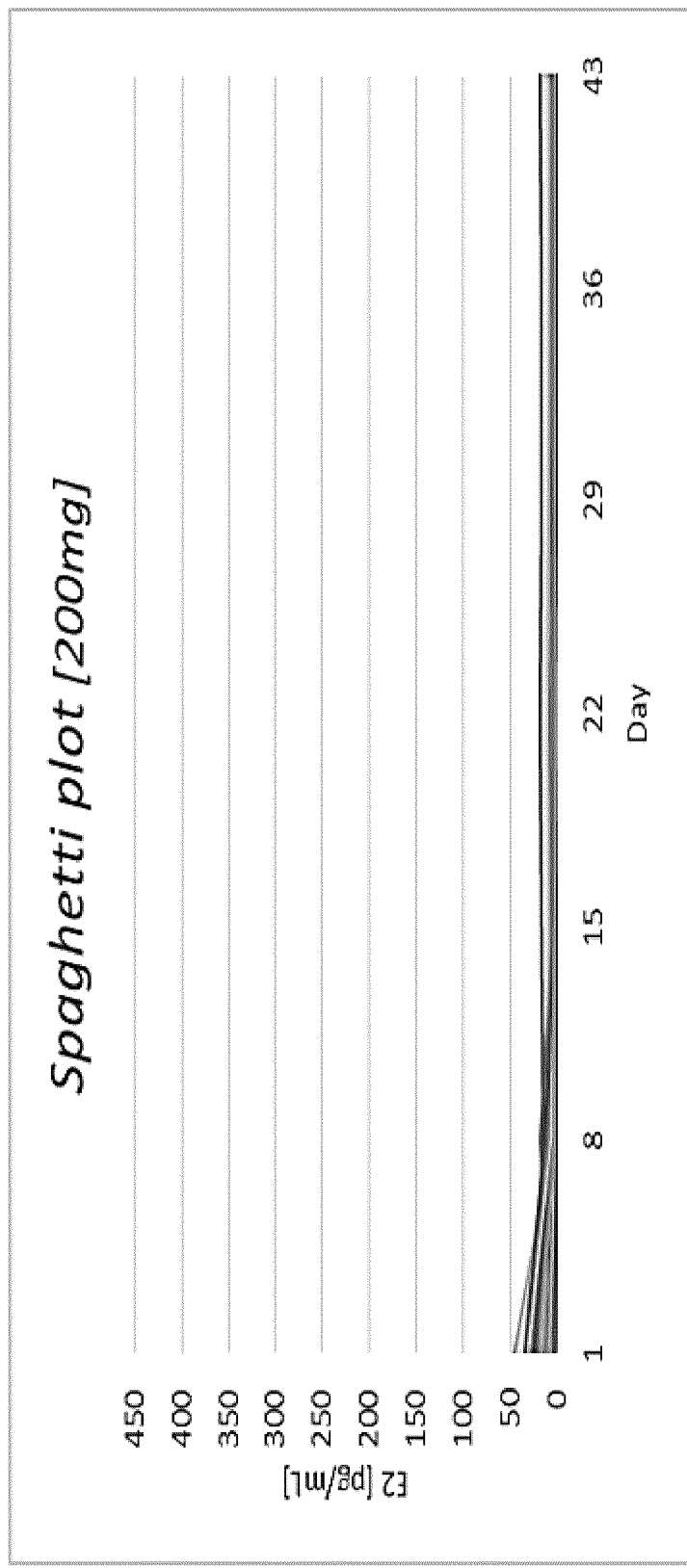
FIG. 31 is a graph demonstrating the effect of 200 mg/day of compound (II), without add-back therapy, on the serum β17-estradiol concentrations of 15 healthy human female subjects over the course of a 43-day period, during which subjects were administered compound (II) once daily for 42 days, followed by a post-treatment monitoring period.
Figure 32:
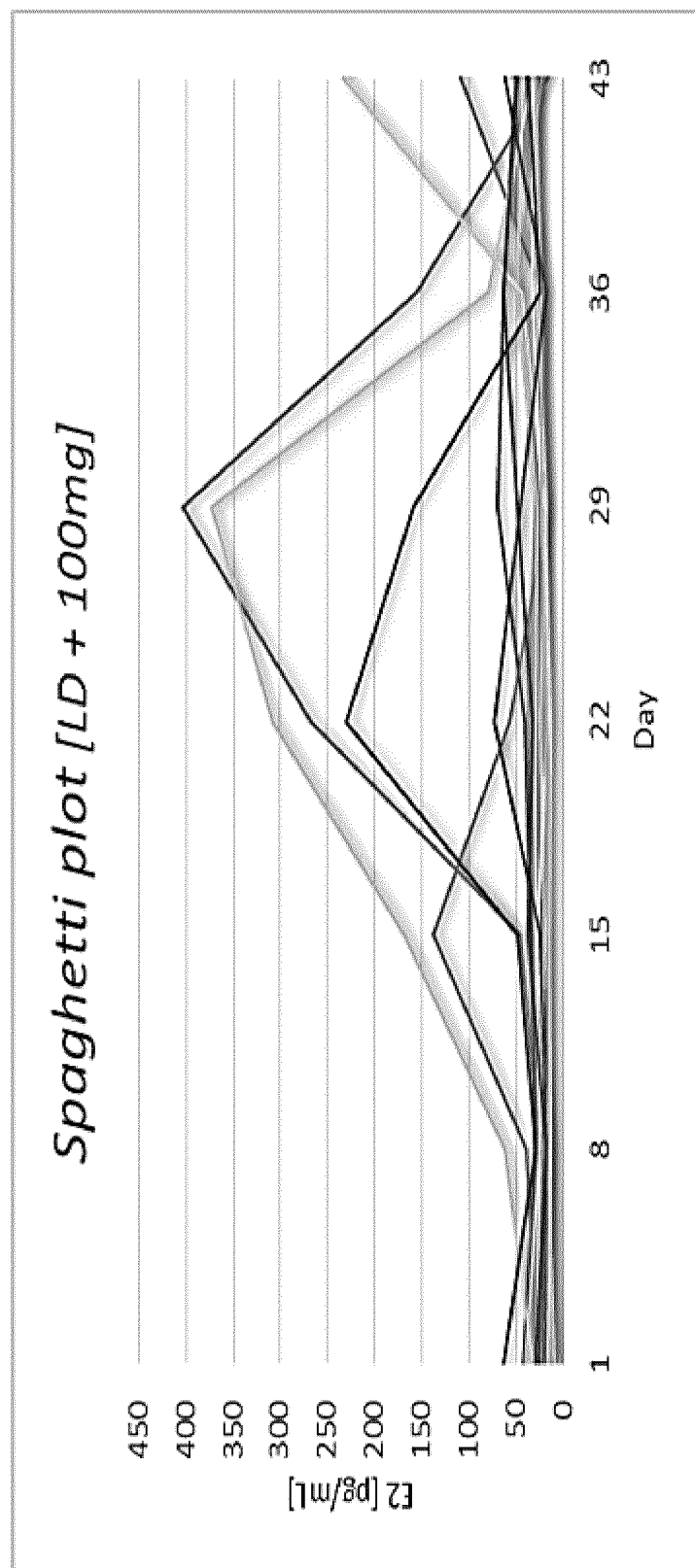
FIG. 32 is a graph demonstrating the effect of 100 mg/day of compound (II), in combination with 0.5 mg/day of β17-estradiol and 0.1 mg/day of norethindrone acetate, on the serum β17-estradiol concentrations of 15 healthy human female subjects over the course of a 43-day period, during which subjects were administered compound (II) once daily for 42 days, followed by a post-treatment monitoring period.
Figure 33:
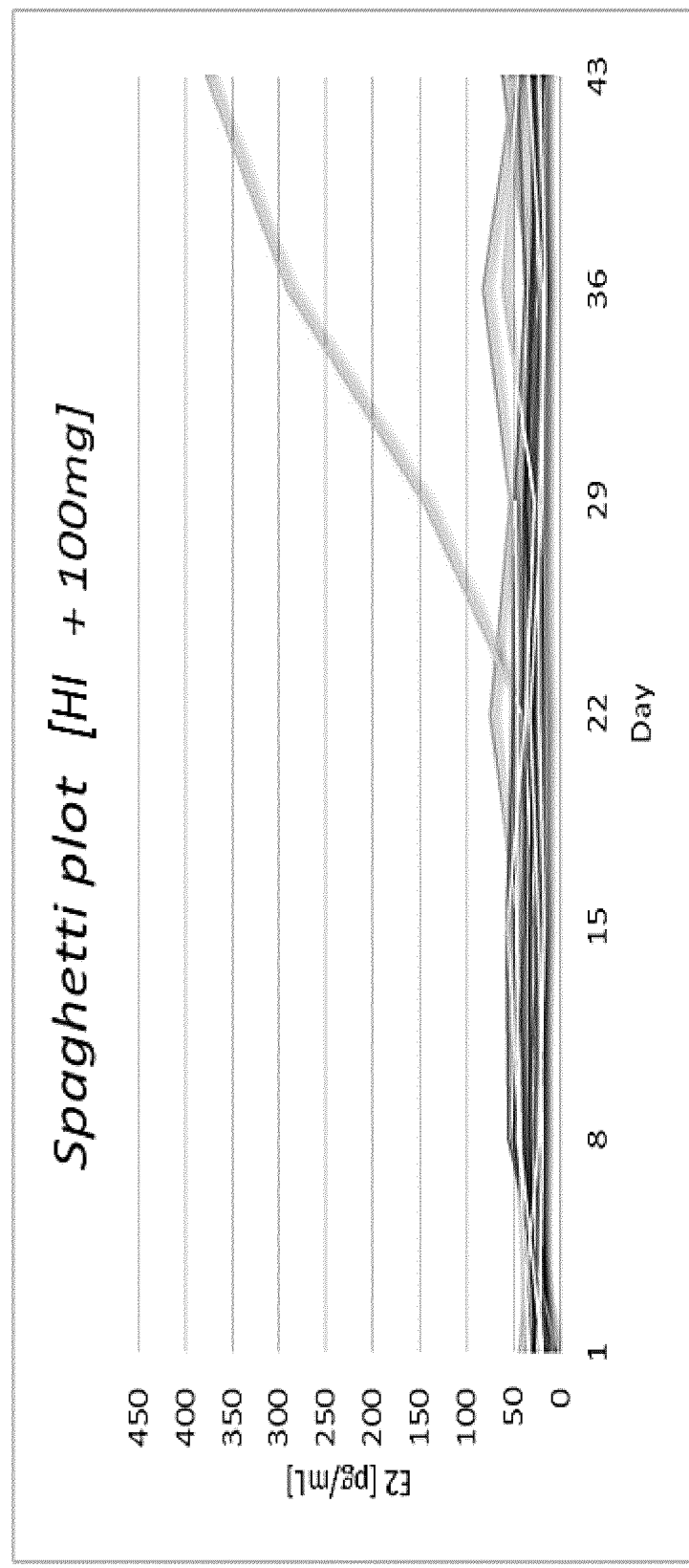
FIG. 33 is a graph demonstrating the effect of 100 mg/day of compound (II), in combination with 1.0 mg/day of β17-estradiol and 0.5 mg/day of norethindrone acetate, on the serum β17-estradiol concentrations of 15 healthy human female subjects over the course of a 43-day period, during which subjects were administered compound (II) once daily for 42 days, followed by a post-treatment monitoring period.
Figure 34:
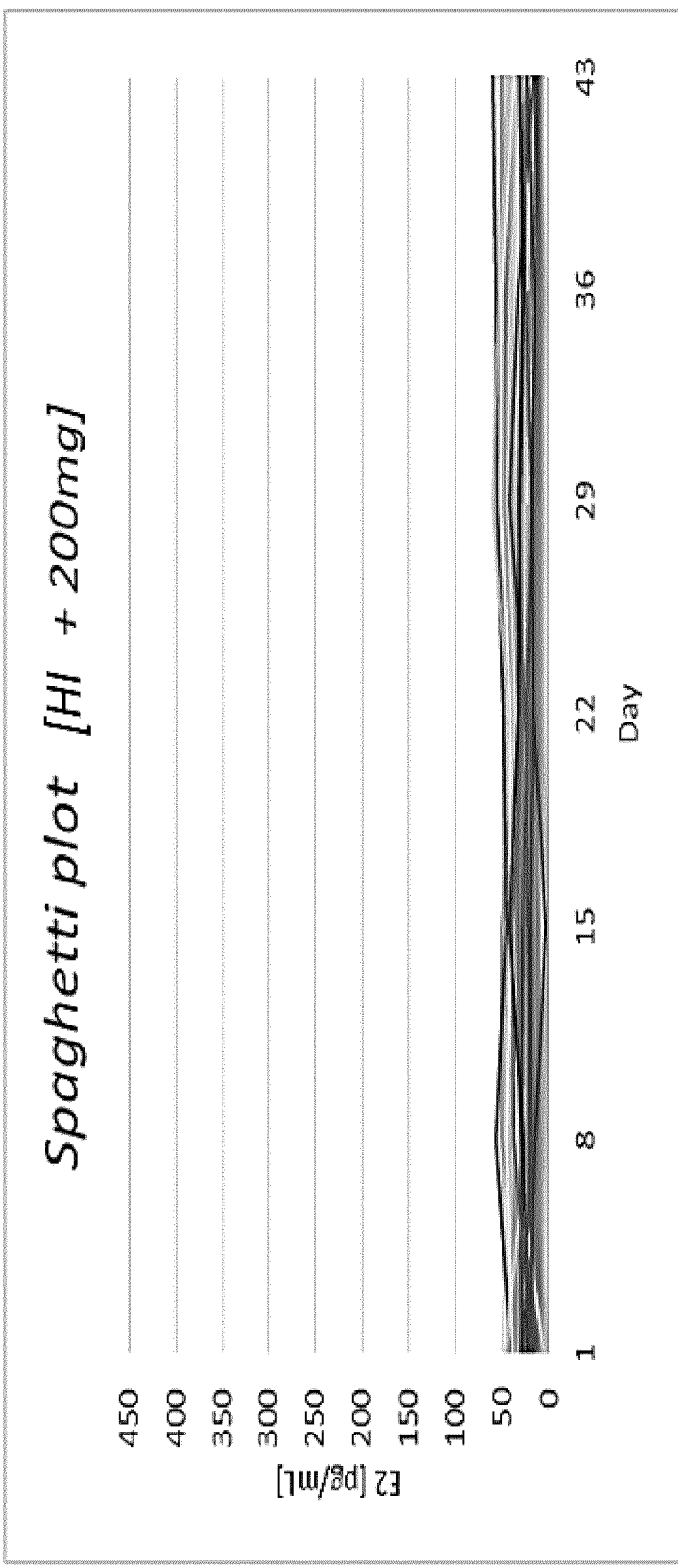
FIG. 34 is a graph demonstrating the effect of 200 mg/day of compound (II), in combination with 1.0 mg/day of β17-estradiol and 0.5 mg/day of norethindrone acetate, on the serum β17-estradiol concentrations of 15 healthy human female subjects over the course of a 43-day period, during which subjects were administered compound (II) once daily for 42 days, followed by a post-treatment monitoring period.

Effects of choline 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylate on Bone Mineral Density In addition to assessing the ability of compound (II) to modulate serum E2 and progesterone levels and to curtail menstrual bleeding, compound (II) was evaluated for its effects on biomarkers of bone mineral density (FIGS. 25-29). These markers include creatinine-normalized deoxypyridinoline (DPD), which is excreted in larger quantities when bone resorption is increased. As shown in FIG. 25, creatinine-normalized DPD exhibited the smallest increase among subjects that received 100 mg/day of compound (II) in combination with 1.0 mg/day of E2 and 0.5 mg/day of norethindrone acetate.

Conclusion

Based on the evaluation of the pharmacokinetic and pharmacodynamic effects of compound (II) in 75 human female subjects, this compound was observed to suppress serum E2 in a dose-dependent fashion, with and without add-back therapy. This reduction in serum E2 concentration was correlated with the induction of sustained amenorrhea, particularly within the final four weeks of the treatment period. Additionally, subjects treated with compound (II) exhibited consistently low levels of progesterone throughout the treatment window, indicating that compound (II) provides the additional benefit of modulating ovulation.

The results of this investigation show that compound (II), when administered at 100 mg/day and 200 mg/day, rapidly reduced E2 to levels that are expected to treat symptoms of uterine fibroids, such as heavy menstrual bleeding. The marked E2 reduction seen with stand-alone dosing supports the use of add-back therapy to minimize bone mineral density loss, such as in patients that are administered 200 mg/day of compound (II), and potentially in subjects that are administered 100 mg/day of this compound. The additional administration of add-back therapy in this study to subjects treated with 100 mg/day and 200 mg/day of compound (II) restored E2 levels to the target range that would be expected to minimize bone mineral density loss. As for the bleeding pattern observed during the final 4 weeks of treatment, the vast majority of patients achieved amenorrhea when treated with compound (II) alone. Notably, the majority of patients in each treatment arm achieved a status of either "amenorrhea" or bleeding characterized as "spotting only", further demonstrating the benefit of compound (II), optionally combined with add-back therapy.

The results of this study are summarized in Tables 2 and 3, below.

TABLE 2

Median (IQR: 25-75%) E2 level after week 1 and 6 of treatment

| Compound (II) Daily Dose | 100 mg (n = 14) | 100 mg (n = 14) | 100 mg (n = 15) | 200 mg (n = 14) | 200 mg (n = 15) |
| --- | --- | --- | --- | --- | --- |
| Add-Back E2/NETA | — | 0.5 mg/ 0.1 mg | 1 mg/ 0.5 mg | — | 1 mg/ 0.5 mg |
| E2 Week 1 [pg/mL] | 12 (9-18) | 25 (18-30) | 35 (26-45) | 5 (4-7) | 27 (22-38) |
| E2 Week 6 [pg/mL] | 18 (9-27) | 40 (31-50) | 34 (26-47) | 3 (2-3) | 25 (21-34) |

TABLE 3

Bleeding pattern during the last 4 weeks of treatment

| Compound (II) Daily Dose | 100 mg (n = 14) | 100 mg (n = 14) | 100 mg (n = 15) | 200 mg (n = 15) | 200 mg (n = 15) |
| --- | --- | --- | --- | --- | --- |
| Add-Back E2/NETA | — | 0.5 mg/ 0.1 mg | 1 mg/ 0.5 mg | — | 1 mg/ 0.5 mg |
| Amenorrhea (no bleeding) | 86% | 21% | 53% | 87% | 33% |
| Amenorrhea + spotting only | 93% | 57% | 93% | 100% | 60% |

Example 2. Use of a GnRH Antagonist Dosing Regimen for the Treatment of a Patient Having Uterine Fibroids and an Accompanying Anemia Using the dosing regimens described herein, a human patient suffering from uterine fibroids and having an accompanying anemia, such as an iron deficiency anemia, can be effectively treated so as to exhibit reduced menstrual blood loss. For example, upon identifying a patient as having uterine fibroids and an anemia due to heavy menstrual blood loss, a physician of skill in the art may prescribe to the patient a daily dosage of compound (I) or a pharmaceutically acceptable salt thereof, such as the choline salt thereof. The compound may be administered to the patient daily, for instance, at a dose of 100 mg/day as a stand-alone therapeutic or in combination with add-back therapy, such as 1.0 mg/day of β17-estradiol and 0.5 mg/day of norethindrone acetate or 0.5 mg/day of β17-estradiol and 0.1 mg/day of norethindrone acetate. In an alternative example, the patient may be administered 200 mg/day of the GnRH antagonist in combination with add-back therapy, such as 1.0 mg/day of β17-estradiol and 0.5 mg/day of norethindrone acetate or 0.5 mg/day of β17-estradiol and 0.1 mg/day of norethindrone acetate.

In the event that add-back therapy is administered to the patient, the add-back therapy may be administered in combination with the GnRH antagonist, for instance, in a fixed-dose pharmaceutical composition, such as a single tablet, capsule, gel cap, powder, liquid solution, or liquid suspension that contains the GnRH antagonist and estrogen, and optionally a progestin. Alternatively, the add-back therapy may be administered in a separate composition, such as by oral, transdermal, or intravaginal administration.

As demonstrated by their ability to induce sustained amenorrhea in patients exhibiting menstrual bleeding (shown, e.g., in Example 1 above), compound (I) and pharmaceutically acceptable salts thereof, such as the choline salt (compound (II)), can be administered to a patient experiencing heavy menstrual bleeding and having an accompanying anemia, such as iron deficiency anemia, so as to induce a reduction in menstrual blood loss and to concomitantly ameliorate the patient's anemia by curtailing further red blood cell deficiency.

A physician of skill in the art may monitor the patient's menstrual blood loss over the course of the GnRH antagonist treatment cycle in order to evaluate the patient's progress towards reduced menstrual blood loss. To this end, the physician may use one or more methods known in the art or described herein to assess the patient's reduction in menstrual blood loss over the course of the GnRH antagonist therapy. For instance, the physician may quantitate the volume of menstrual blood lost by the patient using the alkaline hematin method as described above and in Hallberg et al., Scand. J. Clin. Lab. Invest. 16:244-248 (1964), the disclosure of which is incorporated herein by reference as it pertains to techniques for assessing the volume of blood lost by a patient. Additionally or alternatively, the physician may monitor the patient's reduction in menstrual blood loss by qualitatively assessing the amount of menstrual blood lost by the patient each day of the treatment cycle. The assessment of blood loss may inform the length of the treatment cycle or the period of time that lapses between consecutive treatment cycles.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of reducing the volume of menstrual blood loss in a female human patient, the method comprising administering to the patient a therapeutically effective amount of a compound, 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, or a pharmaceutically acceptable salt thereof, wherein the compound is administered to the patient in an amount of about 100 mg per day or about 200 mg per day, and wherein the patient is further administered add-back therapy comprising about 1.0 mg of β17-estradiol and about 0.5 mg of norethindrone acetate.

2. The method of claim 1, wherein the patient has uterine fibroids.

3. A method of treating uterine fibroids in a female human patient in need thereof, the method comprising administering to the patient a therapeutically effective amount of a compound, 3-[2-fluoro-5-(2,3-difluoro-6-methoxybenzyloxy)-4-methoxyphenyl]-2,4-dioxo-1,2,3,4-tetrahydrothieno [3,4d]pyrimidine-5-carboxylic acid, or a pharmaceutically acceptable salt thereof, wherein the compound is administered to the patient in an amount of about 100 mg per day or about 200 mg per day, and wherein the patient is further administered add-back therapy comprising about 1.0 mg of β17-estradiol and about 0.5 mg of norethindrone acetate.

4. The method of claim 2, wherein the compound is administered to the patient in the form of a pharmaceutically acceptable salt thereof.

5. The method of claim 4, wherein the pharmaceutically acceptable salt is a choline salt.

6. The method of claim 2, wherein the compound is administered to the patient orally.

7. The method of claim 2, wherein the compound is administered to the patient in an amount of about 200 mg per day.

8. The method of claim 7, wherein the compound is administered to the patient once daily.

9. The method of claim 2, wherein the add-back therapy is administered to the patient once daily.

10. The method of claim 3, wherein the compound is administered to the patient in the form of a pharmaceutically acceptable salt thereof.

11. The method of claim 10, wherein the pharmaceutically acceptable salt is a choline salt.

12. The method of claim 3, wherein the compound is administered to the patient orally.

13. The method of claim 3, wherein the compound is administered to the patient in an amount of about 200 mg per day.

14. The method of claim 13, wherein the compound is administered to the patient once daily.

15. The method of claim 3, wherein the add-back therapy is administered to the patient once daily.

* * * * *